United States Patent
Miron et al.

(10) Patent No.: US 11,492,366 B2
(45) Date of Patent: Nov. 8, 2022

(54) PLATINUM COMPOUNDS FOR BINDING GUANINE QUADRUPLEXES

(71) Applicants: QUEEN'S UNIVERSITY AT KINGSTON, Kingston (CA); INSTITUT NATIONAL DE LA SANTE ET DE LA RECHERCHE MEDICALE (INSERM), Paris (FR)

(72) Inventors: Caitlin Miron, Montreal (CA); Anne Petitjean, Kingston (CA); Jean-Louis Mergny, Pessac (FR)

(73) Assignees: Queen's University at Kingston; Institut National de la Sante et de la Recherche Medicale (Inserm)

( * ) Notice: Subject to any disclaimer, the term of this patent is extended or adjusted under 35 U.S.C. 154(b) by 332 days.

(21) Appl. No.: 16/761,310

(22) PCT Filed: Nov. 6, 2018

(86) PCT No.: PCT/CA2018/051399
§ 371 (c)(1),
(2) Date: May 4, 2020

(87) PCT Pub. No.: WO2019/084696
PCT Pub. Date: May 9, 2019

(65) Prior Publication Data
US 2021/0188889 A1 Jun. 24, 2021

Related U.S. Application Data

(60) Provisional application No. 62/581,964, filed on Nov. 6, 2017.

(51) Int. Cl.
| | | |
|---|---|---|
| *C07F 15/00* | (2006.01) |
| *A61P 35/00* | (2006.01) |
| *A61K 31/555* | (2006.01) |
| *A61K 31/728* | (2006.01) |
| *A61K 38/17* | (2006.01) |
| *A61K 38/36* | (2006.01) |
| *A61K 38/38* | (2006.01) |
| *A61K 39/395* | (2006.01) |
| *G01N 33/52* | (2006.01) |
| *C07F 13/00* | (2006.01) |
| *C07F 11/00* | (2006.01) |

(52) U.S. Cl.
CPC ........ *C07F 15/0093* (2013.01); *A61K 31/555* (2013.01); *A61K 31/728* (2013.01); *A61K 38/1709* (2013.01); *A61K 38/363* (2013.01); *A61K 38/385* (2013.01); *A61K 39/395* (2013.01); *A61P 35/00* (2018.01); *C07F 11/005* (2013.01); *C07F 13/005* (2013.01); *C07F 15/0053* (2013.01); *C07F 15/0066* (2013.01); *C07F 15/0073* (2013.01); *G01N 33/52* (2013.01)

(58) Field of Classification Search
CPC .. A61K 31/555; A61P 31/00–22; A61P 25/28; A61P 35/00; C07F 11/005; C07F 13/005; C07F 15/0053; C07F 15/0066; C07F 15/0073; C07F 15/0093
See application file for complete search history.

(56) References Cited

U.S. PATENT DOCUMENTS

| | | | | |
|---|---|---|---|---|
| 7,651,979 B2 * | 1/2010 | Lippard | .............. | C07F 15/0093 506/13 |
| 2017/0102330 A1* | 4/2017 | Ma | .......... | G01N 31/22 |

FOREIGN PATENT DOCUMENTS

| | | | | |
|---|---|---|---|---|
| WO | WO-2014023063 A1 * | 2/2014 | ......... | C07F 15/0093 |
| WO | WO-2019078715 A1 * | 4/2019 | | |

OTHER PUBLICATIONS

Klingele, J. et al "Triazolopyridines as ligands . . . " Dalton Trans., vol. 39, pp. 4495-4507. (Year: 2010).*
International Search Report and Written Opinion for corresponding International application No. PCT/CA2018/051399 filed on Nov. 6, 2018.
Cao, Q., et al., "G-quadruplex DNA targeted metal complexes acting as potential anticancer drugs", Inorganic Chemistry Frontiers, vol. 4, pp. 10-32, (2017).
Li, Qian et al., "G4LDB: a database for discovering and studying G-quadruplex ligands," Nucleic Acids Research, vol. 41, pp. D1115-D1123, (2013).
Chen, Z-F., et al., "Stabilization of G-Quadruplex DNA, Inhibition of Telomerase Activity, and Tumor Cell Apoptosis by Organoplatinum (II) Complexes with Oxoisoaporphine", Journal of Medical Chemistry, pp. 2159-2179, (2015).
Ma, D.-L., et al., "Platinum(II) Complexes with Dipyridophenazine Ligands as Human Telomerase Inhibitors and Luminescent Probes for G-Quadruplex DNA", JACS, vol. 131, pp. 1835-1846, (2009).

* cited by examiner

*Primary Examiner* — Leigh C Maier
(74) *Attorney, Agent, or Firm* — Licata & Tyrrell P.C.; Angela Lyon

(57) ABSTRACT

Compounds are described and characterized that bind guanine quadruplexes of DNA or RNA. Binding data and inhibition of growth data of five cancer cell lines are presented.

18 Claims, 6 Drawing Sheets
Specification includes a Sequence Listing.

PLATINUM COMPOUNDS FOR BINDING GUANINE QUADRUPLEXES

RELATED APPLICATION

This application is a U.S. National Stage Application of PCT/CA2018/051399 filed Nov. 6, 2018 and claims the benefit of the filing date of Application No. 62/581,964, filed Nov. 6, 2017, the contents of each of which are incorporated herein by reference in their entirety.

FIELD

The invention relates to compounds that bind guanine quadruplexes and the synthesis thereof. Such compounds interteres with telomeric function, which may allow for treatment to disrupt or prevent cancer or HIV.

BACKGROUND

Although DNA is mostly found in a double-stranded format known as "B form duplex" other conformations and self-assembled forms of DNA also exist at least transiently in cells. Examples of instances when such non-duplex DNA conformations exist include DNA repair events, or DNA polymerase action or that of other biocatalysts.

Such conformations are emerging as key factors in the regulation of essential processes. Such processes include replication, transcription, and recombination. These processes are involved in cell division and proliferation, protein production, and DNA repair, respectively. In particular, guanine bases are able to form a substantially planar, hydrogen-bonded cyclic structure (i.e., guanine quartet, see FIG. 1), which is stabilized by the presence of a cation such as $Na^+$ or $K^+$. Such guanine quartets stack on top of each other in a helical fashion with grooves delineated by the DNA backbone, thus forming guanine quadruplexes ("G4s", see FIG. 1).

Despite falling under the same generic name, guanine quadruplexes are diverse. Their structures vary depending on: number of stacks; number of individual strands involved in an overall architecture; orientation of the strands with respect to each other; and loops. Overall, the number of combinations to form G4s is infinite. See FIG. 1 for a depiction of different strand orientations, leading to parallel (all same direction), antiparallel (alternating directions), and hybrid (3 up+1 down, or vice versa) topologies.

G4s can also occur in RNA. The formation of such ribose-based RNA structures can modulate the translation of a given gene, thereby offering further regulation of processes such as protein production. RNA-based G4 structures have actually been found to be more stable than DNA-based G4, to the point where two stacks of guanine quartets belonging to RNA are enough to form a stable G4. However, the diversity of RNA-based G4 seems to be more limited, as experiments point to parallel topologies being by far the most frequently observed with RNA due to the structural constraints imposed by the ribose-phosphate backbone. Additional structural diversity is also achieved in cases where DNA and RNA strands mix together to form guanine quadruplexes bearing both ribose and deoxyribose sugars.

G4 research has been a focus since it was proposed that guanine quadruplexes could play a role in regulating ageing in cancer cells, perhaps through their presence at the end of a chromosome (i.e, guanine-rich telomere region). From a functional perspective, it is noted that G4 have also been shown to form in the promoter region of oncogenic DNA. The presence of G4 in these regions alters the production of oncogenic proteins that play roles in all aspects of cancer, from cancer initiation, to proliferation, to enhancing nutrient influx through angiogenesis, and to metastasis. Furthermore, molecules targeting G4s in RNA may have the potential to silence such oncogenes without having to act on DNA. By controlling the formation of these structures in DNA and/or RNA, it may be possible to affect cancer initiation and progression. There is consequently interest in targeting G4 in both DNA and RNA.

A number of diseases other than cancer have now also been correlated with G4 formation. Not surprisingly, RNA transcripts of functional genes other than oncogenes also harbor G clusters. This is particularly important when these G clusters are repeated ('G-rich repeats'), as such repetitions complicate the function and compromise the accuracy of polymerases, and the inflation of the number of repeats may then be correlated with conditions such as neurological disorders (e.g., Fragile X Syndrome). Viral RNA sequences have also been found to carry G clusters that form G4s. These G4s become important elements in regulating the translation of viral RNA to infective proteins (e.g., Zika virus), but are also found after the viral RNA is integrated into the host DNA, which in turn is used by the host nuclear machinery to produce infective proteins, sometimes under the control of a G4-DNA regulatory element.

Guanine quadruplex targeting has broad applications in pharmaceutics. For example, protection against HIV is a possible application for a guanine quadruplex binder, as well as regulation of other genes that are linked to diseases through targeting of their promoters. For these reasons, targeting G4 has become a major field in health research. The current strategies for targeting G4 are two-fold: (i) use a relatively planar, mostly aromatic platform that stacks on top of a guanine quadruplex; and (ii) target the grooves of G4 with hydrophobic units that can interact with the sugar-phosphate backbone and/or the outer edges of the guanines through hydrogen-bonding or other noncovalent binding modes. However, G4s are dynamic and transient architectures present in very low number in a tremendous excess of duplex DNA and other RNA conformations. There is therefore a need for G4 binders that have low affinity for duplex DNA.

SUMMARY

In one aspect, the invention provides a compound that has general formula (1):

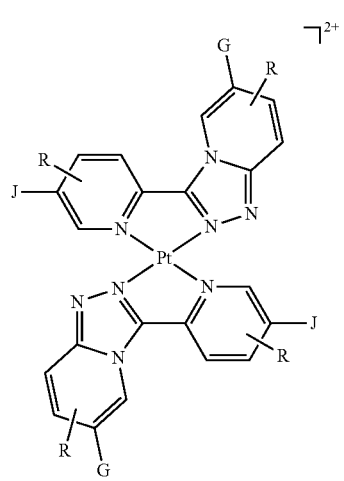

(1)

or a salt or prodrug thereof, wherein

G and J are independently a moiety selected from hydrogen, amino, alkyl, alkenyl, alkynyl, halo, amido, aryl (which includes heteroaryl), hydroxyl, ether, carboxyl, ester, boryl, or a combination thereof;

R is independently H, halo, aliphatic, alkyl, alkenyl, alkynyl, amido, amino, hydroxyl, ester, ether, aryl (which includes heteroaryl), carboxyl or a combination thereof.

In one embodiment, the compound binds to a guanine quadruplex. In one embodiment, the compound binds a guanine quadruplex of DNA, RNA, or a combination of DNA and RNA. In one embodiment, the guanine quadruplex is of SEQ ID NO: 1 to 12, or a portion thereof.

In one embodiment, the guanine quadruplex is located at a telomere or at a gene promoter. In one embodiment, the compound of Formula (1) comprises compounds (shown in Table 1) $Pt(2)_2$, $Pt(4)_2$, $Pt(6)_2$, $Pt(7)_2$, $Pt(8)_2$, $Pt(10)_2$, $Pt(11)_2$, $Pt(15)_2$, $Pt(16)_2$, $Pt(17)_2$, $Pt(18)_2$, $Pt(19)_2$, $Pt(21)_2$, $Pt(23)_2$, $Pt(2)(4)$, or a salt or prodrug thereof. In one embodiment, the compound has triflate counterions. In one embodiment, the compound has $PF_6$ counterions. In one embodiment, the compound has halide counterions. In one embodiment, the compound has telomerase inhibiting activity (e.g., interteres with telomeric functions), or inhibits expression of an oncogene.

In one aspect, the invention provides a pharmaceutical composition comprising an effective amount of a compound of formula (1), or a pharmaceutically acceptable salt thereof, and a pharmaceutically acceptable excipient. In one embodiment of the pharmaceutical composition aspect, the compound has anticancer, anti-infective or neuroprotective activity. In one embodiment, the pharmaceutical composition further comprising active ingredients of other medicaments. In one embodiment, the pharmaceutical composition further comprises a protein or a glycosaminoglycan. In one embodiment, the glycosaminoglycan is hyaluronic acid. In one embodiment, the protein is an antibody, hemoglobin, alphafeto-protein, fibrinogen, or serum albumin.

In one aspect, the invention provides a method of treating a disease, comprising administering to a mammal in need thereof an effective amount of a compound of formula (1), or a pharmaceutically acceptable salt or prodrug thereof. In one embodiment, the disease is cancer, genetic disease, neurodegenerative disease, or infection. In one embodiment, the disease is selected from neurological disorders, Fragile X syndrome, amyotrophic lateral sclerosis, frontotemporal dementia, spinocerebellar ataxia type 36, schizophrenia, autism, Parkinson's disease, Alzheimer's disease, infectious diseases caused by bacteria, protozoa and viruses such as HIV virus, Zika virus, human herpes simplex-1 virus, Epstein-Barr virus (human Herpes virus 4), Kaposi's sarcoma associated herpes virus, Ebola virus, *Clostridium difficile* bacterium, *Neisseria gonorrhoeae* bacterium (gonorrhea), *Plasmodium falciparum* protozoan parasite (malaria), *Trypanosoma brucei* parasite (sleeping sickness), *Neisseria meningitidis* bacterium (meningococcus) or spirochetes *Borrelia* bacterium (Lyme disease).

In one aspect, the invention provides a method of detection, comprising adding an imaging agent (e.g., fluorophore, radionucleotide, luminescent or phosphorescent tracer) and a compound of formula (1) to a sample, and determining the amount of signal from the imagining agent.

In one aspect, the invention provides a method of detection, comprising a compound of formula (1) with intrinsic fluorescent properties to a sample, and determining the amount of fluorescence. In one embodiment, the method detects presence or absence of a guanine quadruplex in the sample. In one embodiment, the method of detection is for use in affinity determination. In one embodiment, the affinity determination is Fluorescence Indicator Displacement (FID). In other embodiments, the affinity determination is imaging, detection and/or diagnostics.

In one aspect the invention provides a method of binding a guanine quadruplex or fragment thereof, comprising adding a compound of formula (1) to a sample that comprises a guanine quadruplex.

In one aspect, the invention provides compounds selected from 6, 8, 9, 10, 11, 21 and 23 as shown in the Working Examples and described herein.

BRIEF DESCRIPTION OF THE DRAWINGS

For a better understanding of the invention and to show more clearly how it may be carried into effect, reference will now be made by way of example to the accompanying drawings, wherein.

DETAILED DESCRIPTION

Definitions

Figure 1:
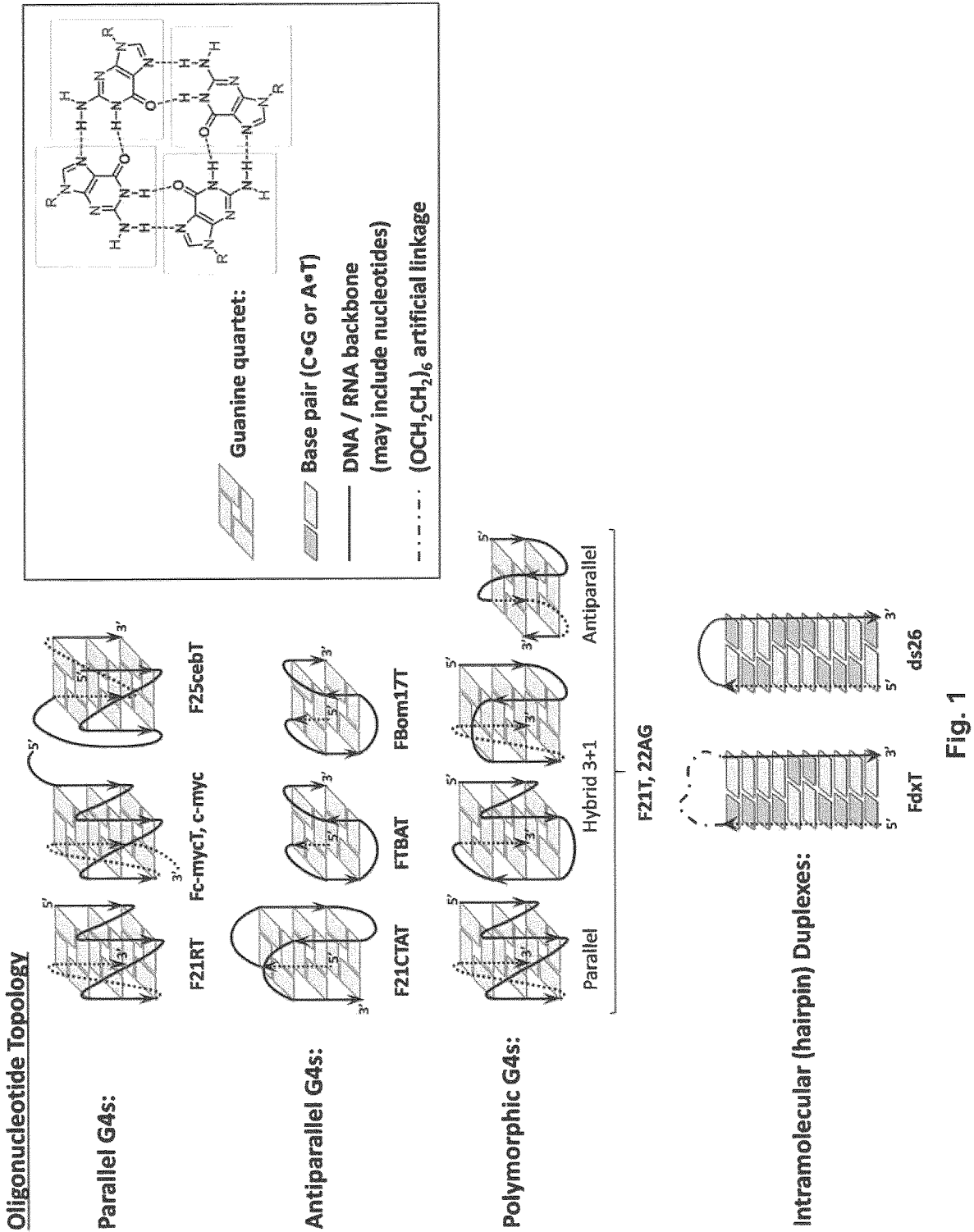
FIG. 1 shows a schematic of the structures of oligonucleotides discussed herein, notably guanine quadruplexes and duplexes in different conformations.

As used herein the term "aliphatic" includes alkanyl, alkenyl and alkynyl moieties. An aliphatic group may be substituted or unsubstituted. It may be straight chain, branched chain or cyclic.

As used herein the term "aryl" includes aromatic carbocycles and aromatic heterocycles, and may be substituted or unsubstituted.

As used herein, the term "unsubstituted" refers to any open valence of an atom being occupied by hydrogen. Also, if an occupant of an open valence position on an atom is not specified then it is hydrogen.

As used herein "substituted" refers to the structure having one or more substituents.

As used herein "heteroatom" means a non-carbon, non-hydrogen atom. In some cases, a heteroatom may have a lone pair of electrons available to form dative or coordinate bonds (e.g., N, O, P).

As used herein, the term "FID" refers to fluorescence indicator displacement, which is also known as fluorescence intercalator displacement.

As used herein, the term "FRET" refers to fluorescence resonance energy transfer, which is also known as 'Förster resonance energy transfer'.

As used herein, the term "F21T" refers to an oligonucleotide functionalized at its 3' and 5' ends with fluorophores that can exchange energy through FRET. The first of the two fluorophores is fam (6-carboxyfluorescein). The second of the two fluorophore is tamra (a derivative of rhodamine). The F21T sequence without fluorophores is called 21ag (see FIG. 1).

EMBODIMENTS

As described above, it is desirable to have a binder of guanine quadruplexes that has a low affinity for duplex DNA. Such a binder is provided herein together with derivatives thereof, and their binding affinity for quadruplexes has been quantified. The binder and derivatives thereof have been shown to be selective to guanine quadruplexes in buffers. Unlike other such platforms, this compound does not require extension of its insoluble aromatic unit to avoid association with duplex DNA and does not require the introduction of water solubilizing chains. The generic chemical structure of this compound is indicated in the below Formula (1):

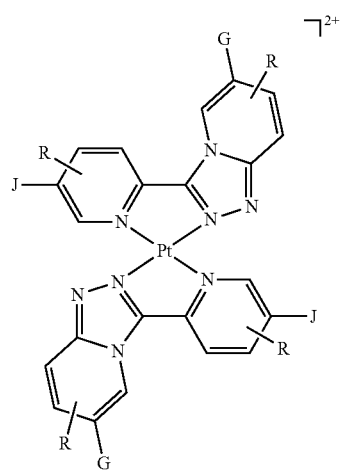

or a salt or prodrug thereof, wherein G and J are independently a moiety selected from hydrogen, amino, alkyl, alkenyl, alkynyl, halo, amido, aryl (which includes heteroaryl), hydroxyl, ether, carboxyl, ester, boryl, or a combination thereof, and R is independently H, halo, aliphatic alkyl, alkenyl, alkynyl, aryl, amido, amino, hydroxyl, carboxyl, esters thereof, ethers thereof, or a combination thereof.

Representative examples of formula (1) are presented in Table 1 together with a simple name for use herein. Such compounds include $Pt(2)_2$, $Pt(4)_2$, $Pt(6)_2$, $Pt(7)_2$, $Pt(8)_2$, $Pt(10)_2$, $Pt(11)_2$, $Pt(15)_2$, $Pt(16)_2$, $Pt(17)_2$, $Pt(18)_2$, $Pt(19)_2$, $Pt(21)_2$, $Pt(23)_2$, $Pt(2)(4)$, For comparison, a standard G4 binder is also tested in studies herein; it is known as Phen-DC3 (commercially available from Polysciences Inc., located in Warrington, Pa., USA, and from MedChem Express, located in Monmouth Junction, N.J., USA) and its structure is also shown in Table 1.

Certain compounds of Formula (1) that appear in Table 1 include one or more substituents that can provide characteristics other than water solubility or prevention of duplex intercalation. These moieties may act as quadruplex groove binding elements (e.g., $Pt(19)_2$, $Pt(23)_2$). For example, such moieties can differentiate between various G4 topologies, and therefore potentially address individual G4 sites such as telomeres, oncogene promoters, or RNA loci.

The binders of Formula (1) with the exception of $Pt(6)_2$ have been shown to strongly stabilize guanine quadruplexes at low concentrations. In potassium buffers, all binders studied display good selectivity for quadruplex over duplex DNA. In sodium buffers, $Pt(7)_2$, $Pt(8)_2$, and $Pt(11)_2$ remain selective for quadruplex over duplex DNA. Functionalization of the two different aromatic moieties at 5 and 5' positions (see Example 1) has been shown to promote selectivity for different topologies of human telomeric 22AG in potassium. Specifically, the binders $Pt(4)_2$, $Pt(7)_2$, $Pt(8)_2$, $Pt(10)_2$, and $Pt(11)_2$, and to a lesser extent $Pt(18)_2$ and $Pt(19)_2$, preferentially bind to the antiparallel topology of 22AG, while $Pt(2)_2$, $Pt(15)_2$, $Pt(16)_2$, and $Pt(17)_2$ preferentially bind to a hybrid topology. The interactions of several binders with 22AG have been quantified, and the binding affinities found to fall into the same range as Phen-DC3, a high-performing reference compound. Based on these results, the functionalization of the $Pt(2)_2$ aromatic platform does not interfere with binding; the binding affinity of the novel binders for 22AG can be ranked as $Pt(2)_2 < Pt(11)_2 \approx Pt$ $(8)_2 \approx Pt(7)_2$. Finally, the triflate and/or $PF_6$ salts of $Pt(2)_2$, $Pt(8)_2$, and $Pt(11)_2$ have been shown to inhibit cell growth in five human tumour cell lines.

Referring to the figures, results are shown that quantify the ability of compounds of Formula (1) to bind and/or stabilize oligonucleotide G4 or duplex architectures.

Referring to FIG. 1, a schematic is provided that depicts several different topologies of guanine quadruplexes.

Figure 2A:
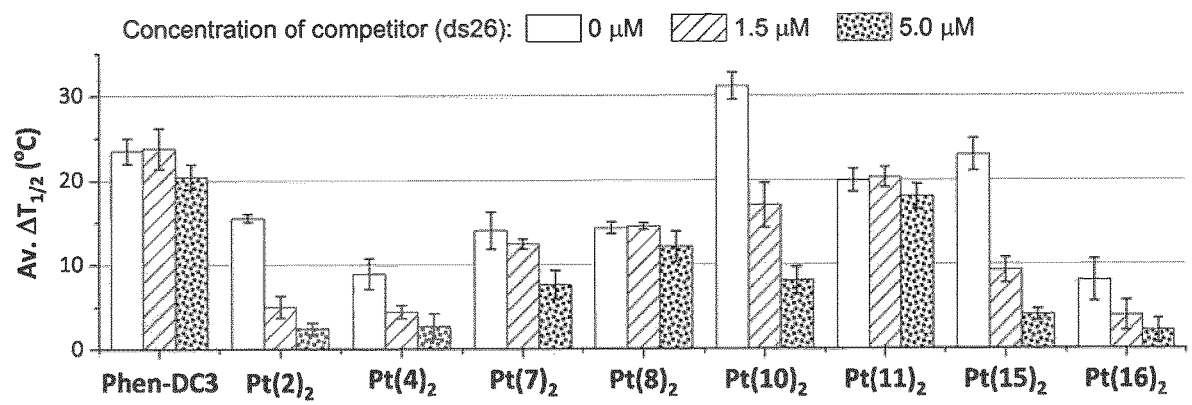
FIG. 2A graphically presents Förster Resonance Energy Transfer (FRET) results of a competition assay between G4 and duplex for specified binder (0.2 microM) in sodium buffer.
Figure 2B:
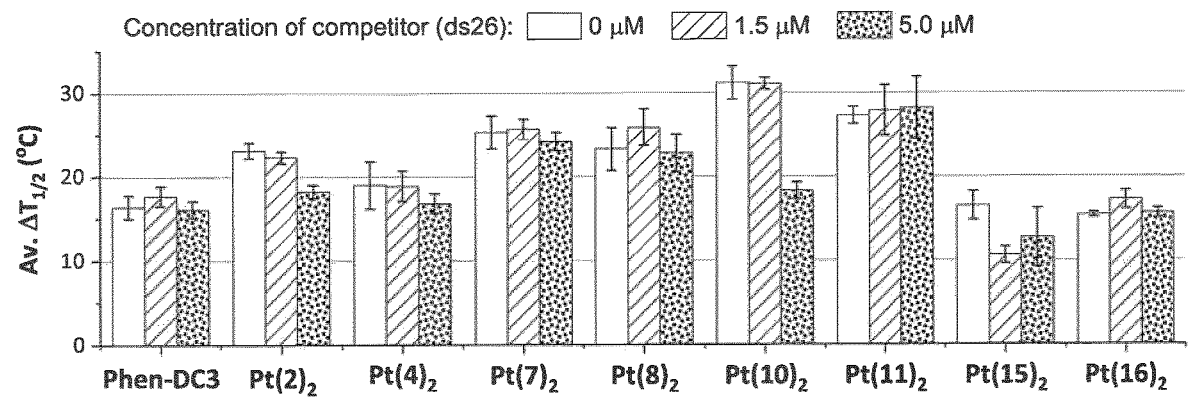
FIG. 2B graphically presents FRET results of a competition assay between G4 and duplex for specified binder (0.2 microM) in potassium buffer.

Referring to FIGS. 2A and 2B, a bar graph is presented that shows FRET results of a competition assay for binders as specified (see Table 1 for structural formulae) between G4 and duplex in sodium or potassium buffers as indicated. Novel binders were studied as dihalide salts (e.g., dichloride). Specifically, in FIGS. 2A and 2B, FRET competition assays were conducted in sodium buffer (10 mM lithium cacodylate buffer (pH 7.2) and 100 mM NaCl) or potassium buffer (10 mM lithium cacodylate buffer (pH 7.2) and 10 mM KCl/90 mM LiCl). The G4 used was F21T (0.1 µM) and ds26 (0, 1.5 or 5.0 µM, as indicated) was used as a silent (i.e., non-fluorescent) duplex competitor. Error bars represent standard deviation. In cases where $\Delta T_{1/2}$ is underestimated, changes in $\Delta T_{1/2}$ upon addition of competitor were confirmed by visual assessment of melting curves.

Although not wishing to be bound by theory, the inventors suggest that where stabilization was reduced upon addition of increasing amounts of duplex, the binder was interacting with both duplex and quadruplex and is therefore not selective. In cases where stabilization was maintained in the presence of the duplex DNA, the binder was selective for the quadruplex. Notably, selectivity for G4 of the binders described herein was good, particularly in the presence of potassium.

A similar FRET competition undertaken with $Pt(2)_2$ and F21T (0.2 µM) showed a loss of stabilization of F21T upon addition of increasing amounts of unlabeled competitor quadruplexes c-myc (0-50 equivalents), thereby confirming that the binder interacts with the quadruplex itself rather than with the FAM and/or TAMRA fluorophores.

Figure 3A:
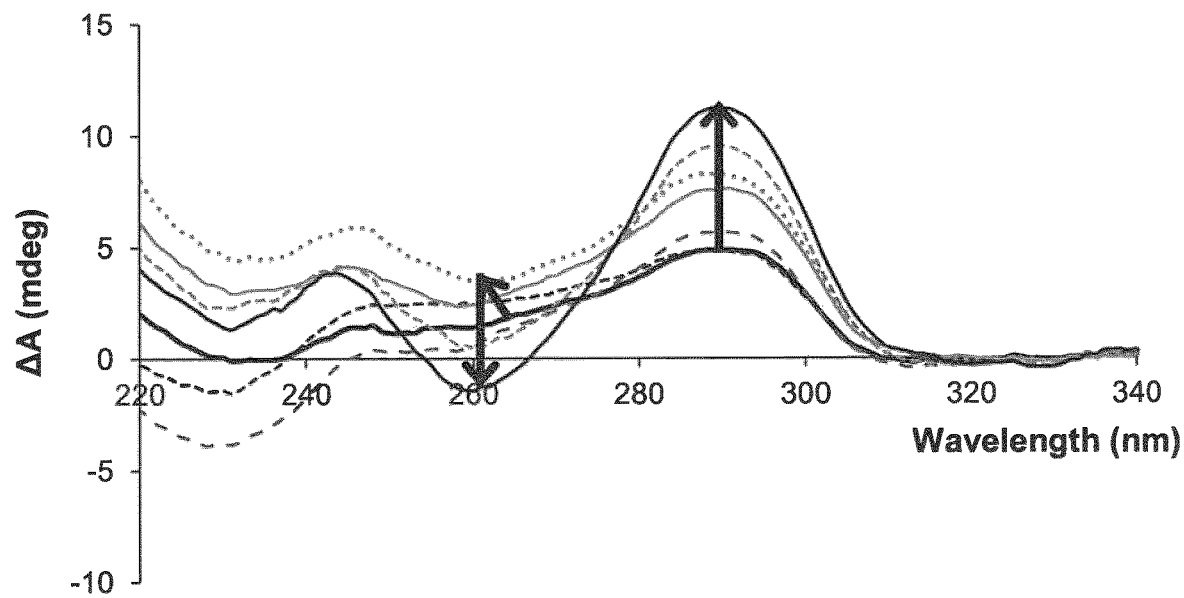
FIGS. 3A and 3B show circular dichroism (CD) spectra of two quadruplexes (22AG and c-myc respectively) in $K^+$ buffer, in the absence of binder and in the presence of several different concentrations of binder (namely $Pt(11)_2$).
Figure 3B:
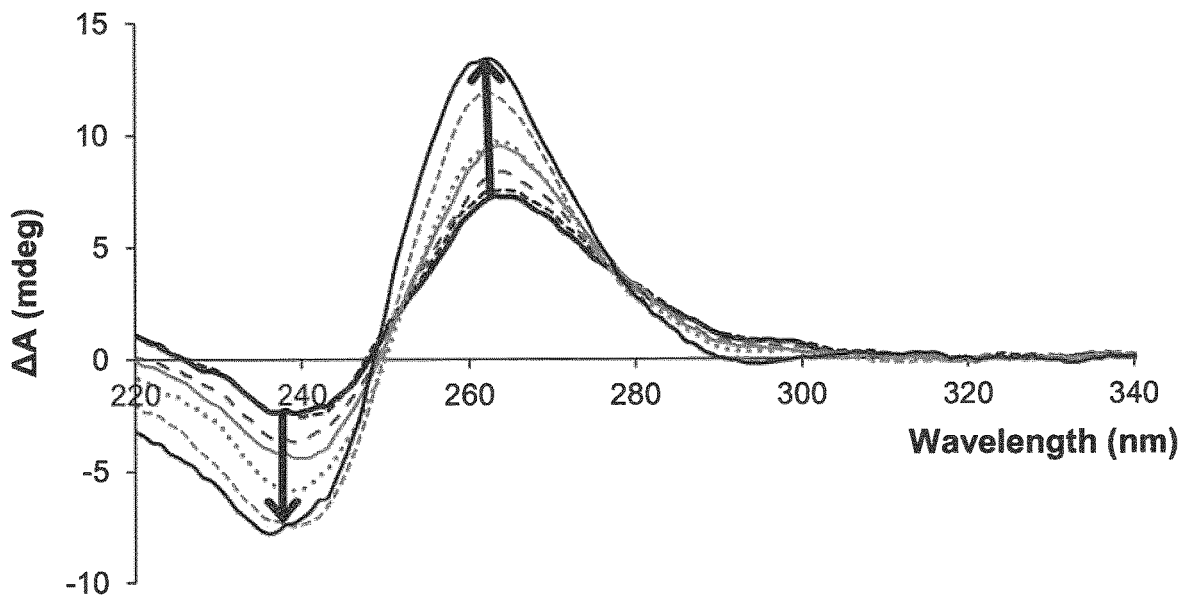

Referring to FIGS. 3A and 3B, representative CD spectra from titrations where binders are added to A) 22AG and B) c-myc in potassium buffer (10 mM lithium cacodylate buffer (pH 7.2) and 100 mM KCl) are provided. Specifically, these graphs show changes in $\Delta$ A upon addition of $Pt(11)_2$ (0-5 equivalents). Such experiments were performed for all novel binders of Formula (1) described in Table 1 with the exception of $Pt(6)_2$.

Although not wishing to be bound by theory, the inventors suggest that changes in the magnitude of peaks can be caused by binding of small molecules to the quadruplex, while changes in the maximum wavelength of major peaks, or disappearances and/or appearances of major peaks, provide information about the quadruplex topology and any binder-induced conformational changes which may occur. The latter phenomenon is of particular interest in the case of the polymorphic quadruplex 22AG, which can adopt parallel, hybrid, and/or antiparallel topologies. In the example of FIGS. 3A and 3B, changes in peak magnitude are consistent with the binding of $Pt(11)_2$ to 22AG and c-myc respectively. The interactions of all novel binders of Formula (1) except $Pt(6)_2$ (see Table 1) with 22AG and c-myc have been confirmed through similar CD titrations. In FIG. 3A, spectral changes such as the appearance of a peak at 260 nm are consistent with a conformational change from a hybrid to an antiparallel 22AG quadruplex (Randazzo et al, *Top. Curr. Chem.* (2013) 330: 67-86). This conformational change is strongly induced by addition of $Pt(4)_2$, $Pt(7)_2$, $Pt(8)_2$, $Pt(10)_2$, and $Pt(11)_2$, and to a lesser extent by addition of $Pt(18)_2$ and $Pt(19)_2$. The hybrid topology of 22AG is conserved and no conformational changes are observed upon addition of $Pt(2)_2$, $Pt(15)_2$, $Pt(16)_2$, and $Pt(17)_2$. These results suggest that functionalization of different sites (e.g., 5 and 5', see Example 1) on the aromatic platform of the binder may promote selectivity towards different quadruplex topologies.

Figure 4A:
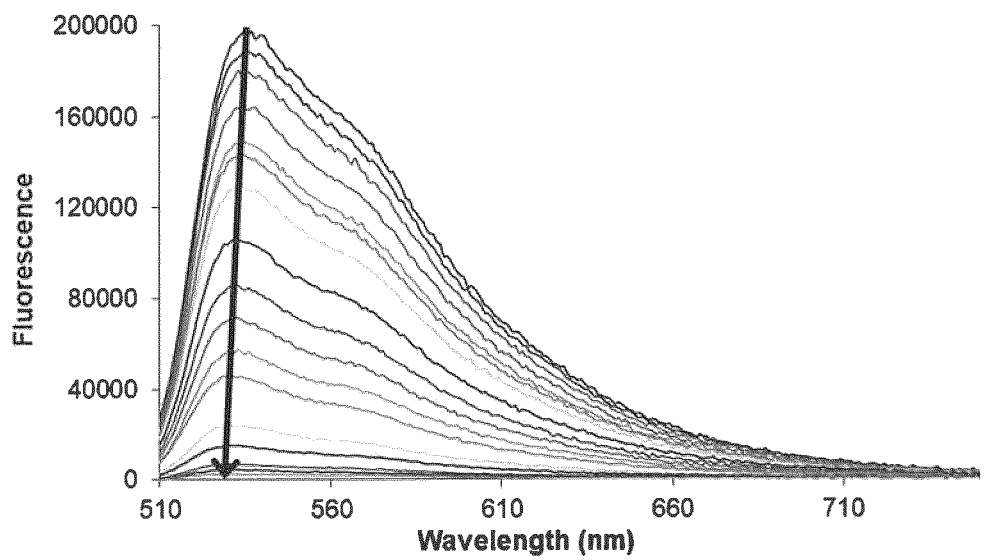
FIG. 4A graphically presents diminishing fluorescence intensity of fluorophore-quadruplex complex, due to displacement of fluorophore by binder.
Figure 4B:
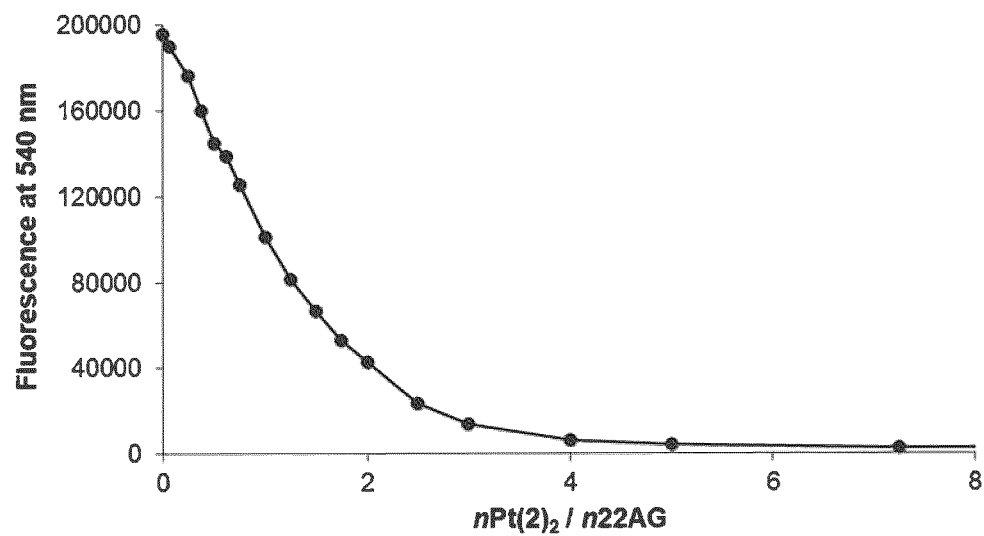
FIG. 4B shows the fluorescence intensity decay of the fluorophore-quadruplex complex at 540 nm relative to the ratio of [binder]/[quadruplex] from the spectra of FIG. 4A.

Referring to FIGS. 4A and 4B, examples of spectral information which can be obtained by FID titrations are displayed. Specifically, such titrations involve the addition of a binder to a thiazole orange (TO):22AG complex (0.25 or 0.5 µM DNA) in potassium buffer (10 mM lithium cacodylate buffer (pH 7.2) and 100 mM KCl). FIG. 4A provides an example of the blank-, baseline-, and volume-corrected fluorescence spectra obtained from the titration of $Pt(2)_2$ with TO-22AG. FIG. 4B displays the fluorescence at a particular emission wavelength (e.g., 540 nm) as a function of the molar ratio of binder ($Pt(2)_2$) to quadruplex (22AG). Previous experiments indicate that the fluorophore binds to the quadruplex in a 1:1 TO:22AG stoichiometry, thus potentially leaving a second binding site unoccupied on the other terminal guanine tetrad of 22AG. Although not wishing to be bound by theory, the inventors suggest that the fluorescence signal can be correlated to the concentrations of (i) the initial thiazole orange-22AG complex, as well as (ii) any complexes which may form if the binder first occupies the second, free binding site, thereby not displacing the fluorophore. Data fitting of such experiments with 22AG and specified binders (Phen-DC3, $Pt(2)_2$, $Pt(7)_2$, $Pt(8)_2$, and $Pt(11)_2$) has allowed for the determination of binding constants and of binder:G4 complex stoichiometries (see Table 4).

Figure 4C:
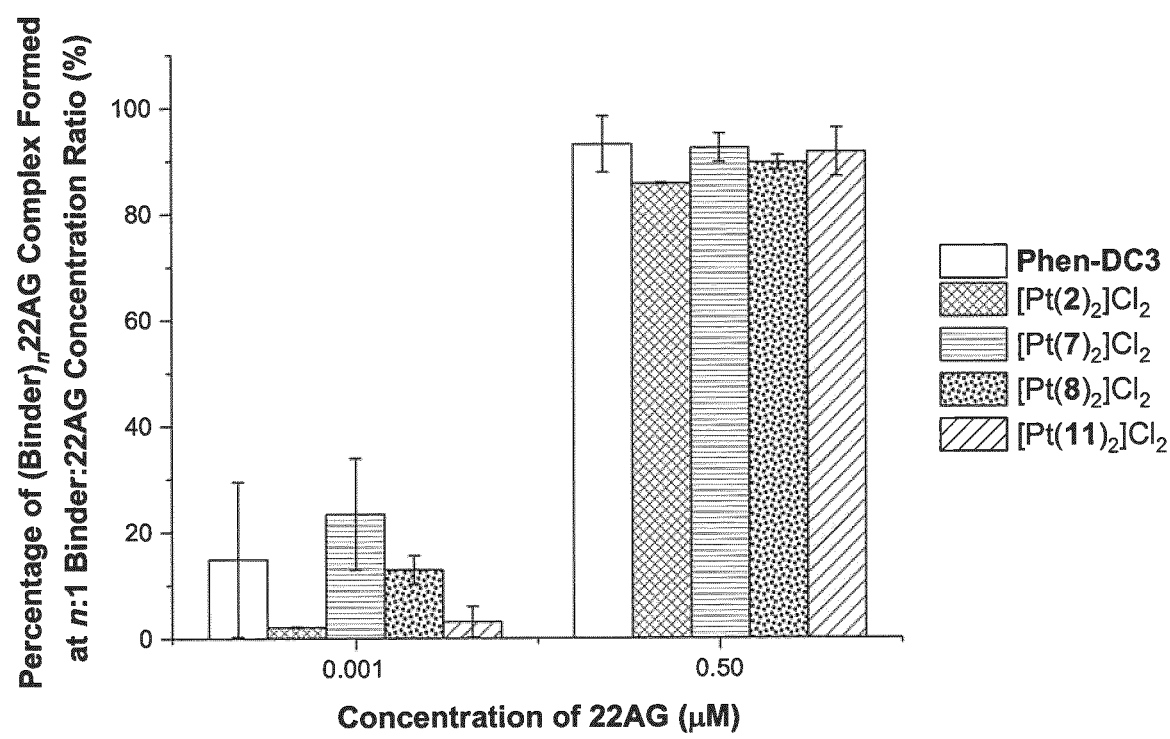
FIG. 4C graphically presents the predicted percentage of $(binder)_nG4$ complex formed after displacement of the fluorophore (where n=1 or 2 as determined by data fitting) at a concentration of binder corresponding to n equivalents relative to the concentration of the quadruplex.

Referring to FIG. 4C, a bar graph is presented that shows the percentage of binder:G4 complex predicted to form at a given concentration of 22AG (1.0 nm or 0.5 µM). Predictions are generated using HySS modelling software and the experimentally determined binding constants and complex stoichiometries. Error bars represent the standard deviation between the percentage of complex formed at the high and low error limits of each binding constant. To allow for comparisons between complexes of 2:1 binder:G4 stoichiometry (Phen-DC3, $Pt(2)_2$, and $Pt(11)_2$) and 1:1 binder:G4 stoichiometry ($Pt(7)_2$ and $Pt(8)_2$), the percentage of complex formed is calculated at the concentration of binder that would produce the same binder:G4 molar ratio as that given by the complex stoichiometry. For more details, see Table 4.

Figure 5:
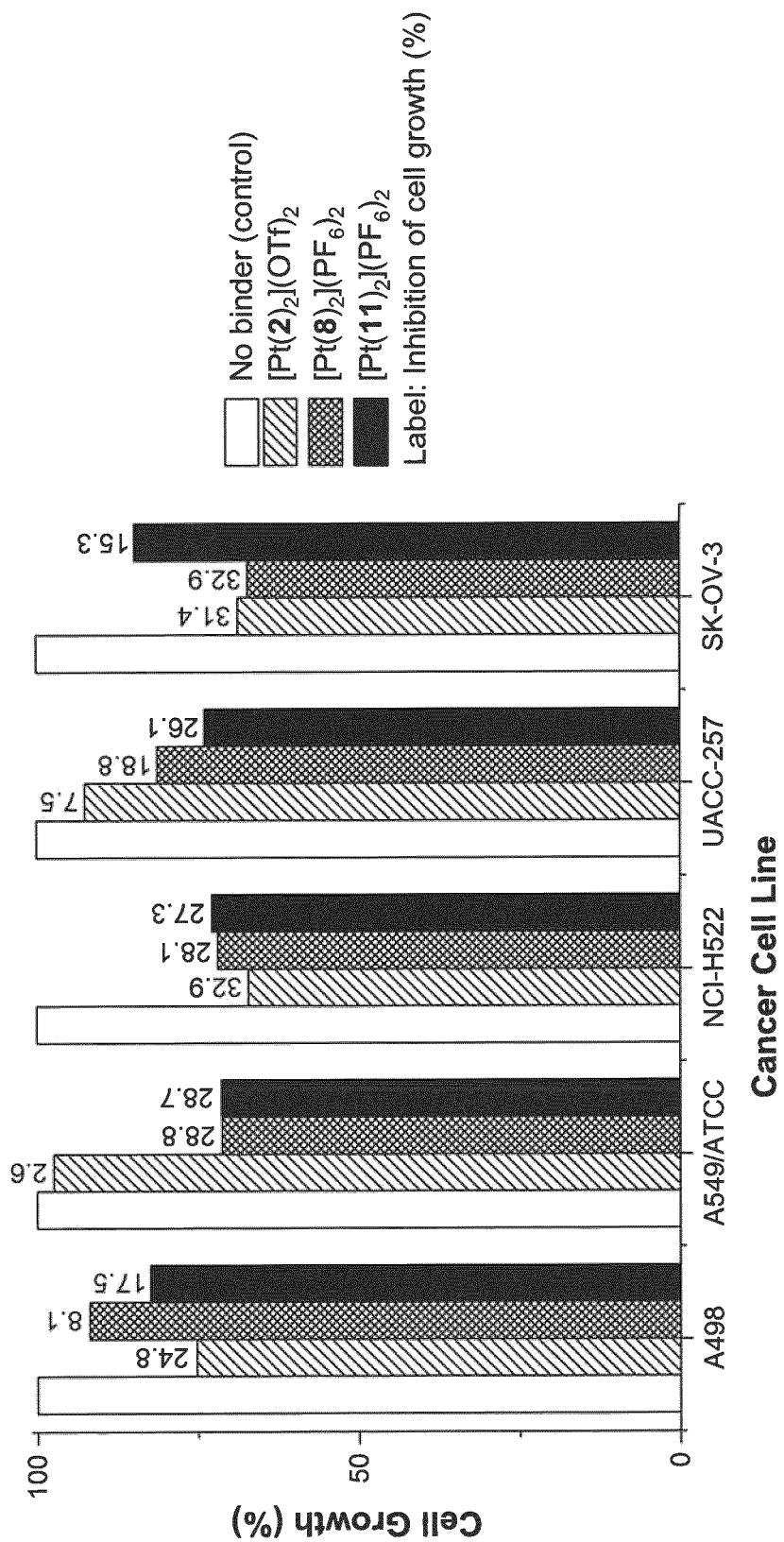
FIG. 5 graphically presents the percentage by which the growth of five cancer cell lines are inhibited due to the presence of a binder (namely $Pt(2)_2$, $Pt(8)_2$, or $Pt(11)_2$) at a concentration of 10 microM.

Referring to FIG. 5, a bar graph is presented that shows the percentage of growth inhibition exhibited by five cancer cell lines from the NCI-60 screen (A498, A549/ATCC, NCI-H522, UACC-257, SK-OV-3; see Table 5) in the presence of 10 µM of $Pt(2)_2$, $Pt(8)_2$, and $Pt(11)_2$. Notably, the binders used are the complexes formulated with triflate and/or $PF_6$ counterions. The five cell lines experience reduction in growth (8-33%) after chemical treatment with these G4 binders as sole agents. The functionalized complexes ($Pt(8)_2$ and $Pt(11)_2$) perform equally well with the two non-small cell lung cancer cell lines A549/ATCC and NCI-H522 (growth inhibition 30%). While $Pt(2)_2$ performs similarly to $Pt(8)_2$ and $Pt(11)_2$ in NCI-H522 cells, it has little effect on A549/ATCC cells. Growth inhibition of melanoma cancer cell line UACC-257 is enhanced by functionalization of the platform ($Pt(2)_2$ shows a weaker effect than $Pt(8)_2$ and $Pt(11)_2$), while functionalization does not increase potency of growth inhibition in kidney cancer cell line A498 and ovarian cancer cell line SK-OV-3, where all three complexes have a significant effect.

Referring to Table 1, structural formulae for compounds of Formula (1) are provided together with short names for use herein. The structure of PhenDC3 standard is also provided.

Referring to Table 2, fluors, oligonucleotide sequences and corresponding SEQ ID numbers are presented that were used in FRET melting temperature, CD, and/or FID experiments. Such experiments are described in Examples 2, 3, and 4, respectively.

Referring to Table 3, data is presented that shows change in melting temperature for duplex or one of several G4 topologies in the presence of certain binders of Formula (1), as measured by FRET (0.2 μM binder and 0.1 μM oligonucleotide in $K^+$ buffer), with reference to PhenDC3 standard. All samples tested are guanine quadruplexes except FdxT, which is in duplex form. Binding of G4s by the specified binders of Formula (1) was shown. In the case of $Pt(6)_2$, binding was minimal. In the case of most of the other invented binders, the data shows that the invented platform is so efficient in stabilizing the G4 that melting is no longer achievable within experimental parameters for most oligonucleotides studied, and hence FRET melting experiments only provide underestimated stabilization values ($\Delta T_{1/2}$).

Referring to Table 4, data is presented for association constants of compounds of Formula (1) and the 22AG quadruplex in potassium buffer as determined by FID titration and data fitting. The percentage of complex formed at 0.5 μM 22AG and at a concentration of binder which produces a molar ratio equivalent to the final binder:G4 complex stoichiometry (2:1 or 1:1) determined through data fitting, as predicted using HySS software, is also included.

Although not wishing to be bound by theory, the inventors suggest that the experimentally determined binding constants show that (i) the novel G4 binders of Formula (1) listed in Table 4 bind to 22AG with affinity that is comparable to that of the reference binder Phen-DC3, and (ii) functionalization of the aromatic platform of $Pt(2)_2$ enhances its binding affinity in the case of all binders studied. Based on these results and subsequent HySS modelling of species distribution curves at different concentrations of G4 (see example in Table 4 and FIG. 4C), the binding affinity of the novel binders for 22AG can be ranked as $Pt(2)_2 < Pt(11)_2 \approx Pt(8)_2 \approx Pt(7)_2$.

Referring to Table 5, a complete list of cancer cell lines used in the NIH-60 cytotoxicity screening is presented. Five cell lines where proliferation was inhibited by 8-33% in the presence of one of the tested binders at a concentration of 10 μM are also highlighted.

Other diseases with which quadruplexes are associated include: neurological disorders, (including, but not limited to, Fragile X syndrome, amyotrophic lateral sclerosis, frontotemporal dementia, spinocerebellar ataxia type 36, schizophrenia, autism, Parkinson's and Alzheimer's diseases); and infectious diseases caused by bacteria, protozoa and viruses (including infections such as HIV virus, Zika virus, human herpes simplex-1 virus, Epstein-Barr virus (human Herpes virus 4), Kaposi's sarcoma associated herpes virus, Ebola virus, *Clostridium difficile* bacterium, *Neisseria gonorrhoeae* bacterium (i.e., gonorrhea), *Plasmodium falciparum* protozoan parasite (i.e., malaria), *Trypanosoma brucei* parasite (i.e., sleeping sickness), *Neisseria meningitidis* bacterium (i.e., meningococcus) and spirochetes *Borrelia* bacterium (i.e., Lyme disease).

In some embodiments of combination therapy for the treatment of a disease, a first compound is a compound of Formula (1). In other embodiments, the second compound is an antineoplastic, antiinfective or neuroprotectant agent that is not of Formula (1). Known antineoplastic agents that may be suitable in a combination therapy according to the invention include, but are not limited to anthracyclines (e.g., doxorubicin, daunorubicin), other antibiotic agents (e.g, the HSP90 inhibitor 17-AAG), *Vinca* alkaloids (e.g., vinblastine, vincristine), epipodophyllotoxins (e.g., etoposide, teniposide), pyrimidine analogs (e.g., gemcitabine, 5-fluorouracil, cytarabine), taxanes (e.g., paclitaxel), platinum-based cancer drugs (e.g., cisplatin), monoclonal antibodies (e.g., TZ/Herceptin), and equivalents thereof.

Compounds of the invention can be formulated to ensure proper distribution in vivo. For example, therapeutic compounds of the invention can be formulated in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., Ranade, V. V. *J. Clin. Pharmacol.* (1989) 29(8):685-94). Exemplary targeting moieties include folate and biotin (see, e.g., U.S. Pat. No. 5,416,016 to Low et al.); mannosides (Umezawa et al., *Biochem. Biophys. Res. Commun.* (1988) 153(3): 1038-44; antibodies (Bloeman et al., *FEBS Lett.* (1995) 357:140; Owais et al., *Antimicrob. Agents Chemother.* (1995) 39(1):180-4); and surfactant protein A receptor (Briscoe et al., *Am. J. Physiol.* (1995) 268(3 Pt 1): L374-80). Liposomal formulations of telemerase inhibitors may include a targeting moiety.

Techniques that are used for cell nucleus targeting therapeutics are described in Pan, L. et al., *Chem. Soc. Rev.* 2018, 47: 6930 and Deepthi, A, et al., *J. Pharm Sci. & Res.* 2013, 5(2): 48-56, which are hereby incorporated by reference in their entirety.

Delivery and in vivo distribution can also be affected by alteration of an anionic group of compounds of the invention. For example, anionic groups such as phosphonate, carboxylate, enol, or hydroxyl groups can be functionalized to provide compounds with desirable pharmacokinetic, pharmacodynamic, biodistributive, or other properties.

To administer a therapeutic compound by other than parenteral administration, it may be necessary to coat the compound with, or co-administer the compound with, a material to prevent its inactivation. For example, the therapeutic compound may be administered to a subject in an appropriate vehicle, for example, liposomes, or a diluent. Pharmaceutically acceptable diluents include saline and aqueous buffer solutions. Liposomes include water-in-oil-in-water CGF emulsions as well as conventional liposomes (Strejan et al., *Prog. Clin. Biol. Res.* (1984) 146: 429-34).

The therapeutic compound may also be administered ocularly, topically, intravaginally, as well as parenterally (e.g., intramuscularly, intravenously, intraperitoneally, intraspinally, intrathecally, or intracerebrally). Dispersions can be prepared in glycerol, liquid polyethylene glycols, and mixtures thereof and in oils. Under ordinary conditions of storage and use, these preparations may contain a preservative to prevent the growth of microorganisms. Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, liquid polyethylene glycol, and the like), suitable mixtures thereof, and oils (e.g. vegetable oil). The proper fluidity can be maintained, for example, by the use of a coating such as lecithin, by the maintenance of the required particle size in the case of dispersion, and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filter sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, methods of preparation include vacuum drying and freeze-drying which yield a powder of the active ingredient (i.e., the therapeutic compound) optionally plus any additional desired ingredient from a previously sterile-filtered solution thereof.

Solid dosage forms for oral administration include ingestible capsules, tablets, pills, lollipops, powders, granules, elixirs, suspensions, syrups, wafers, buccal tablets, troches, and the like. In such solid dosage forms the active compound is mixed with at least one inert, pharmaceutically acceptable excipient or diluent or assimilable edible vehicle such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof, or incorporated directly into the subject's diet. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The percentage of the therapeutic compound in the compositions and preparations may, of course, be varied. The amount of the therapeutic compound in such therapeutically useful compositions is such that a suitable dosage will be obtained.

The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut corn, germ olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Therapeutic compounds can be administered in time-release or depot form, to obtain sustained release of the therapeutic compounds over time. The therapeutic compounds of the invention can also be administered transdermally (e.g., by providing the therapeutic compound, with a suitable vehicle, in patch form).

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of neurological, infectious and cancerous conditions in subjects.

Therapeutic compounds according to the invention are administered at a therapeutically effective dosage sufficient to achieve the desired therapeutic effect, e.g. to prevent the spread of cancer and/or kill cancerous cells, reduce or eradicate infectious symptoms, or mitigate or eliminate neurological conditions. Actual dosage levels of active ingredients in the pharmaceutical compositions of this invention may be varied so as to obtain an amount of the active compound(s) that is effective to achieve and maintain the desired therapeutic response for a particular subject, composition, and mode of administration. The selected dosage level will depend upon the activity of the particular compound, the route of administration, frequency of administration, the severity of the condition being treated, the condition and prior medical history of the subject being treated, the age, sex, weight and genetic profile of the subject, and the ability of the therapeutic compound to produce the desired therapeutic effect in the subject. The dosage may also be adjusted when the invention is used in combination with other pharmaceutical or physical treatment such as radiation. Dosage regimens can be adjusted to provide the optimum therapeutic response. For example, several divided doses may be administered daily or the dose may be proportionally reduced as indicated by the exigencies of the therapeutic situation.

However, it is well known within the medical art how to determine the proper dose for a particular patient (e.g., mammal) by the dose titration method. In this method, the patient is started with a dose of the drug compound at a level lower than that required to achieve the desired therapeutic effect. The dose is then gradually increased until the desired effect is achieved. Starting dosage levels for an already commercially available therapeutic agent of the classes discussed above can be derived from the information already available on the dosages employed. Also, dosages are routinely determined through preclinical ADME toxicology studies and subsequent clinical trials as required by the FDA or equivalent agency. The ability of a G4 binder to produce the desired therapeutic effect may be demonstrated in various well known models for the various conditions treated with these therapeutic compounds.

In one embodiment, compounds of Formula (1) are useful as G4 binders for diagnostic tools (e.g. to detect viral DNA/RNA). G4 fragments related to a disease of interest, such as a viral G4 in the RNA pool or in the DNA of a potential patient, may be identified thanks to compounds of Formula (1) through direct or indirect (e.g. FID) fluorescence, absorbance, mass, redox, electrophoretic and/or magnetic properties.

The following working examples further illustrate the present invention and are not intended to be limiting in any respect.

WORKING EXAMPLES

Methods and Materials

Commercially available reagents were used as received. Of these, cacodylic acid (98%) was obtained from Acros. Acetyl chloride, ammonium chloride, ammonium hexafluorophosphate (99%), [bis(trifluoroacetoxy)iodo]benzene (PIFA), 2-bromoethanol, 2-bromo-5-nitropyridine, 2-(bromoethoxy)-tert-butyldimethylsilane (98%, stabilized with sodium carbonate), di-isopropylethylamine, 4-dimethylaminopyridine (DMAP), copper(I) iodide (98%), N,N-dimethylethylene diamine, di-tert-butyl dicarbonate, hydrazine hydrate (98%), lithium chloride, sodium ascorbate (L-ascorbic acid sodium salt), tetra-N-butylammonium fluoride, tin (II) chloride dihydrate, trifluoroacetic acid (TFA), and trimethylsilylacetylene were purchased from Alfa Aesar. 5-Bromo-2-cyanopyridine, iron powder, magnesium chloride hexahydrate, potassium carbonate, and sodium carbonate were obtained from Frontier Scientific, Oakwood Chemicals, Bioshop, Lancaster, and Fluka respectively. 2-Cyanopyridine was obtained from both Alfa Aesar and Sigma-Aldrich. Palladium on charcoal (10 weight %) was obtained from Alfa Aesar, MCB, and Sigma-Aldrich. Acetic acid, ammonia (solution), N-acetylglycine, sodium azide, sodium chloride, and sodium sulfate were purchased from EMD. Ammonium acetate, 2-pyridinecarboxyaldehyde, and lithium hydroxide were purchased from Fisher. Copper(II) sulfate pentahydrate, potassium chloride, potassium hexafluorophosphate, and sodium bisulfite were purchased from Sigma-Aldrich. 1,8-Diazabicyclo[5.4.0]undec-7-ene (DBU), ethylenediaminetetracetic acid (EDTA, tetrasodium salt dihydrate), N-(3-dimethylaminopropyl)-N'-ethylcarbodiimide hydrochloride (EDC*HCl), and sodium hydroxide were purchased from VWR. Bis(triphenylphosphine)palladium(II) dichloride and silver trifluoromethanesulfonate (silver triflate, AgOTf) were purchased from Pressure Chemical Co. and Strem respectively.

Triethylamine (Alfa Aesar) was distilled in the presence of potassium hydroxide prior to use. MilliQ (ultrapure deionized) water was obtained from Millipore filtration systems. Other solvents, namely acetone, acetonitrile, anhydrous methanol, chloroform, dichloromethane (DCM), diethyl ether, ethyl alcohol (95%, EtOH), ethyl acetate (EtOAc), hexanes, methanol, tert-butanol, and toluene, were obtained from ACP and Fisher Chemicals. Anhydrous N,N'dimethylformamide (DMF) and tetrahydrofuran (THF) were purchased from EMD.

CELITE® 545 filter agent (Alfa Aesar) was used as required. Column chromatography was performed with Silica-P flash silica gel (40-63 μm particle size, 60 Å pore diameter) unless specified to be with Aluminum oxide, activated, neutral, Brockmann I standard grade (~150 mesh, 58 Å pore diameter). Ion exchange chromatography to convert triflates to chlorides was performed on Amberlite IRA-400 (chloride form).

2-Hydrazinopyridine and 5-nitro-2-hydrazinopyridine were prepared according to literature protocols (Kohata et al., *Bull. Chem. Soc. Jpn* (1990) 63: 3398-404) from hydrazine hydrate (98%, Alfa Aesar) and either 2-chloropyridine (Sigma-Aldrich and Alfa Aesar) or 5-nitro-2-chloropyridine (Alfa Aesar) respectively. 5-Ethynyl-2-pyridylcarboxaldehyde was likewise prepared from 5-bromo-2-pyridinecarboxaldehyde (Alfa Aesar) and trimethylsilylacetylene (Alfa Aesar) according to literature protocols (Benenato et al., patent WO2010/100475A1).

Bis(dimethylsulfoxide)platinum(II) dichloride was synthesized from potassium tetrachloroplatinate(II) (Pressure Chemical Co.) and dimethylsulfoxide (Alfa Aesar) as previously reported in the literature (Emmerich et al., *Eur. J. Med. Chem.* (2014) 75: 460-66).

Deuterated solvents were used as received, except for $CDCl_3$ which was neutralized by passing through a short column of basic alumina (such treated $CDCl_3$ is signaled below by an asterisk, i.e., '$CDCl_3$*'). $^1H$ NMR and $^{13}C$ NMR were performed using 300 MHz, 400 MHz and 500 MHz Bruker instruments at 25° C. Peak listings for all spectra are given in ppm and referenced against the residual solvent signal, except in the case of $D_2O$, where acetone was used as the internal reference. Assignments of $^1H$ and $^{13}C$ NMR spectra were confirmed by 2D NMR experiments (COSY, HSQC, HMBC).

Oligonucleotides (sequences listed below in Table 2) were obtained from Eurogentec and Sigma Aldrich Life Science and were used without further purification. Stock solutions of ~0.5 mM oligonucleotide in MilliQ water were prepared, and the exact concentrations determined from baseline-corrected UV-vis absorption measurements and molar extinction coefficients provided by the manufacturer. 40 mM Lithium cacodylate buffer (40 mM cacodylic acid solution in water with pH adjusted to 7.2 by addition of 1 M lithium hydroxide) and 1 M salt stock solutions were sterile filtered and stored at 4° C.

The binders of Formula (1) (see Table 1) were used in biophysical studies (see Examples 2-4) in their formulations as dichloride salts. The specified binders were formulated as triflate and/or $PF_6$ salts for the NIH-60 cancer cell line screening (see Example 5).

Example 1. Synthesis of Compounds of Formula (1)

Example 1A. Synthesis of Compound 2 and a Pt(2)₂ Complex

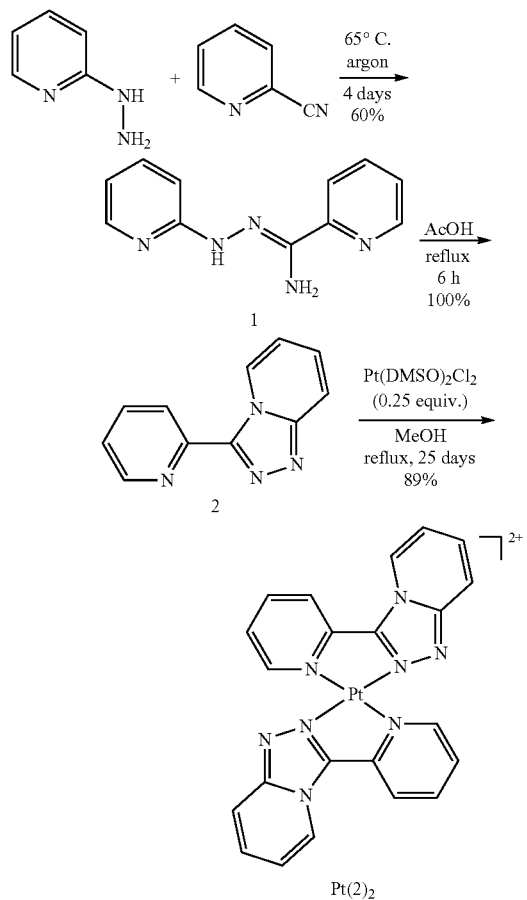

Compound 2 was synthesized from 2-hydrazinopyridine and 2-cyanopyridine through amidrazone intermediate 1 as previously reported in the literature (Klingele et al., Dalton Trans. (2010) 39: 4495-507). Its structure was confirmed by melting temperature (M.p. 127-128° C. vs 125° C. in literature) and $^1$H NMR (300 MHz, CDCl₃) 9.88 (br d, $^3J$=7.0 Hz, 1H), 8.72 (br d, $^3J$=4.5 Hz, 1H), 8.54 (d, $^3J$=8.1 Hz, 1H), 7.8-8.0 (m, 2H), 7.3-7.5 (m, 2H), 7.0 (br t, $^3J$=7 Hz, 1H).

The [Pt(2)₂]Cl₂ complex was synthesized by refluxing compound 2 (151 mg, 7.7×10⁻⁴ mol, 4.0 equiv.) and platinum bisdimethylsulfoxide dichloride (80.5 mg, 1.9×10⁻⁴ mol) in methanol (10 mL) with water (0.1 mL) for 2.5 days. A fine grey suspension was obtained and vacuum filtered; a resultant filtrate was evaporated and taken up in dichloromethane. A yellow solid was then obtained, filtered, and washed with dichloromethane, to yield 112 mg of [Pt(2)₂]Cl₂ (89%).

[Pt(2)₂]Cl₂: $^1$H NMR (400 MHz, D₂O with acetone as internal reference): 7.67-7.72 (td+td, 4 H, H5' & H5), 7.91-7.97 (m, 4H, H3' & H4'), 8.52 (td, $^4J$=1.1 Hz, $^3J$=7.8 Hz, 2 H, H4), 8.62 (d, $^3J$=8.0 Hz, 2 H, H3), 9.10 (d, $^3J$=7.2 Hz, 2 H, H6'), 9.93 (d, $^3J$=5.2 Hz, 2 H, H6). $^{13}$C NMR (100 MHz): 117.0 (C3'), 121.2 (C5'), 124.0 (C3), 125.3 (C6'), 128.5 (C5), 135.1 (C4'), 143.3 (C2), 144.4 (C4), 148.5 (CT), 149.3 (C2'), 153.7 (C6). HR ESI (+)MS ca/c. for [Pt(2)2]2+ (PtC₂₂H₁₆N₈): 293.5567, found: 293.5574; calc. for [Pt(2)2 Cl]⁺ (PtC₂₂H₁₆N₈Cl): 622.0834, found: 622.0833. See Table 1 for structural formula of the Pt complex Pt(2)₂.

Diagram indicating positions of functionalization in Examples 1B and 1C

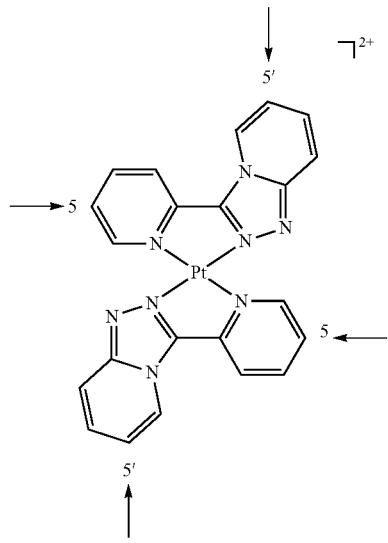

Example 1B. Functionalization of C5 pyridine position

Overview of synthetic strategies to form the ligands before platination:

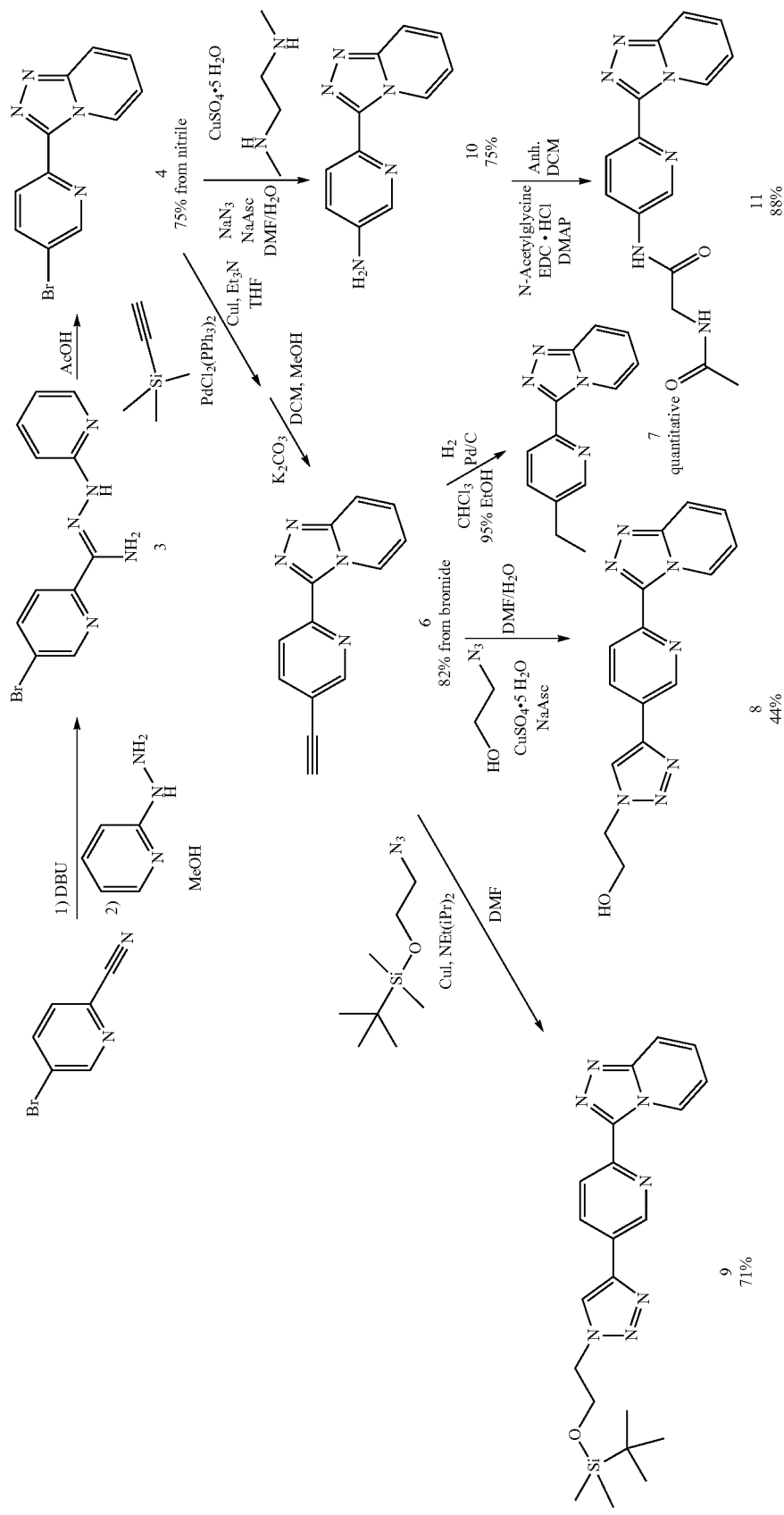

Procedures for organic transformations in the synthesis of novel compounds:

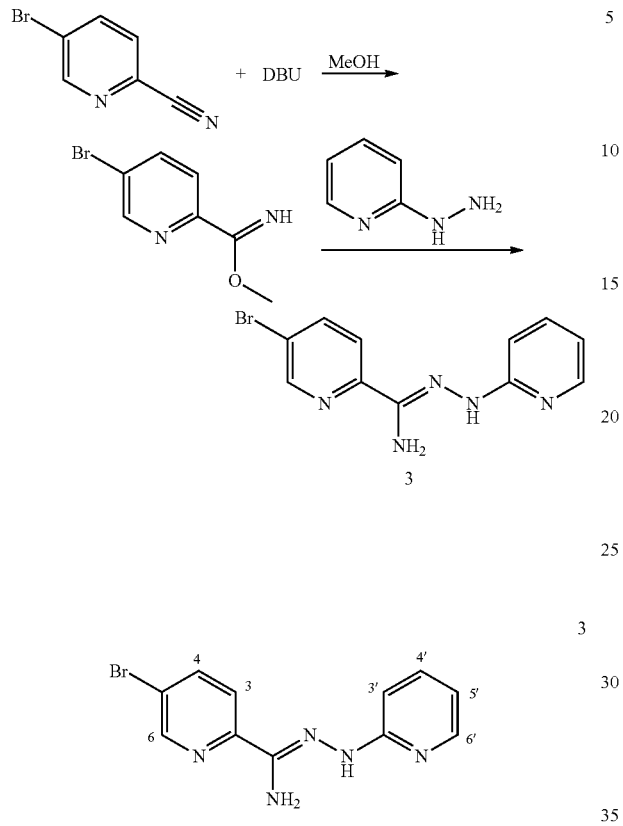

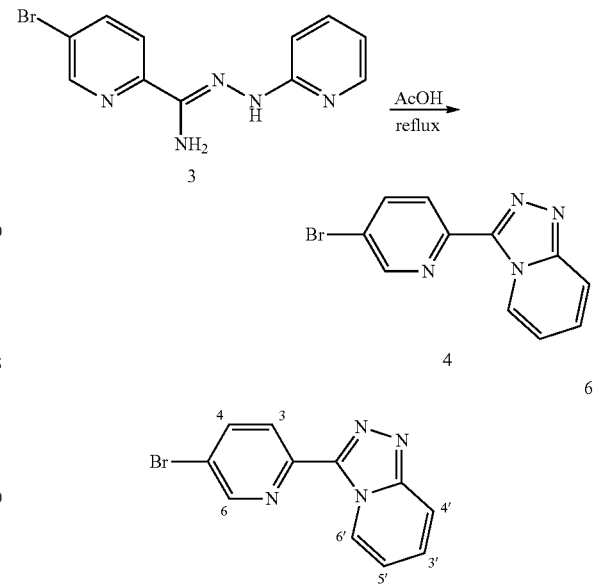

Compound 3. In a 2-neck 250 mL round-bottom flask were suspended 5-bromo-2-cyanopyridine (4.49 g, 24.5 mmol, 1.0 equiv.) in 45 mL of anhydrous methanol. DBU (1.3 mL, 8.7 mmol, 0.35 equiv.) were added, and the resultant mixture was refluxed for 10 min. under argon. The mixture was cooled down in a water bath, and 2-hydrazinopyridine (2.653 g, 24.3 mmol) was added as a solution (10 mL of methanol). The flask that had contained the 2-hydrazinopyridine solution was rinsed with 5 mL of dry methanol, and the rinsing was added to the mixture which appeared as a pale orange solution. The mixture was further stirred for 22 h at room temperature. The orange solution was acidified with acetic acid. A precipitate formed. The precipitate was isolated and washed with diethyl ether. It was then left to dry in a fume-hood overnight. It was then digested in 95% EtOH. This purification procedure gave two batches of product, namely (i) undissolved precipitate (1.086 g), which was isolated by vacuum filtration, (ii) precipitate that formed upon cooling of the filtrate (2.755 g). The original filtrate was also recrystallized in 25 mL EtOH, giving a precipitate (14 mg) and filtrate (8.38 g, containing acetic acid) as a third batch.

$^1$H NMR (300 MHz, CDCl$_3$*+10 drops CD$_3$OD): 8.50 (br s, 1H, H6), 8.06 (d, $^3$J=8.7 Hz, 1H, H3), 7.94 (br d, $^3$J=4 Hz Hz, 1H, H6'), 7.77 (dd, $^3$J=8.1 Hz, $^4$J=2 Hz, 1H, H4), 7.55 (t, $^3$J 20=7.4 Hz Hz, 1H, H4'), 7.25 (m under solvent signal, H3'), 6.67 (br t, $^3$J=5.6 Hz Hz, 1H, H5'). Mp: 201-202° C. Reference: Bogdanowicz et al., *Heterocycles* (2009) 78: 2217-31.

Compound 4. Since compound 3 was isolated in three batches, three reactions were run in parallel, at reflux in acetic acid (4.5 mL of acetic acid per gram of amidrazone) for 6 hours. To the solution (or partial suspension) was added copious amount of water. The filtered solid was left to dry in the fume-hood at least overnight, before taking up in DCM, and washing with dilute aqueous sodium carbonate. The aqueous layer was extracted twice with DCM and combined DCM layers were dried on sodium sulfate, filtered, and concentrated. White powders obtained from each run were purified by flash column chromatography on silica (DCM/acetone 100:10 to 100:30) to give a crystalline solid. The overall yield over two steps (DBU/hydrazine condensation and cyclization) was 75%.

$^1$H NMR (300 MHz, CDCl$_3$*): 9.72 (br d, $^3$J=6.9 Hz, 1H, H6'), 8.77 (d, N=1.5 Hz, 1H, H6), 8.47 (dd, $^3$J=8.6 Hz, $^4$J=0.6 Hz, 1H, H3), 8.01 (dd, $^3$J=8.6 Hz, $^4$J=2.5 Hz, 1H, H4), 7.88 (br d, $^3$J=9 Hz, 1H, H3'), 7.38 (ddd, $^3$J=9 Hz, $^3$J=6.6 Hz, $^4$J=1 Hz, 1H, H4'), 6.99 (td, $^3$J=6.8 Hz, $^4$J=1.2 Hz, 1H, H5'). $^{13}$C NMR (100 MHz, CDCl$_3$*): 151.3, 149.7, 146.7, 143.6, 139.7, 127.9, 126.8, 123.6, 120.6, 116.1, 114.5. Rf (SiO$_2$, 1:0.2 DCM/acetone)=0.30. Mp: 209-211° C. Reference: Klingele et al., *Dalton Trans*. (2010) 39: 4495-507.

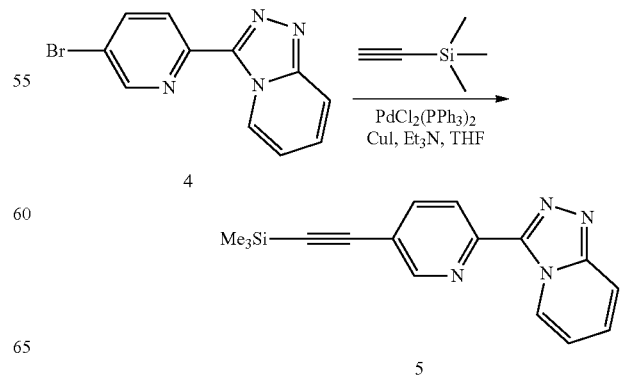

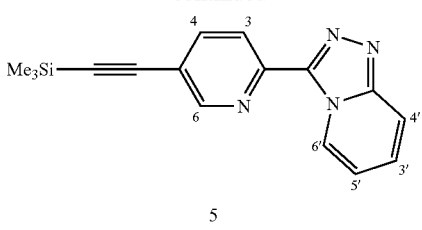

5

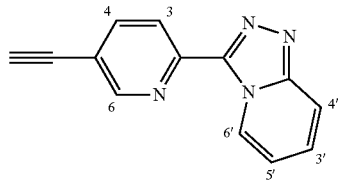

6

Compound 5. In a two-neck 25 mL round-bottom flask were placed compound 4 (410 mg, 1.49 mmol), b/s(triphenylphosphine)palladium(II) dichloride (86 mg, $1.2\times10^{-5}$ mol, 0.08 equiv.), and copper(I) iodide (45 mg, $2.4\times10^{-5}$ mol, 0.16 equiv.). The flask, mixed solids and condenser were purged with argon before solvent (dry THF, 20 mL) was added. Freshly distilled triethylamine (4 mL) was then introduced, and the resulting suspension was degassed by bubbling with argon for 15 minutes. Trimethylsilylacetylene (0.25 mL, 1.8 mmol, 1.2 equiv.) was then added and the mixture was degassed again for 5 minutes. A dark brown light suspension was then stirred at 60° C. under argon, while protected from light, for 17.5 h. Additional reagents were added as follows to form a mixture: a solid mixture of bis(triphenylphosphine)palladium(II) dichloride (25 mg, $3.6\times10^{-5}$ mol, 0.02 equiv.) and copper(I) iodide (14 mg, $7.4\times10^{-5}$ mol, 0.05 equiv.) were added as a solid. The mixture was degassed with argon before trimethylsilylacetylene (0.1 mL, $7\times10^4$ mol, 0.4 equiv.) was injected. The mixture was degassed again, and heated at 60° C. under argon for 4 additional hours. The mixture was then evaporated to dryness, taken up in DCM, filtered through CELITE®. The CELITE® pad was rinsed with DCM, and then with water. A DCM layer was isolated, aqueous layers were separated and extracted twice with DCM. Combined DCM layers were dried with sodium sulfate, filtered, and concentrated to afford a crude product as a solid. The crude product was then purified by flash chromatography on silica (DCM 100%, then DCM/acetone 100:10 to 100:20), giving 387 mg of a beige powder (89%). After the flash chromatography, an impurity was present at 7.4 and 7.65 ppm on the $^1$H NMR spectra. The impurity was removed after the following step.

$^1$H NMR (400 MHz, CDCl$_3$*): 9.73 (d, $^3$J=7.2 Hz, 1H, H6'), 8.72 (d, $^3$J=1.6 Hz, 1H, H6), 8.46 (d, $^3$J=8.0 Hz, 1H, H3), 7.88 (dd, N=8.4 Hz, N=2 Hz, 1H, H3'), 7.85 (d, $^3$J=9.2 Hz, 1H, H4), 7.34 (ddd, $^3$J=9 Hz, $^3$J=6.6 Hz, $^4$J=1 Hz, 1H, H4'), 6.99 (td, $^3$J=7 Hz, $^4$J=0.8 Hz, 1H, H5'). $^{13}$C NMR (100 MHz, CDCl$_3$*): 151.4, 151.3, 146.9, 143.9, 139.7, 128.0, 127.1, 121.6, 120.0, 116.1, 114.5, 101.3, 99.9, −0.2. Rf (SiO$_2$, 1:0.2 DCM/acetone)=0.42.

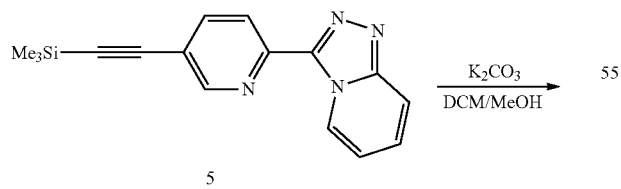

Compound 6. To a solution of compound 5 (387 mg, $1.3\times10^{-3}$ mol) in DCM (2 mL), methanol (10 mL) and potassium carbonate (491 mg, $3.6\times10^{-3}$ mol) were added. A resulting suspension was stirred at room temperature for 2 h, filtered and concentrated in vacuo. A residue was then taken up in DCM, and washed with water twice and then with brine. Combined aqueous layers were extracted twice with DCM, and combined DCM layers were dried on sodium sulfate, filtered, and concentrated in vacuo. A crude product was recrystallized from DCM/hexane to give 151 mg of an ocre solid as pure product, as well as a filtrate. The filtrate was evaporated to provide a yellow solid (128 mg) which was subjected to a second DCM/hexane recrystallization to give an additional 81 mg of pure product (total yield: 80%).

$^1$H NMR (400 MHz, CDCl$_3$*): 9.68 (dd, $^3$J=7.2 Hz, $^4$J=0.8 Hz, 1H, H6'), 8.66 (m, 1H, H6), 8.45 (dd, $^3$J=8.3 Hz, $^4$J=0.8 Hz, 1H, H3), 7.87 (dd, $^3$J=8.2 Hz, $^4$J=2.2 Hz, 1H, H4), 7.80 (dt, $^3$J=9.6 Hz, $^4$J=1 Hz, 1H, H3'), 7.31 (m, 1H, H4'), 6.92 (td, $^3$J=7 Hz, $^4$J=0.8 Hz, 1H, H5'), 3.31 (s, 1H, CH$_{alkyne}$). $^{13}$C NMR (100 MHz, CDCl$_3$*): 151.6, 151.2, 147.3, 143.7, 139.8, 127.9, 127.0, 121.5, 118.8, 116.0, 114.4, 81.9, 80.1. Mp: 184-185° C. (dec.).

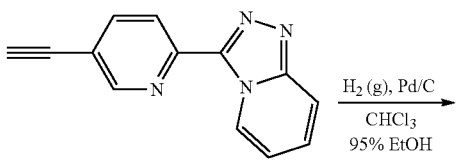

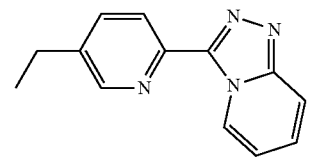

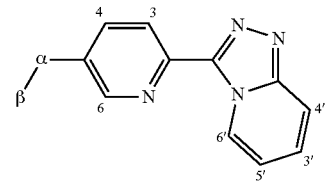

Compound 7. Compound 6 (40 mg, 1.8 mmol) was solubilized in 95% ethanol (5 mL) and chloroform (3 mL) to form a solution. The light orange solution was flushed with argon. Pd/C (9 mg, 10% on charcoal) was then added. The reaction mixture was purged with argon, was placed under an atmosphere of dihydrogen, and stirred at room temperature for 16 hours. The suspension was filtered on CELITE®, the CELITE® pad was rinsed with DCM, and the filtrate was concentrated to dryness to give 51 mg of a yellow residue (yield: quantitative).

$^1$H NMR (400 MHz, CDCl$_3$*): 9.68 (br d, $^3$J=6 Hz, 1H, H6'), 8.55 (br s, 1H, H6), 8.42 (m, 1H, H3), 7.94 (d, $^3$J=8.8 Hz, 1H, H3'), 7.71 (br d, $^3$J=8 Hz, 1H, H4), 7.42 (br t, N=8 Hz, 1H, H4'), 7.01 (t, $^3$J=7 Hz, 1H, H5'), 2.74 (q, $^3$J=7.6 Hz, 2H, H$_\alpha$), 1.31 (t, $^3$J=7.6 Hz, 3H, H$_\beta$).

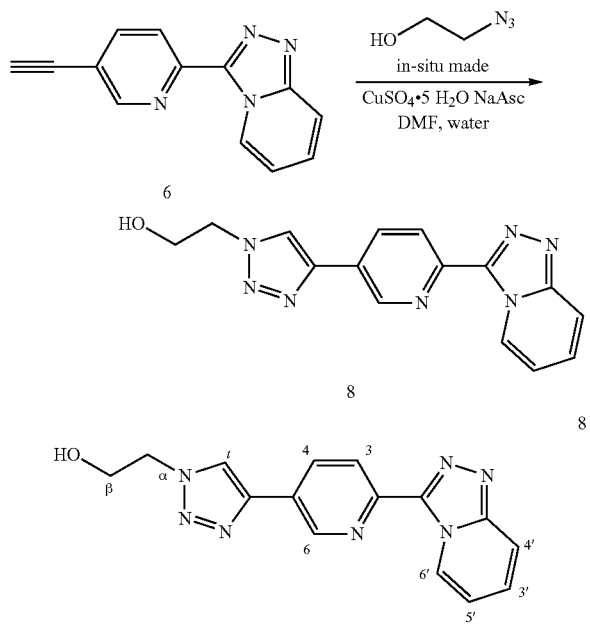

Compound 8. Method 1 (Small Scale): A flask with a solution of 2-bromoethanol (18 μL, 2.5×10$^{-4}$ mol, 2 equiv.) and sodium azide (25 mg, 3.8×10$^{-4}$ mol, 3 equiv.) in DMF (1 mL) was heated at 90° C. for 18.5 h. The solution was cooled down and added to compound 6 (26 mg, 1.2×10$^{-4}$ mol) to form a reaction mixture. The flask that had contained the azide solution was rinsed with 2×0.5 mL of DMF and the rinsing was added to the reaction mixture. Water (0.2 mL) was then added to the reaction mixture, followed by copper (II) sulfate (9 mg, 3.6×10$^5$ mol, ~0.3 equiv.) and sodium ascorbate (14.4 mg, 7.3×10$^{-5}$ mol, 0.6 equiv.). The reaction mixture was then degassed with argon for 15 minutes, and stirred at room temperature for 24 h. Concentrated aqueous ammonia (~1.5 mL) and saturated aqueous EDTA (~1 mL) were then added, forming a green aqueous layer that was extracted with EtOAc. The EtOAc layer did not contain any compound of interest. The aqueous phase from the extraction was left to stir in a fumehood overnight and formed a suspension. The suspension was taken up in water, filtered and washed with copious water, and then with diethyl ether to give 16.1 mg of a light beige powder (yield: 44%).

$^1$H NMR (300 MHz, DMSO-d$_6$): 9.73 (br d, $^3$J=6.6 Hz, 1H, H6'), 9.27 (br s, 1H, H6), 8.79 (br s, 1H, Ht), 8.48 (m, 2H, H3+H4), 7.95 (d, $^3$J=9 Hz, 1H, H3'), 7.54 (br t, $^3$J=8 Hz, 1H, H4'), 7.21 (t, $^3$J=6 Hz, 1H, H5'), 5.14 (br t, $^3$J=5 Hz, 1H, OH), 4.51 (br t, 2H, H$_\alpha$), 4.51 (m, 2H, H$_\beta$).

Method 2 (Larger Scale):

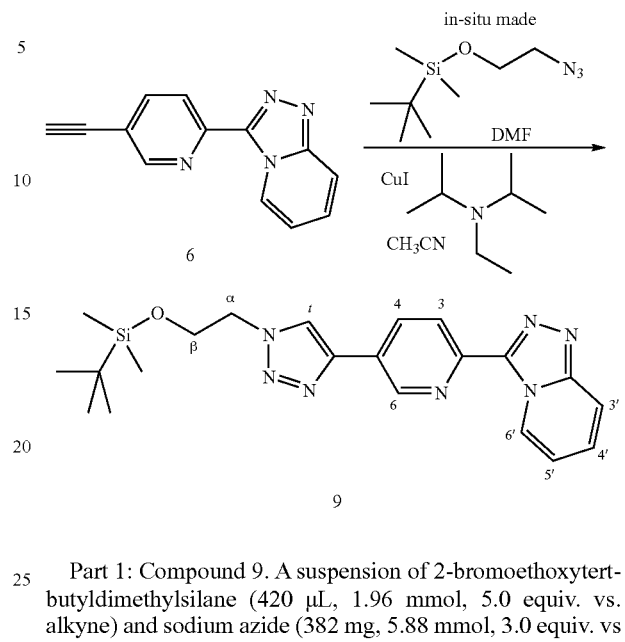

Part 1: Compound 9. A suspension of 2-bromoethoxytert-butyldimethylsilane (420 μL, 1.96 mmol, 5.0 equiv. vs. alkyne) and sodium azide (382 mg, 5.88 mmol, 3.0 equiv. vs bromide) in DMF (5 mL) was heated at 90° C. under argon overnight. The suspension was cooled down and transferred to a flask containing compound 6 (83 mg, 3.8×10$^{-4}$ mol) via pipette to form a reaction mixture. Di-isopropylethylamine (77 μL, 4.4×10$^{-4}$ mol, 1.1 equiv. vs. copper(I)) and copper(I) iodide (79 mg, 4.2×10$^{-4}$ mol, 1.1 equiv. vs. alkyne) in acetonitrile (3 mL) were added. The flask that had contained the azide suspension was rinsed with 3×0.5 mL of acetonitrile and the rinsings were added to the reaction mixture. The reaction mixture was degassed with argon for 15 minutes. The orange reaction mixture was left to stir at room temperature for 5 h, was left open to air for 3 h, and then was concentrated in vacuo with gentle heating (~45° C.). A red-brown solid was isolated and dissolved in DCM (~10 mL) to form a solution. Saturated aqueous ammonium acetate (~11 mL) and EDTA (360 mg) were then added to the solution. The solution was left to stir vigorously overnight. A blue-green aqueous layer was then separated from a light yellow DCM layer, and the aqueous layer was extracted 3 times with DCM. Combined DCM layers were dried (Na$_2$SO$_4$), filtered, and concentrated in vacuo to yield a yellow powder. The powder was purified by flash chromatography on silica gel eluted with a dichloromethane/acetone gradient, yielding 114 mg of a yellow solid (71%).

$^1$H NMR (400 MHz, CDCl$_3$*): 9.84 (d, $^3$J=7.2 Hz, 1H, H6'), 9.14 (d, N=1.6 Hz, 1H, H6), 8.59 (d, $^3$J=8.4 Hz, 1H, H3), 8.28 (dd, $^3$J=8.4 Hz, $^4$J=2.3 Hz, 1H, H4), 8.03 (s, 1H, Ht), 7.85 (d, $^3$J=9.6 Hz, 1H, H3'), 7.35 (dd, $^3$J=8.4 Hz, $^3$J=6.8 Hz, 1H, H4'), 6.97 (t, $^3$J=6.6 Hz, 1H, H5'), 4.56 (t, $^3$J=4.8 Hz, 2H, H$_\alpha$), 4.03 (t, $^3$J=4.8 Hz, 2H, H$_\beta$), 0.86 (s, 9H, tBu), −0.01 (s, 6H, CH$_3$). $^{13}$C NMR (100 MHZ, CDCl$_3$*): 151.2, 147.5, 145.7, 144.2, 144.0, 133.7, 127.8, 127.1, 126.6, 122.6, 121.7, 116.1, 114.3, 61.9, 52.9, 25.7, 14.0, −5.6. Rf(SiO$_2$, 1:0.5 DCM/acetone)=0.27. Mp: 254-256° C.

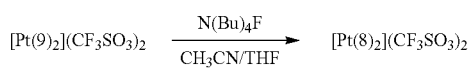

Part 2: [Pt(9)$_2$](OTf)$_2$. Synthesis described below.

Part 3: [Pt(8)$_2$](OTf)$_2$. The [Pt(9)$_2$](OTf)$_2$ complex (79 mg, 5.9×10$^{-5}$ mol) was solubilized in acetonitrile (80 mL) with heat. Tetra-n-butylammonium fluoride in solution in THF (270 μL, 1 M in THF, 2.7×10$^4$ mol, 4.6 equiv.) was added at once at room temperature, and the resulting mixture was stirred for 1 h. 95% Ethanol (~2 mL) was added, and solvents were evaporated in vacuo. A brown precipitate was taken up in DCM, forming a suspension that was filtered. The isolated solid was washed with DCM and dried. The dried solid was suspended in water and loaded onto a Sephadex SPC25 ion exchange column pre-treated with aqueous magnesium chloride, and eluted with aqueous MgCl$_2$ (gradient, 0 to 0.5 M). A yellow band was collected and a complex was precipitated by addition of saturated aqueous potassium hexafluorophosphate. A yellow precipitate was centrifuged down and dried to obtain Pt(8)$_2$](PFe)$_2$ (44 mg; 68%). The Pt(8)$_2$](PF$_0$)$_2$ complex was then run through an ion-exchange column on IRA-400 formulated as a chloride to give a total of 31 mg of (Pt(8)$_2$]Cl$_2$ (59%).

'Crude 2' after drying on sodium sulfate, filtration and concentration in vacuo. $^1$H NMR analysis in CDCl$_3$* indicated that the yellow Crude 1 (106 mg) was a 1:1 mixture of 10 'with something else' (possibly 4) and the orange Crude 2 (46.6 mg) contained only compound 10. TLC analysis revealed a reasonably polar compound in Crude 2 and Crude 1, consistent with the amine product, which was well separated by chromatography. Therefore Crude 1 and Crude 2 were combined, together with the crude of a smaller scale test reaction, and compound 10 isolated pure by flash chromatography on silica built in DCM/acetone 100:50 and eluted with DCM/acetone/methanol 100:50:0 to 0:100:5. A yellow powder was obtained (132.5 mg, 75% yield for combined reaction crudes).

$^1$H NMR (400 MHz, CDCl$_3$*+3 drops CD$_3$OD): 9.58 (dd, $^3$J=7.3 Hz, $^4$J=1 Hz, 1H, H6'), 8.0-8.15 (m, 2H, H3+H6), 7.69 (dd, $^3$J=9.2 Hz, =1 Hz, 1H, H3'), 7.27 (ddd, $^3$J=9.2 Hz, $^3$J=6.8 Hz, $^4$J=1 Hz, 1H, H4'), 7.09 (br dd, $^3$J=8.6 Hz, $^4$J~3 Hz, 1H, H4), 6.85 (br t, $^3$J=6.8 Hz, 1H, H5'). $^{13}$C NMR (100 MHz, CDCl$_3$*+3 drops CD$_3$OD): 150.3, 144.8, 143.6, 135.4, 127.9, 126.8, 123.5 (2 C), 121.9, 115.3, 113.9.

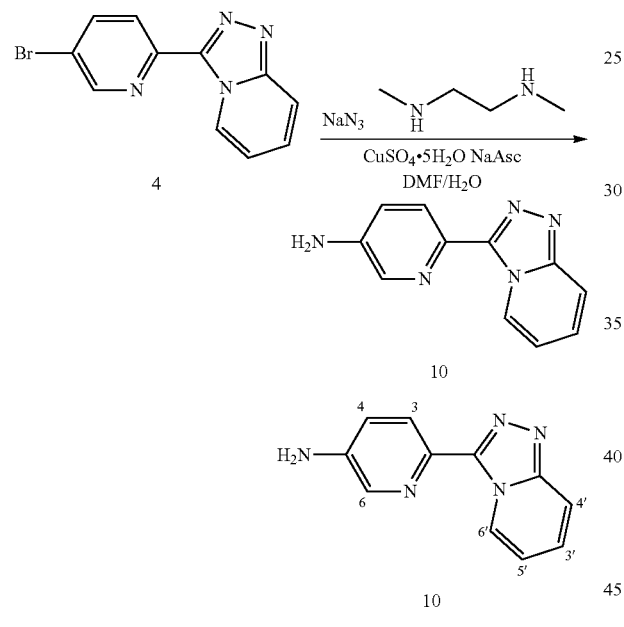

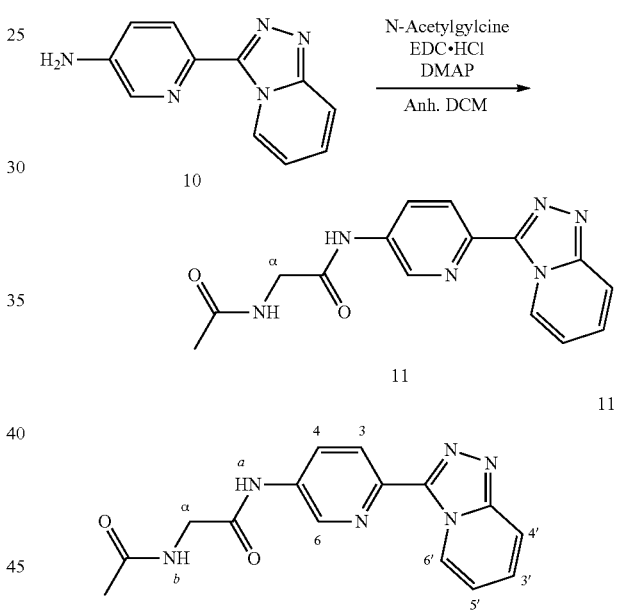

Compound 10. In a 50 mL 2-neck round bottom flask were suspended compound 4 (201 mg, 7.3×10$^{-4}$ mol), sodium azide (531 mg, 8.2×10$^{-3}$ mol, 11.2 equiv.), copper (II) sulfate pentahydrate (271 mg, 1.09×10$^{-3}$ mol, 1.5 equiv.) and sodium ascorbate (461 mg, 2.3×10$^{-3}$ mol, 3.2 equiv.) in DMF/water (15 mL/4 mL). To this yellow mixture was added N,N-dimethylethylene diamine (2×59 μL, 2.5×10$^{-4}$ mol, 1.5 equiv.). The mixture was degassed for 15 min. with argon, and heated at 85° C. under argon for 46 h. The mixture was transferred to a beaker and gently stirred to concentrate in air at room temperature in the fumehood overnight. The content was then transferred to a Petri dish to dry further until it formed a brown crust. The brown crust was then taken up in concentrated aqueous ammonia (~5 mL), and EDTA was added as a solid. Copious water was added (~60 mL), EtOAc was introduced and the two layers were isolated. The aqueous layer was extracted many times with EtOAc to produce 'Crude 1' after drying on sodium sulfate, filtration and concentration in vacuo. The aqueous layer was also further extracted with DCM to produce Compound 11. In a 25 mL 2-neck round bottom flask was dried compound 10 (83.0 mg, 3.93×10$^{-4}$ mol) under vacuum and fresh P$_2$O$_5$ for 30 min., and then dissolved in anhydrous DCM (— 12 mL). N-acetylglycine (97 mg, 8.28×10$^{-4}$ mol, 2.1 equiv.), EDC·HCl (230 mg, 1.20×10$^{-3}$ mol, 3.05 equiv.) and DMAP (54 mg, 4.4×10$^{-4}$ mol, 1.1 equiv.) were also dried on P$_2$O$_5$ for 15 min., then added as a solid mixture. The flask was flushed with argon and then stirred at room temperature for 22 h. The white precipitate was then filtered, washed with dichloromethane, water, and finally with diethyl ether. It was then dried on the high vacuum pump for 20 minutes, to yield 107 mg of the desired product as a white powder (88%).

$^1$H NMR (300 MHz, DMSO-d$_6$): 10.49 (br s, 1H, NHa), 9.65 (d, $^3$J=6.6 Hz, 1H, H6'), 9.00 (d, $^4$J=1.5 Hz, 1H, H6'), 8.2-8.4 (m, 3H, H3+H4+ NHb), 7.91 (d, $^3$J=9.3 Hz, 1H, H3'), 7.50 (br t, $^3$J=7 Hz, 1H, H4'), 7.15 (br t, $^3$J=6.8 Hz, 1H, H5'), 3.95 (d, $^3$J=5.4 Hz, 2 H, Ha), 1.91 (s, 3H, CH$_3$). M.p: 295-296° C. (dec.).

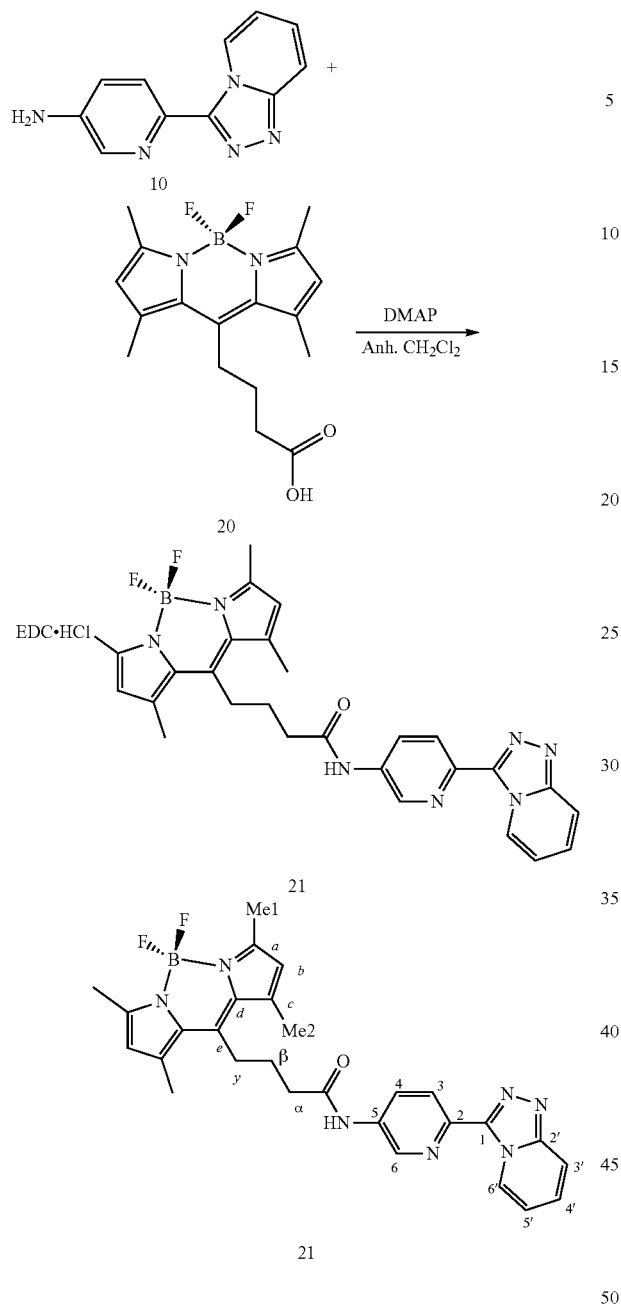

Compound 21. In a 25 mL 2-neck round bottom flask were dried compound 10 (14.1 mg, 6.67×10$^{-5}$ mol) and 20 ([reference] (30 mg, 9×10$^{-5}$ mol, 1.3 equiv.) under vacuum and fresh P$_2$O$_5$ for 20 min. EDC·HCl (54 mg, 2.8×10$^{-3}$ mol, 4.2 equiv.) and DMAP (12 mg, 9.8×10$^{-5}$ mol, 1.5 equiv.) were added, followed by anhydrous DCM (— 4 mL). The flask was flushed with argon and the suspension stirred at room temperature for 24 h. The solution was then washed with water, saturated aqueous sodium carbonate, and brine, dried on sodium sulfate, filtered and concentrated in vacuo. The crude was purified by flash column chromatography (SiO$_2$, acetone), and recrystallization from dichloromethane (slow evaporation), to yield 25.4 mg of the desired product as a dark red solid (72%).

$^1$H NMR (400 MHz, CDCl$_3$+5 drops of CD$_3$OD): 9.74 (d, $^3$J=7.2 Hz, 1H, H6'), 9.0 (br s, 1 H, H6), 8.32 (br d, $^3$J=7 Hz, 1H, H3), 8.09 (d, $^3$J=8.4 Hz, 1H, H4), 7.78 (d, $^3$J=8.8 Hz, 1H, H3'), 7.41 (br t, $^3$J=8 Hz, 1H, H4'), 7.00 (t, $^3$J=7 Hz, 1H, H5'), 6.04 (s, 2H, Hb), 3.0-3.1 (m, 2 H, Hγ), 2.57 (s, $^3$J=7 Hz, 2 H, Hα); 2.46 (s, 3H, Me1), 2.42 (s, 3H, Me2), 2.0-2.1 (m, 2 H, Hβ). $^{13}$c NMR (100 MHz, CDCl$_3$+5 drops of CD$_3$OD, based on HSQC and HBMC experiments): 180.7 (C=O), 163 (C1+Ca),155.1 (C2'), 154.2 (Ce), 149.7 (Cc), 140.2 (C6+Cd), 135 (C2), 128.9 (C4'), 127.5 (C4), 127.2 (C6'), 125 (C5), 122.9 (C3), 121.6 (Cb), 115.3 (C3'), 114.6 (C5'), 36.2 (Cα), 27.0 (Cγ), 26.9 (Co), 15.8 (Me2), 13.8 (Me1) [ Tentative because weak signal]. Reference: Dongchuan Wang, et al., J. Org. Chem. (2009) 41: 7675-7683.

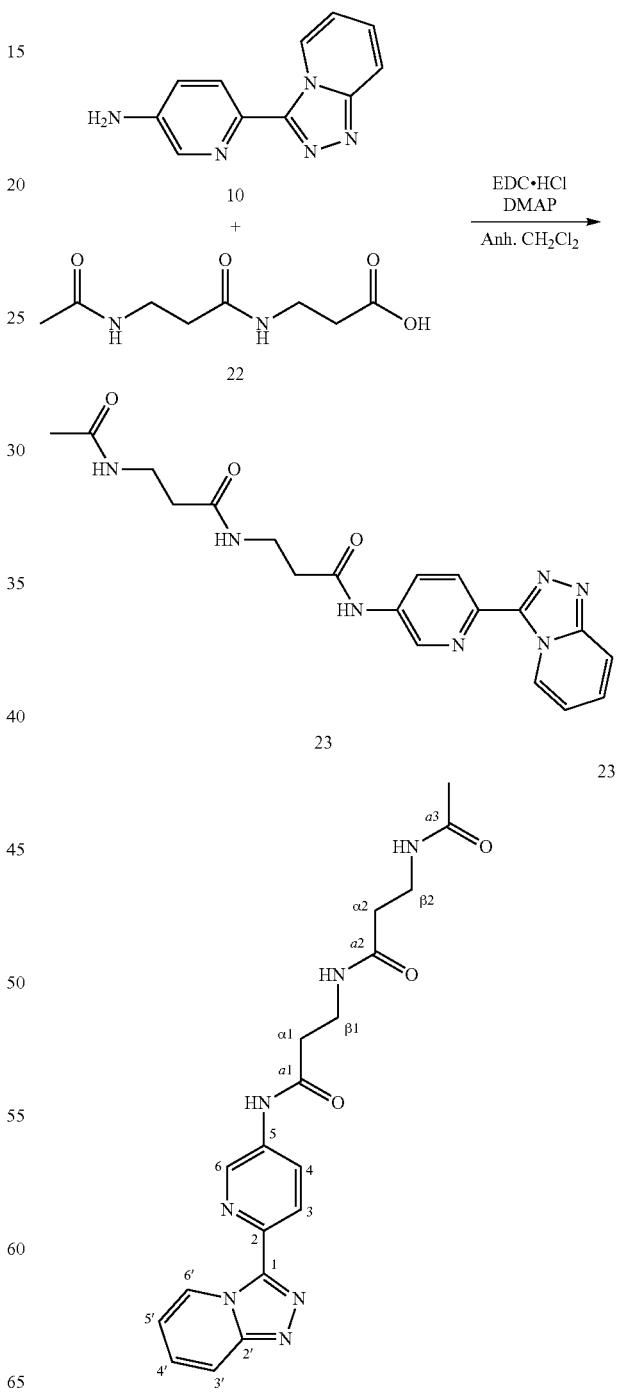

Compound 23. In a 25 mL 2-neck round bottom flask were dried compound amine 10 (20 mg, $9.5 \times 10^{-5}$ mol) and carboxylic acid 22 (38 mg, $1.9 \times 10^{-4}$ mol, 2.0 equiv.) under vacuum and fresh $P_2O_5$ for 20 min. EDC·HCI (34 mg, $1.8 \times 10^{-4}$ mol, 1.9 equiv.) and DMAP (3.1 mg, $2.5 \times 10^{-5}$ mol, 0.27 equiv.) were added, followed by anhy-drous DCM (—3 mL). The flask was flushed with argon and the suspension stirred at room temperature for 24 h. The white solid that formed was filtered, and suspended in a mixture of methanol (1.5 mL) and aqueous sodium carbonate (6 mL). After sonication for 15 minutes, the white powder was then filtered, washed with water and air-dried, to yield 24 mg of amide 23 (64%).

$^1$H NMR (400 MHz, $CDCl_3$+5 drops of $CD_3OD$): 9.54 (d, $^3J$=6.8 Hz, 1H, H6'), 8.76 (br s, 1H, H6), 8.12 (br d, $^3J$=8.8 Hz, 1H, H3), 7.97 (d, $^3J$=8.4 Hz, 1H, H4), 7.57 (d, $^3J$=9.2 Hz, 1 H, H3'), 7.22 (br t, $^3J$=9 Hz, 1H, H4'), 6.82 (t, $^3J$=7 Hz, 1H, H5'), 3.32 (t, $^3J$=6 Hz, 2 H, Hβ2), 3.20 (t, $^3J$=6 Hz, 2 H, Hβ1); 2.42 (t, $^3J$=6 Hz, 2 H, Hα2), 2.15 (t, $^3J$=6 Hz, 2 H, Hα2); 1.70 (s, 3 H, $CH_3$). $^{13}$C NMR (100 MHz, $CDCl_3$+5 drops of $CD_3OD$, based on HSQC and HBMC experiments): 172.0 (a2 C=O), 171.4 (a3 C=O), 170.7 (a1 C=O), 150.2 (C2'), 143.8 (C1), 140.0 (C6), 135.5 (C2), 132.2 (C4), 126.5 (C6'), 122.4 (C3), 122.0 (C5), 114.9 (C4'+C3'), 114.5 (C5'), 37.1 (Cal), 35.8 (Cpi), 35.5 (Cα2), 35.2 (Cβ2), 21.7 ($CH_3$).

Procedures for Platinum Complex Formation:

Platinum complexes to be used as G4 binders were prepared in three stages in acetone/methanol mixes (except for complexation with complexation with compound 9 which was conducted in acetonitrile):

Stage a: Stripping Chlorides Off Starting Material, Making the 4 Coordination Sites Available.

This reaction is common for all binders synthesized using this protocol. Typically, the platinum starting material (8.5 mg, $2.0 \times 10^5$ mol, weighed in a small vial) was transferred into a 25 mL pear-shape flask and solubilized in acetone (1.5 mL) with 10 drops of methanol. In a separate 'medium vial' was weighed silver triflate (10.5 mg, $4.09 \times 10^{-5}$ mol, 2.04 equiv.), which was then solubilized in acetone (1.5 mL) with 10 drops of methanol. The clear silver triflate solution was then transfer to the reaction flask containing the platinum reagent, with a glass pipette. The vial used for the silver reagent was rinsed with 0.5 mL of acetone (added to reaction flask), and the mixture stirred for another 25 minutes at room temperature, protected from light. The chunky precipitate in its mother liquor was then transferred portion-wise to a preweighed 1.5 mL Eppendorf™ polypropylene centrifuge tube, and centrifuged for 5 minutes. The resultant supernatant was carefully transferred to a large glass vial. More of the precipitate and mother liquor were transferred to the centrifuge tube, which was spun again for 5 minutes, and the supernatant transferred to the large vial. This cycle was repeated until the reaction flask was empty. Once all the reaction flask has been centrifuged, it was rinsed with 0.5-1 mL of acetone, the acetone rinse transferred to the centrifuge tube, the suspension was mixed using a vortex machine to resuspend the solid, and the mixture centrifuged down for 5 min. to separate the wash supernatant (transfer to the same large vial). The rinse with acetone (reaction flask/pipette/centrifuge tube/solid) was repeated with another 0.5-1 mL of acetone.

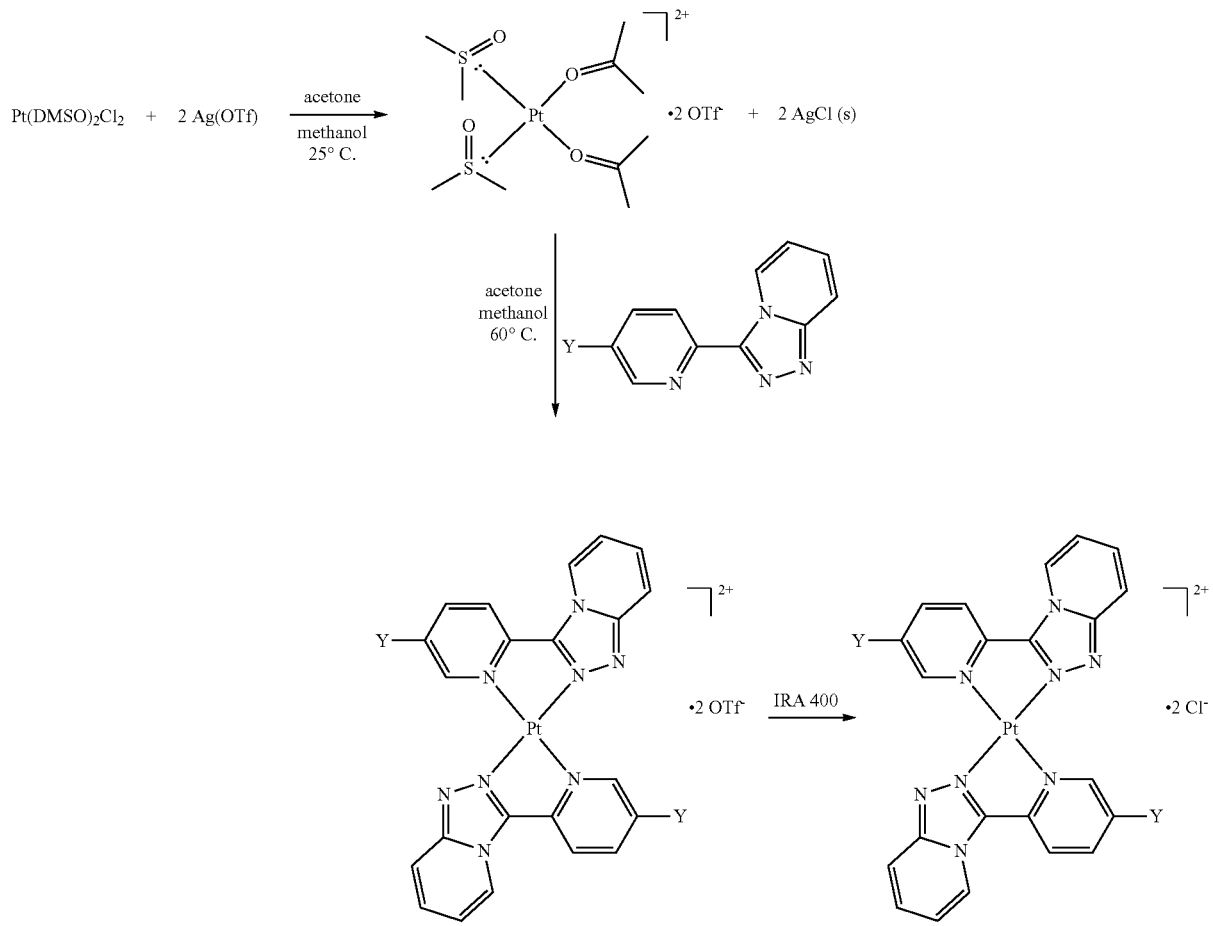

Stage b: Coordinating the 2 bidentate ligands.

Compounds 4-11 have various solubilities, so solvent volume and temperature may have to be adjusted. A table with some information relevant to the various known ligands and the resulting platinum complexes is given below.

| Compound | 4 | 6 | 7 | 8 | 9 | 10 | 11 |
|---|---|---|---|---|---|---|---|
| (mol, equiv. vs. Pt) | ($5.9 \times 10^{-5}$, 3.0 equiv.) | ($9.8 \times 10^{-5}$, 2.9 equiv.) | ($1.8 \times 10^{-4}$, 3.3 equiv.) | ($5.24 \times 10^{-5}$, 2.9 equiv.) | ($1.68 \times 10^{-4}$, 2.5 equiv.) | ($1.16 \times 10^{-4}$, 3.0 equiv.) | ($6.25 \times 10^{-5}$, 2.9 equiv.) |
| Acetone/ methanol | 3 mL/ 0 mL | 7 mL/ 0 mL | 6 mL/ 0 mL | MeOH, EtOH, acetone, 1 equiv. TFA | $CH_3CN$ | 6 mL/ 0 mL | 5 mL/ 5 mL (hot) |
| Yield of Complex as OTf salt (isolation) | 78% (yellow precipitate) | 59% (in supernatant) | 54% (in supernatant) | 46% (khaki precipitate) | 59% (yellow solid) | 62% (yellow precipitate) | 85% (orange precipitate) |

Typically, the organic compounds used in complexation with platinum were introduced in excess in solution in acetone (and possibly methanol) in the reaction flask, to which the supernatant of stage (a) is added. The empty large vial was rinsed with 2×0.5 mL of acetone, and the 'solution' was refluxed (60° C.) for 2.5 days. In most cases, the desired complex precipitates out of the reaction mixture as a yellow-orange powder which is centrifuged, washed with acetone and dried in air. The triflate complex were analyzed by $^1$H NMR in $CD_3CN$ with sharp signals.

Stage c: Exchanging triflate counterions for chloride counterions (for water solubility)

An ion exchange column was formulated from a commercially available hydroxide form to a chloride form. As a first step, AMBERLITE™ IRA400 was soaked in 1 M aqueous sodium chloride overnight. The AMBERLITE™ beads were then placed in a plastic column to form an ion exchange column. The column was then drained and washed with copious amounts of milliQ water.

If a triflate salt of the complex was very soluble in acetonitrile, then a concentrated sample was prepared in acetonitrile. The sample was loaded on the column, and eluted with milliQ water. The eluted complex was collected in a preweighed plastic 12 mL Eppendorf™ tubes for lyophilization.

If the triflate complex was not highly soluble in acetonitrile, it was dissolved in the necessary amount of acetonitrile or other solvent in a round bottom flask, then pretreated (soaked overnight in aqueous sodium chloride) beads were added to form a mixture, and the mixture was gently concentrated to dryness. The mixture was then loaded onto a prepared column, and the mixture's container was rinsed with milliQ water which was then loaded into the column. Elution with milliQ water was performed into 12 mL Eppendorf™ tubes. Lyophilization was conducted and a chloride salt of the complex was obtained.

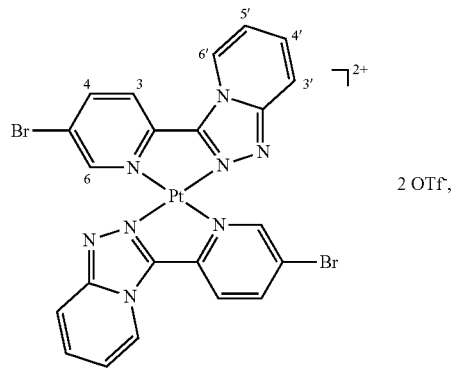

Compound Pt(4)$_2$: $^1$H NMR of OTf salt (300 MHz, $CD_3CN$, $D_2O$): 10.77 (d, $^4J$=1.5 Hz, 2 H, H6), 9.05 (d, $^3J$=6.6 Hz, 2 H, H6'), 8.84 (dd, $^3J$=8.5 Hz, $^4J$=1.4 Hz, 2 H, H4), 8.56 (d, $^3J$=9.3 Hz, 2 H, H3), 8.30 (d, $^3J$=9.0 Hz, 2 H, H3'), 8.0 (br t, $^3J$=8 Hz, 2 H, H4'), 7.66 (br t, $^3J$=6.9 Hz, 2 H, H5'). HR-ESI (+) of Cl salt: calc. for [Pt(4)$_2$]$^{2+}$ (PtC$_{22}$H$_{14}$N$_8$Br$_2$): 371.4673, found: 371.4699 (100%); calc. for [Pt(4)2 Cl] (PtC$_{22}$H$_{14}$N$_8$Br$_2$Cl): 777.9045, found: 777.9127 (4%); calc. for [4 Hr (C$_{11}$H8N$_4$Br): 274.9932, found: 274.9942 (14%).

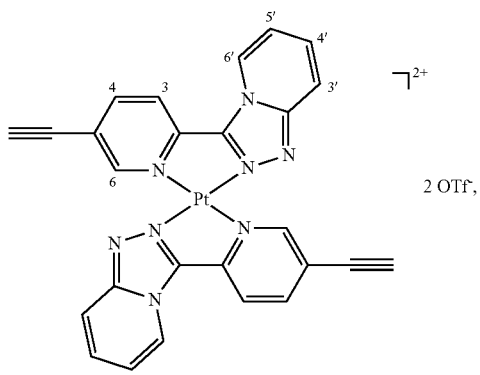

Compound Pt(6)₂: ¹H NMR of OTf salt (300 MHz, CD₃CN): 10.72 (d, ⁴J=1.8 Hz, 2 H, H6), 8.96 (d, ³J=7.2 Hz, 2 H, H6'), 8.67 (dd, ³J=8.4 Hz, ⁴J=1.5 Hz, 2 H, H4), 8.54 (d, ³J=8.4 Hz, 2 H, H3), 8.29 (d, ³J=9.6 Hz, 2 H, H3'), 8.0 (m, 2 H, H4'), 7.65 (br t, ³J=6.6 Hz, 2 H, H5'), 4.21 (s, 2H, alkyne CH). HR-ESI (+) of Cl salt: calc. for [Pt(6)₂]²⁺ (PtC₂₆H₁₆N₈): 317.5567, found: 317.5576 (47%); calc. for [Pt(6)₂. Cl] (PtC₂₆H₁₆N₈Cl): 670.0830, found: 221.0829 (100%).

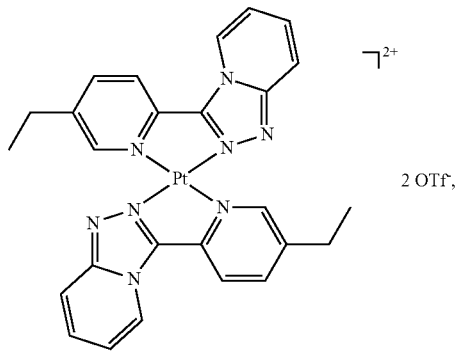

Compound Pt(7)₂: ¹H NMR of OTf salt (300 MHz, CD₃CN+1 drop D₂O): 10.57 (br s, 2H, H6), 8.98 (d, ³J=7.2 Hz, 2 H, H6'), 8.4-8.5 (m, 4 H, H3+H4), 8.25 (d, ³J=9.3 Hz, 2 H, H3'), 7.95 (br t, 2 H, H4'), 7.60 (t, ³J=6.9 Hz, 2 H, H5'), 3.11 (q, ³J=7.4 Hz, 4 H, Hₐ), 1.51 (q, ³J=7.5 Hz, 6 H, Hᵦ). HR-ESI (+) of Cl salt: ca/c. for [Pt(7)₂]²⁺(PtC₂₆H₂₄N₈): 321.5880, found: 321.5875 (100%); ca/c. for [7 Hr (C₁₃H₁₃N₄): 225.1140, found: 225.1134 (6%).

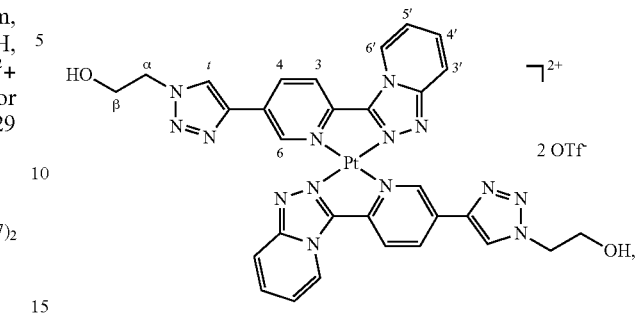

Compound Pt(8)₂: ¹H NMR of OTf salt (300 MHz, CD₃CN+3 drops CD₃OD): 11.23 (d, ⁴J=1.5 Hz, 2 H, H6), 9.03 (d, ³J=6.9 Hz, 2 H, H6'), 8.96 (d, ³J=8.4 Hz, 2 H, H4), 8.70 (s, 2H, Ht), 8.63 (d, ³J=8.4 Hz, 2 H, H3), 8.32 (d, ³J=9.6 Hz, 2 H, H3'), 7.99 (br t, ³J ~8 Hz, 2 H, H4'), 7.64 (br t, ³J ~6 Hz, 2 H, H5'), 4.67 (br t, ³J ~5 Hz, 4 H, Hₐ), 4.04 (br t, ³J ~5 Hz, 4 H, Hᵦ). HR-ESI (+) of Cl salt: ca/c. for [Pt(8)₂]²⁺+(PtC₃₀H₂₆N₁₄O₂): 404.6000, found: 404.6003 (100%).

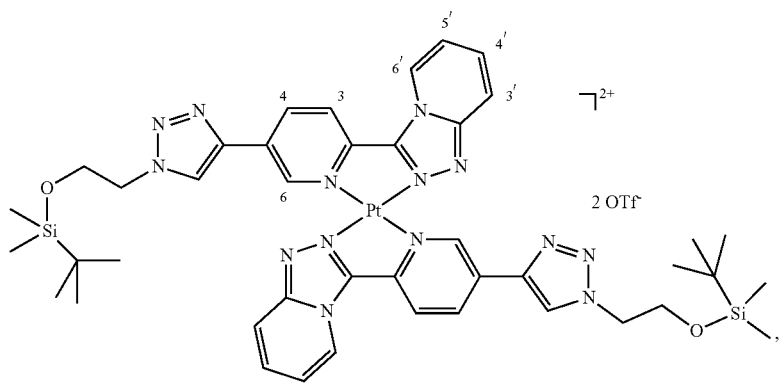

[Pt(9)₂](OTf)₂ was prepared in acetonitrile (both steps), in order to avoid deprotection of the tert-butylmethylsilane group (which occurs in acetone/methanol or acetone alone). In the 2ⁿᵈ step, the precipitate was extracted in acetonitrile. It was concentrated in vacuo to yield the desired product, after washing the excess ligand away with DCM (yield: 98%).

$^1$H NMR (300 MHz, CD$_3$CN): 11.25 (d, $^4$J=1.2 Hz, 2 H, H6), 9.00 (d, $^3$J=7.2 Hz, 2 H, H6'), 8.94 (dd, $^3$J=8.6 Hz, $^4$J=2.0 Hz, 2 H, H4), 8.61 (d, $^3$J=9.6 Hz, 2 H, H3), 8.59 (s, 2H, Ht), 8.30 (d, $^3$J=9.3Hz, 2 H, H3'), 8.0 (br dd, $^3$J~9 Hz, $^4$J~1 Hz, 2 H, H4'), 7.65 (br t, $^3$J~7 Hz, 2 H, H5'), 4.69 (br t, $^3$J~5 Hz, 4 H, H$_\alpha$), 4.13 (br t, $^3$J~5 Hz, 4 H, H$_e$), 0.82 (s, 9H, tBu), -0.01 (s, 6H, CH$_3$).

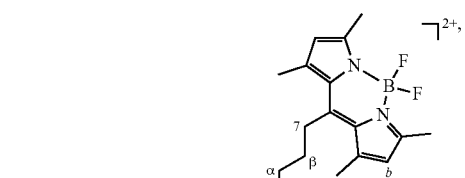

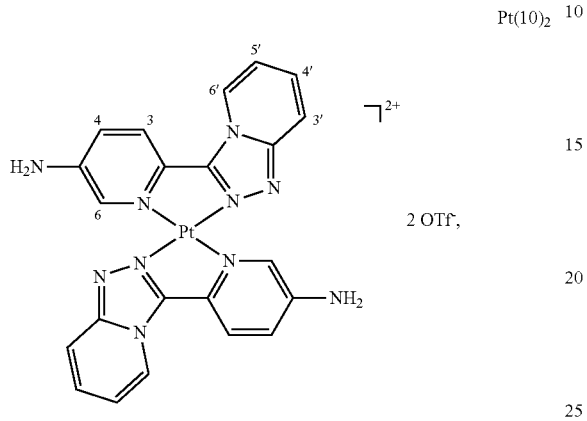

Compound Pt(10)$_2$: $^1$H NMR of OTf salt (300 MHz, CD$_3$CN+3 drops CD$_3$OD): 10.01 (br s, 2H, H6), 8.75 (d, $^3$J=6.9 Hz, 2 H, H6'), 8.16 (d, $^3$J=9 Hz, 2 H, H3), 8.07 (d, $^3$J=9.6 Hz, 2 H, H3'), 7.82 (br t, $^3$J=7.5 Hz, 2 H, H4'), 7.58 (dd, $^3$J=8.9 Hz, $^4$J=2.2 Hz, 2 H, H4), 7.60 (br t, $^3$J=6.8 Hz, 2 H, H5'). HR-ESI (+) of Cl salt: calc. for [Pt(10)$_2$]$^{2+}$ (PtC$_{22}$H$_{18}$N$_{10}$): 308.5676, found: 308.5689 (62%); calc. for [Pt(10)$_2$·Cl]+(PtC$_{22}$H$_{18}$N$_{10}$Cl): 652.1052, found: 652.1084 (<0.5%); calc. for [10 H]+(C$_{11}$H$_{10}$N$_5$): 212.0936, found: 212.0940 (3%).

Compound Pt(21)$_2$: $^1$H NMR of OTf salt (300 MHz, 4:2 CD$_3$CNl, CD$_3$OD, 3 drops of CDCl$_3$): 11.2 (d, $^4$J=2 Hz, 2 H, H6), 9.04 (d, $^3$J=7.2 Hz, 2 H, H6'), 8.63 (dd, $^3$J=9 Hz, $^4$J=2 Hz, 2 H, H4), 8.58 (d, $^3$J=9 Hz, 2 H, H3), 8.23 (d, $^3$J=8 Hz, 2 H, H3'), 7.98 (t, $^3$J=8 Hz, 2 H, H4'), 7.64 (t, $^3$J=7Hz, 2 H, H5'), 6.21 (s, 4H, Hb), 3.0-3.2 (m, 4 H, Hγ), 2.84 (t, $^3$J=8 Hz, 4 H, Hα), 2.58 (s, 6H, Me), 2.49 (s, 6H, Me), 2.2-2.3 (m, 4 H, Hβ). HR-ESI MS (+) of Cl salt: calc. for [PtC$_{56}$H56B$_2$F$_4$N$_{14}$O$_2$]$^{2+}$: 624.7240, found: 624.7226 (100%). UV-visible absorption (λmax (nm), CH$_3$CN/CH$_3$OH): 306, 327, 391, 413, 470 (shoulder), 496. Fluorescence emission (λmax (nm), CH$_3$CN/CH$_3$OH): 502 nm.

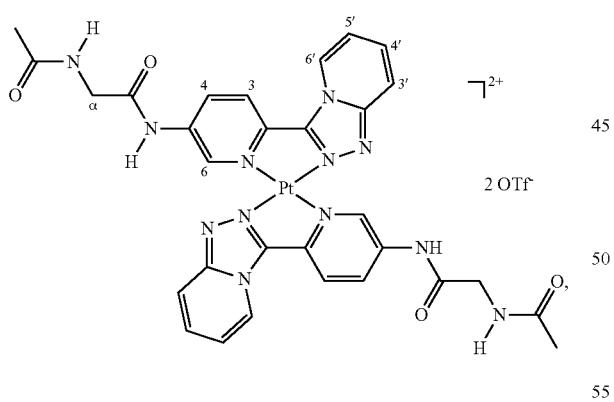

Compound Pt(11)$_2$: $^1$H NMR of OTf salt (300 MHz, CD$_3$CN+CD$_3$OD): 10.88 (d, $^4$J=1.5 Hz, 2 H, H6), 8.99 (d, $^3$J=6.6 Hz, 2 H, H6'), 8.46 (d, $^3$J=9 Hz, 2 H, H3), 8.17 (br d, $^3$J 9 Hz, 2 H, H4), 7.81 (br t, $^3$J=8 Hz, 2 H, H4'), 7.61 (t, $^3$J=6.8 Hz, 2 H, H5'), 7.4-7.5 (very br d, 2 H, H3'), 4.15 (s, 4H, H$_\alpha$), 2.24 (s, 6H, Ac). HR-ESI (+) of Cl salt: calc. for [Pt(11)$_2$]$^{2+}$(PtC$_{30}$H$_{28}$N$_{12}$O$_4$): 407.5997, found: 407.5999 (100%).

Pt(23)$_2$: $^1$H NMR of OTf salt (300 MHz, 1:1 CD$_3$CN/CD$_3$OD): 11.2 (s, 2 H, H6), 9.12 (d, $^3$J=7.5 Hz, 2 H, H6'), 8.6-8.7 (m, 4 H, H3+H4), 8.26 (d, $^3J$=8 Hz, 2 H, H3'), 7.98 (t, $^3J$=7.5 Hz, 2 H, H4'), 7.64 (t, $^3J$=7 Hz, 2 H, H5'), 3.69 (t, $^3J$=7 Hz, 4 H, Hβ), 3.43 (t, $^3J$=7 Hz, 4 H, Hβ2), 2.83 (t, $^3J$=7 Hz, 4 H, Hα1), 2.42 (t, $^3J$=7 Hz, 4 H, Hα2), 1.90 (s, 6H, Me). HR-ESI MS (+) of triflate salt: calc. for $[PtC_{38}H_{42}N_{14}O_6]^{2+}$: 492.6530, found: 462.6511 (100%).

Example 1C. Functionalization of C5' on Fused Heterocycle

Overview of synthetic strategy:

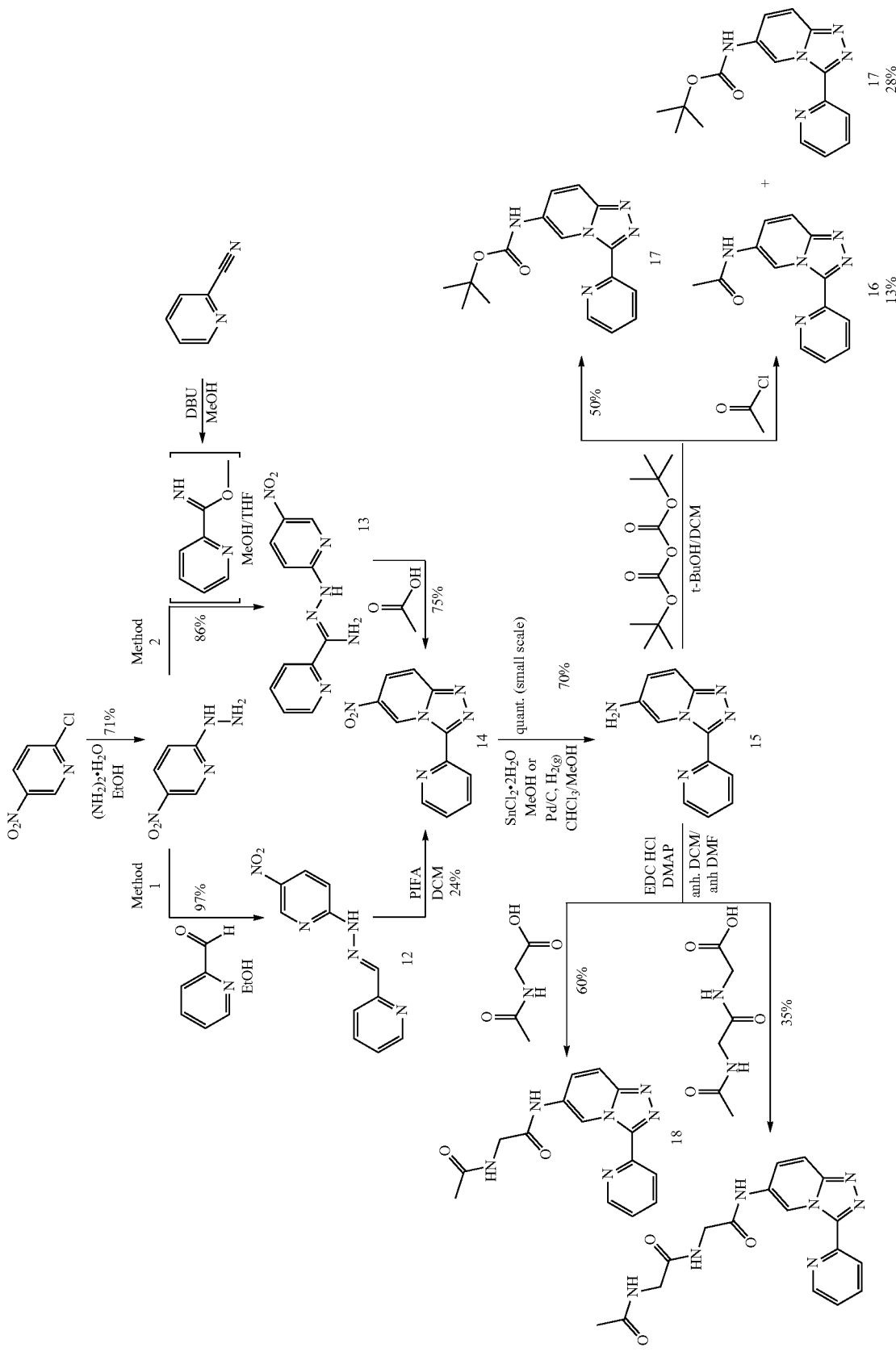

Procedures for organic transformations in the synthesis of novel compounds:

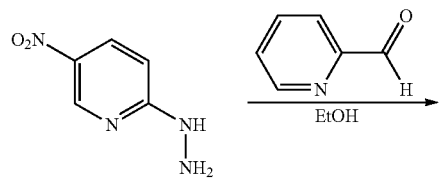

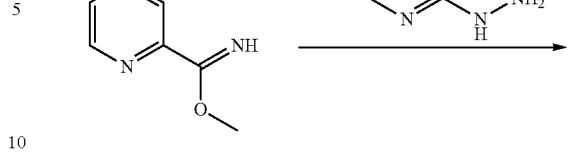

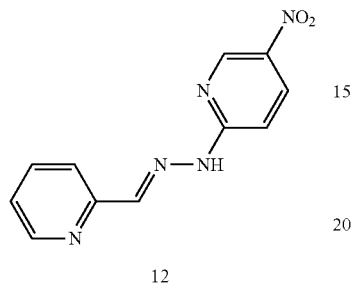

12

Compound 12. To a suspension of 5-nitro-2-hydrazinopyridine (2.45 g, 0.0159 mol, 1 equiv.) in ethanol (27 mL) heated to reflux was added dropwise a solution of 2-pyridinecarboxyaldehyde (2.75 g, 0.0289 mol, 1.8 equiv.) in ethanol (28 mL). The suspension was heated under reflux for an additional 30 minutes, then cooled to room temperature. Vacuum filtration and rinsing with cold ethanol afforded the product as a bright yellow solid (3.74 g, 97%). The product was used without purification in the following reaction.

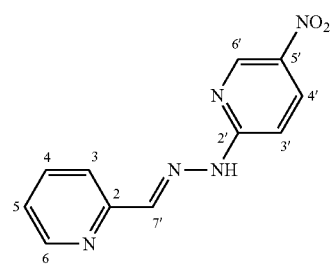 [SMILES: O=[N+]([O-])c1ccc(N/N=C/c2ccccn2)nc1]

$^1$H NMR (500 MHz, DMSO-$d_6$): 7.39 (ddd, $^4J$=1.3 Hz, $^3J$=5.0 & 7.5 Hz, 1H, H5), 7.41 (d, $^3J$=9.5 Hz, 1H, H3') 7.87 (td, $^4J$=1.5 Hz, $^3J$=7.5 Hz, 1H, H4), 8.04 (d, $^3J$=8.0 Hz, 1H, H3), 8.24 (s, 1H, H7'), 8.42 (dd, $^4J$=2.8 Hz, $^3J$=9.3 Hz, 1H, H4'), 8.59 (br d, $^3J$=5.0 Hz, 1H, H6), 9.04 (d, $^4J$=3.0 Hz, 1H, H6'), 12.17 (br s, 1H, NH). $^{13}$C NMR (100 MHz): 106.0, 119.7, 124.0, 133.7, 136.8, 137.1, 144.4, 146.1, 149.5, 153.2, 159.8. Mp: 260-261° C.

Reference: Padalkar et al., Synth. Commun. (2011) 41: 925-38.

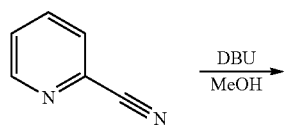

Compound 13. 2-Cyanopyridine (1.84 g, 0.0177 mol, 1.0 equiv., pre-dried under $P_2O_5$, 10 min.) was suspended in anhydrous methanol (16 mL). 1,8-Diazabicyclo[5.4.0]undec-7-ene (DBU, 0.925 mL, 6.19 mmol), 0.4 equiv.) was added and the mixture refluxed (70° C.) under argon for 10 minutes. The resulting clear solution was added drop-wise to a flame-dried flask containing a suspension of 5-nitro-2-hydrazinopyridine (2.72 g, 0.0176 mol, 1.0 equiv., pre-dried under $P_2O_5$, 30 min.) in anhydrous tetrahydrofuran (THF, 16 mL) and methanol (16 mL), inducing an immediate colour change from green to dark red. The suspension was stirred at room temperature under argon overnight. After addition of acetic acid (25 mL), the product was isolated by vacuum filtration as dark red crystals (3.93 g, 86%). Additional product was isolated from the filtrate (2.37 g, still containing acetic acid) and was also used in the next reaction.

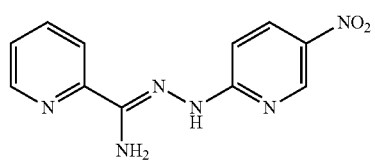

$^1$H NMR (300 MHz, DMSO-$d_6$): 6.94 (s, 2H, $NH_2$), 7.26 (br d, $^3J$=8.5 Hz, 1H, H3'), 7.45 (td, $^4J$=1.3 Hz, $^3J$=7.2 Hz, 1H, H5), 7.87 (td, $^4J$=1.8 Hz, $^3J$=7.8 Hz, 1H, H4), 8.22 (d, $^3J$=8.5 Hz, 1H, H3), 8.30 (dd, $^4J$=2.8 Hz, $^3J$=9.3 Hz, 1H, H4'), 8.58 (d, $^3J$=4.0 Hz, 1H, H6), 8.96 (d, $^4J$=2.0 Hz, 1H, H6'), 10.65 (br s, 1H, NH). $^{13}$C NMR (100 MHz): 105.0, 120.5, 124.6, 133.3, 135.3, 136.9, 144.6, 146.5, 148.2, 150.3, 160.0. Mp: 104.8-106.1° C.

Reference: Bogdanowicz et al., Heterocycles (2009) 78: 2217-31.

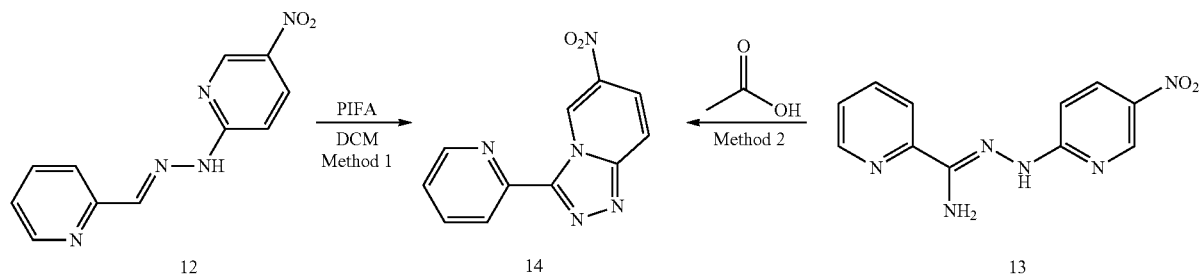

Compound 14. Method 1: A solution of compound 12 (606 mg, 2.49 mmol, 1.0 equiv.) and [bis(trifluoroacetoxy)-iodo]benzene (PIFA, 2.15 g, 4.99 mmol, 2.0 equiv.) in DCM (18 mL) was stirred at room temperature overnight. The solution was diluted in DCM and washed with saturated aqueous sodium bisulfite, saturated aqueous sodium bicarbonate, and water. Combined DCM phases were dried over excess sodium sulfate and the solvent was removed under reduced pressure to afford the crude product (>100%). Column chromatography on $SiO_2$ with gradient DCM:acetone as eluent afforded purified compound 14 as a light yellow powder (218 mg, 24%). Alternatively, washing the crude product with toluene removed some excess oxidizing agent, and this partially purified product (1.52 g, 51% recovery) was also successfully used in the following reaction. Reference: Padalkar et al., Synth. Commun. (2011) 41: 925-38. Method 2: A solution of 13 (3.83 g, 0.0148 mol, 1.0 equiv.) in acetic acid (32 mL) was heated and stirred under reflux (122° C.) overnight (15 hours). The reaction mixture was cooled to room temperature, diluted with water (50 mL), and left at 4° C. for 30 minutes. Vacuum filtration and washing with water and diethyl ether afforded dark red crystals as the crude product (2.69 g, 75%). By NMR this product was substantially free of impurity. Reference: Klingele et al., Dalton Trans. (2010) 39: 4495-507.

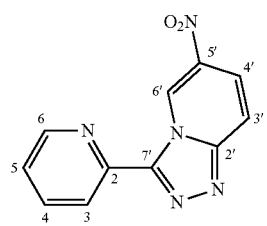

$^1$H NMR (400 MHz, $CDCl_3$*): 7.47 (ddd, $^4J$=0.8 Hz, $^3J$=5.0 & 7.4 Hz, 1 H, H5), 7.90 (d, $^3J$=9.6 Hz, 1H, H3'), 7.90-7.94 (m, 1H, H4), 8.11 (dd, $^4J$=2.0 Hz, $^3J$=9.8 Hz, 1H, H4'), 8.57 (d, $^3J$=8.0 Hz, 1H, H3), 8.81 (br d, $^3J$~4 Hz, 1H, H6), 11.00 (d, $^4J$=1.2 Hz, 1H, H6'). $^{13}$C NMR (100 MHz): 116.3, 122.0, 123.1, 124.9, 128.5, 137.6, 138.9, 146.4, 147.3, 149.3, 150.4. Rf ($SiO_2$, 6:1 DCM/acetone)=0.33. HR EI(+): calc. for [14]'+($C_{11}H_7N_5O_2$): 241.0599, found: 241.0605; calc. for [14-$NO_2$] ($C_{11}H_7N_4$): 195.0671, found: 195.0794. Mp: 226-228° C.

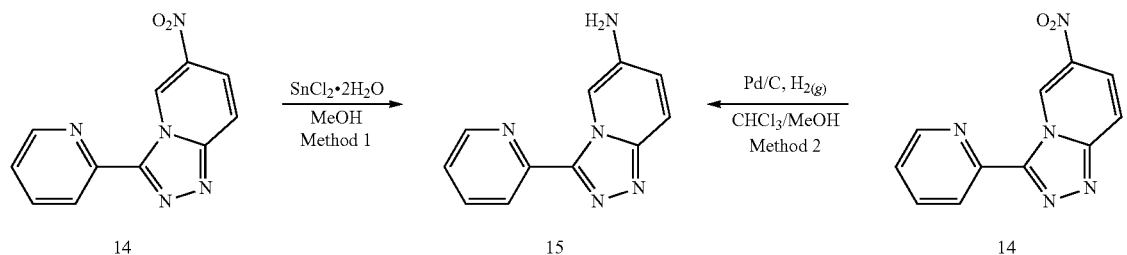 [SMILES: O=[N+]([O-])c1ccc2nnc(-c3ccccn3)n2c1 ; "SnCl2·2H2O" ; "MeOHMethod 1" ; Nc1ccc2nnc(-c3ccccn3)n2c1 ; O=[N+]([O-])c1ccc2nnc(-c3ccccn3)n2c1]

Compound 15. Method 1: To a suspension of compound 14 (590 mg, 2.45 mmol 1.0 equiv.) in methanol (120 mL) was added tin(II) chloride (9.93 g, 0.044 mol, 18 equiv.) as a solid. The reaction mixture was placed under argon, protected from light, and heated at 40° C. overnight. The solution was then concentrated under reduced pressure, and the resulting brown residue was redissolved in EtOAc and 2N aqueous sodium hydroxide and stirred until a white precipitate had formed. The suspension was filtered through CELITE® and the filtrate extracted with EtOAc. The pooled EtOAc phases were dried over excess sodium sulfate and the solvent removed under reduced pressure to afford 15 as a light orange powder (327 mg, 63%). Additional compound 15 (212 mg, 41%) was obtained as a light orange powder after washing the CELITE® from the initial filtration with 5% methanol in DCM and concentrating the filtrate under reduced pressure, leading to an overall quantitative yield. Reference: Seton et al., J. Chem. Res. (S) (2001) 546-48. Method 2: A solution of 14 (99.5 mg, 0.413 mmol, 1.0 equiv.) in chloroform (13 mL) and 95% ethanol (9 mL) was placed under argon. 10% palladium on charcoal (46 mg, 0.043 mmol, 0.1 equiv.) was added, and the reaction flask purged with argon. The dark suspension was then placed under dihydrogen and left to stir at room temperature overnight (16 hours). The suspension was filtered through CELITE® and the CELITE® rinsed with additional DCM and EtOH. The filtrate was concentrated in vacuo and the resulting dark orange precipitate taken up in saturated aqueous sodium bicarbonate (50 mL) and ethyl acetate (50 mL). The aqueous layer was extracted with EtOAc (3×50 mL) and combined EtOAc layers were washed with brine (20 mL), dried over excess sodium sulfate, and filtered. The filtrate was concentrated under reduced pressure to afford a pale yellow powder as clean product 15 (61 mg, 70%).

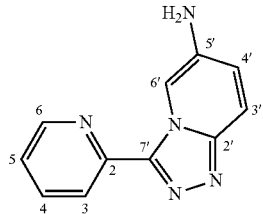

$^1$H NMR (500 MHz, CDCl$_3$*/CD$_3$OD): 7.13 (d, $^3$J=8.4 Hz, 1H, H4'), 7.33 (m, 1H, H5), 7.53 (d, $^3$J=9.2 Hz, 1H, H3'), 7.82 (t, $^3$J=7.4 Hz, 1H, H4), 8.12 (br s, 1H, H6'), 8.21 (d, $^3$J=7 0.6 Hz, 1H, H3), 8.71 (d, $^3$J=4.0 Hz, 1 H, H6). $^{13}$C NMR (100 MHz): 111.9, 115.9, 122.2, 124.3, 124.7, 136.9, 137.1, 146.9, 149.6, 149.7, 161.7. HR ESI(+): calc. for [15·H]$^+$ (C$_{11}$H$_{10}$N$_5$): 212.0936, found: 212.0920. Mp: 204-206° C. (dec.).

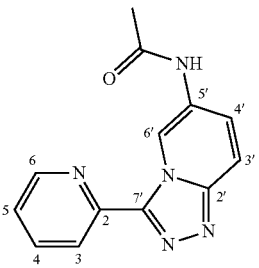 [SMILES: CC(=O)Nc1ccc2nnc(-c3ccccn3)n2c1]

$^1$H NMR (500 MHz, CDCl$_3$*/CD$_3$OD): 1.95 (s, 3H, CH$_3$), 7.16 (br dd, $^3$J=5.0 & 7.5 Hz, 1H, H5), 7.22 (dd, $^4$J=1.8 Hz, $^3$J=9.8 Hz, 1H, H4'), 7.49 (d, $^3$J=9.5 Hz, 1H, H3'), 7.67 (td, $^4$J=1.5 Hz, $^3$J=8.0 Hz, 1H, H4), 8.11 (d, $^3$J=8.0 Hz, 1H, H3), 8.53 (d, $^3$J=4.0 Hz, 1H, H6), 10.29 (s, 1H, H6'). $^{13}$C NMR (100 MHz): 22.9, 114.5, 116.7, 122.2, 123.7, 125.1, 128.1, 137.0, 144.6, 147.3, 148.7, 148.8, 170.3. Rf (SiO$_2$, acetone) =0.28. HR EI(+): calc. for [16]'+(c$_{13}$H$_{11}$N$_5$O): 253.0964, found: 253.0995; ca/c. for [16 H+—COCH$_3$H$_2$O]+ (C$_{11}$H9N5): 211.0858, found: 211.0900. Mp: 284-286° C.

Reference: Wissner et al., Bioorg. Med. Chem. Lett. (2004) 14: 1411-16.

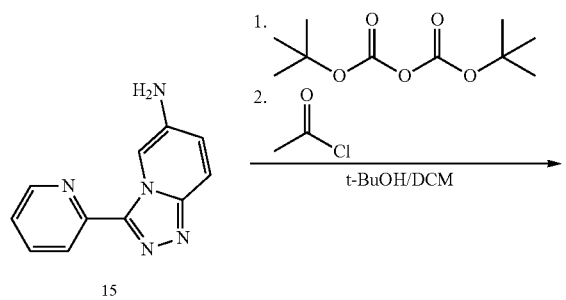

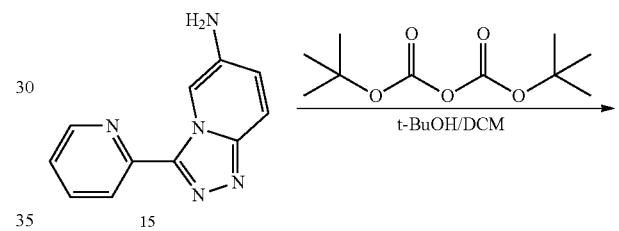

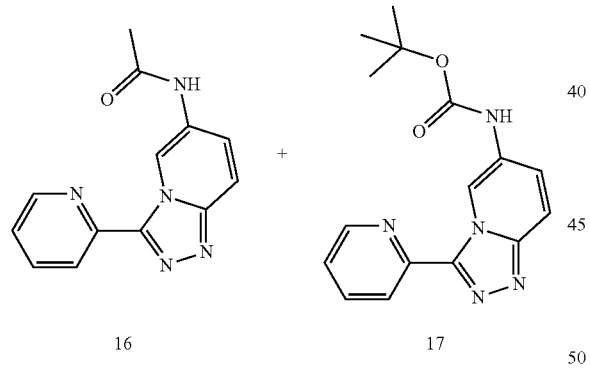

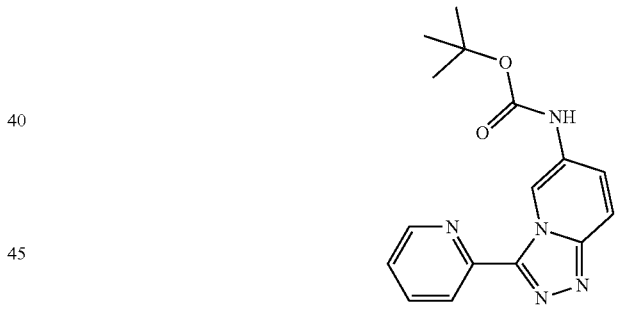

Compound 16. Di-tert-butyl dicarbonate (721 mg, 3.30 mmol, 2.6 equiv.) was added as a solid to a suspension of containing compound 15 (263 mg, 1.25 mmol, 1.0 equiv.) and trace amounts of acetyl chloride in tert-butanol (3 mL) and DCM (0.5 mL). The suspension was placed under argon, protected from light, and stirred at 40° C. for 30 hours. The reaction mixture was cooled to room temperature, diluted in hexanes and let stand at −4° C. for 48 hours. The crude product was isolated by vacuum filtration and washed with hexanes. The filtrate was concentrated down to a brown residue and the residue was dissolved in DCM and washed with water. The DCM layer was dried over excess sodium sulfate and the solvent removed in vacuo to yield additional crude product. Purification by column chromatography with gradient DCM: acetone as eluent isolated two purified compounds, 16 (13%) and 17 (50%), as pale beige powders.

Compound 17. Di-tent-butyl dicarbonate (494 mg, 2.26 mmol, 1.5 equiv.) was added as a solid to a suspension of compound 15 (318 mg, 1.51 mmol, 1.0 equiv.) in tert-butanol (4 mL) and DCM (3 mL). The suspension was then placed under argon, protected from light, and stirred at 40° C. for 48 hours. Reaction progress was monitored by TLC and additional di-tent-butyl dicarbonate (378 mg, 1.73 mmol, 1.1 equiv., for a total of 2.6 equiv.) was added after 24 hours to push the reaction to completion. The reaction mixture was cooled to room temperature, diluted in hexanes and let stand at −4° C. for 48 hours. The crude product was isolated by vacuum filtration and washed with hexanes. The filtrate was concentrated down to a brown residue and the residue taken up in DCM and washed with water. The DCM layer was dried over excess sodium sulfate and the solvent removed in vacuo to isolate additional crude product. The reaction was repeated on a similar scale (325 mg of compound 15), and the crude products combined for purification. Column chromatography with 2:1 DCM: acetone as eluent afforded purified 17 as a pale beige powder (358 mg, 38% yield).

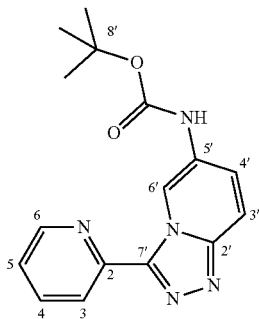 [SMILES: CC(C)(C)OC(=O)Nc1ccc2nnc(-c3ccccn3)n2c1]

¹H NMR (500 MHz, CDCl₃*/CD₃OD): δ 1.31 (s, 9H, 3 x CH₃), 7.16 (br dd, ³J=5.0 & 7.0 Hz, 1H, H5), 7.20 (br d, ³J=10 Hz, 1H, H4'), 7.46 (d, ³J=10 Hz, 1H, H3'), 7.67 (br td, ⁴J — 1.0 Hz, ³J=7.8 Hz, 1H, H4), 8.11 (d, ³J=8.0 Hz, 1H, H3), 8.56 (d, ³J=3.0 Hz, 1H, H6), 9.9 (br s, 1 H, H6'). ¹³C NMR (100 MHz): 27.8, 80.7, 114.3, 122.2, 123.5, 125.2, 129.0, 136.9, 144.4, 147.4, 148.6, 153.2. Rf (SiO₂, 2:1 DCM/acetone)=0.22. HR EI(+): calc. for [17]'⁺ ($C_{16}H_{17}N_5O_2$): 311.1382, found: 311.1378; calc. for [17 W-C(CH₃)₃]'⁺ ($C_{12}H_9N_5O_2$): 255.0756, found: 255.0859; calc. for [17 —HOC(CH₃)₃]'⁺ ($C_{12}H_7N_5O$): 237.0651, found: 238.0697; calc. for [17 H+—COOC(CH₃)₃]'+ ($C_{11}H_9N_5$): 211.0858, found: 211.0893. Mp: 226-228° C. Reference: Wissner et al., Bioorg. Med. Chem. Lett. (2004) 14: 1411-16.

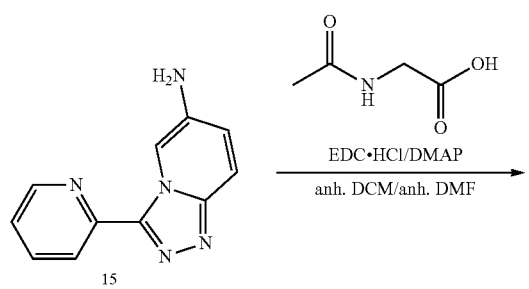

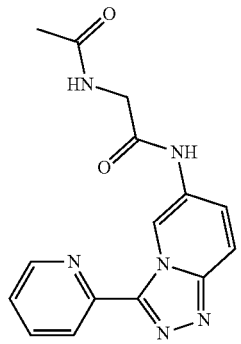

Compound 18. Pre-weighed compound 15 (25.0 mg, 0.118 mmol, 1.0 equiv.) was dried under P₂O₅ (30 min.) in a flame-dried 2-necked reaction flask. To this was added anhydrous DCM (3 mL), forming a pale yellow suspension. The reaction mixture was cooled to 0° C. in an ice bath and pre-dried (P₂O₅, 30 min.) reagents N-acetylglycine (59.0 mg, 0.504 mmol, 4.3 equiv.), DMAP (28.8 mg, 0.236 mmol, 2.0 equiv.), and EDC·HCl (91.0 mg, 0.475 mmol, 4.0 equiv.) were added as solids. The reaction was placed under argon and allowed to return to room temperature, at which point the reagents had not fully dissolved. Additional DCM (2 mL) and anhydrous DMF (0.1 mL) were therefore added. After 1 hour, a pale yellow suspension had formed. The mixture was protected from light and stirred at room temperature under argon overnight (13 hours). The suspension was then filtered and washed with MilliQ water, DCM/methanol, and diethyl ether. After drying the isolated precipitate under high vacuum (20 minutes), the product was obtained as a white powder (5.0 mg, 14%). The filtrate was washed with MilliQ water and the aqueous phase pH adjusted from 4 to 9. Extraction with EtOAc failed to produce further product but after some time, more precipitate had formed in the aqueous layer. Vacuum filtration afforded additional crude product as a white powder (22 mg, overall yield 60%). The compound was used without purification for complexation to platinum(II).

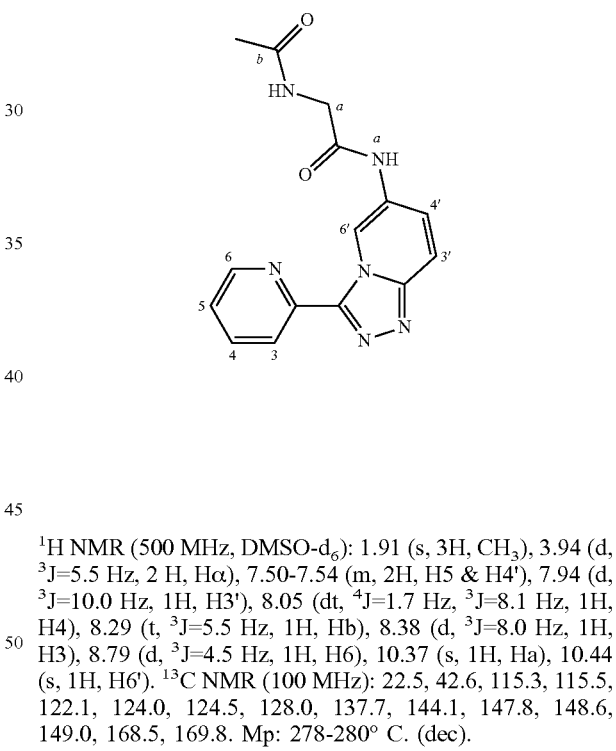

¹H NMR (500 MHz, DMSO-d₆): 1.91 (s, 3H, CH₃), 3.94 (d, ³J=5.5 Hz, 2 H, Hα), 7.50-7.54 (m, 2H, H5 & H4'), 7.94 (d, ³J=10.0 Hz, 1H, H3'), 8.05 (dt, ⁴J=1.7 Hz, ³J=8.1 Hz, 1H, H4), 8.29 (t, ³J=5.5 Hz, 1H, Hb), 8.38 (d, ³J=8.0 Hz, 1H, H3), 8.79 (d, ³J=4.5 Hz, 1H, H6), 10.37 (s, 1H, Ha), 10.44 (s, 1H, H6'). ¹³C NMR (100 MHz): 22.5, 42.6, 115.3, 115.5, 122.1, 124.0, 124.5, 128.0, 137.7, 144.1, 147.8, 148.6, 149.0, 168.5, 169.8. Mp: 278-280° C. (dec).

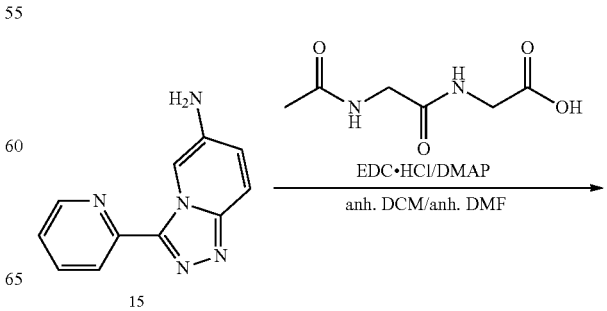

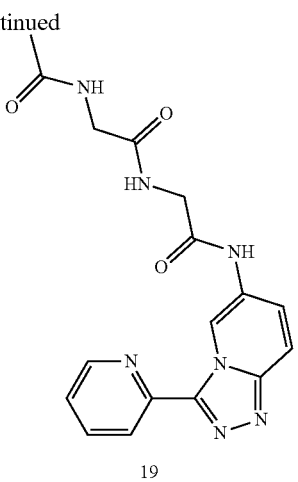

19 ethanol afforded purified 19 as a white powder (20 mg, 34% recovery) for characterization. The reaction was repeated and the crude product used without purification for complexation to platinum(II).

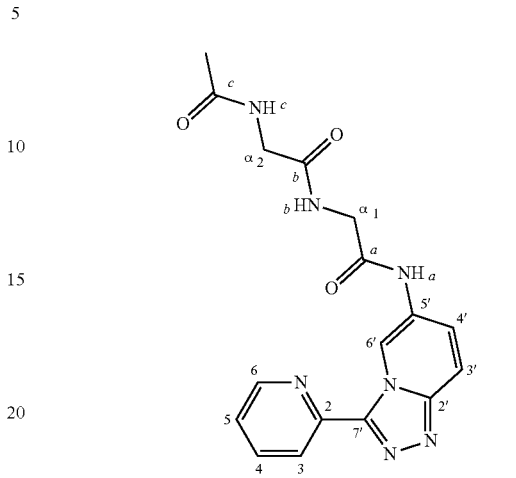

Compound 19. Pre-weighed compound 15 (98.0 mg, 0.464 mmol, 1.0 equiv.) was dried under $P_2O_5$ (30 min.) in a flame-dried 2-necked reaction flask. To this was added anhydrous DCM (13 mL), forming a pale yellow suspension. The reaction mixture was cooled to 0° C. in an ice bath and pre-dried ($P_2O_5$, 20 min.) reagents N-acetylglycyl glycine (242 mg, 1.39 mmol, 3.0 equiv.), DMAP (183 mg, 1.39 mmol, 3.0 equiv.), and EDC·HCl (356 mg, 1.86 mmol, 4.0 equiv.) were added as solids. Additional DCM (12 mL) was added, and the reaction was placed under argon and stirred at room temperature overnight. The suspension was then filtered and washed with MilliQ water, DCM, and diethyl ether. After drying the isolated precipitate under high vacuum (20 minutes), the product was obtained as an off-white powder (59.6 mg, 35%). Recrystallization from $^1$H NMR (500 MHz, DMSO-$d_6$): 1.90 (s, 3H, $CH_3$), 3.76 (d, $^3J$=5.0 Hz, 2 H, H$\alpha_2$), 3.97 (d, $^3J$=5.0 Hz, 2 H, Hai), 7.53 (t, $^3J$=6.0 Hz, 1H, H5), 7.56 (d, $^3J$=10.0 Hz, 1H, H4'), 7.94 (d, $^3J$=9.5 Hz, 1H, H3'), 8.04 (t, $^3J$=7.3 Hz, 1H, H4), 8.27 (s, 1H, Hc), 8.36-8.39 (m, 2H, H3 & Hb), 8.78 (d, $^3J$=3.0 Hz, 1H, H6), 10.21 (s, 1H, Ha), 10.45 (s, 1H, H6'). $^{13}$C NMR (100 MHz): 22.6, 42.3, 42.6, 115.4,115.5, 122.1, 124.0, 124.4, 127.9, 137.7, 144.1, 147.8, 148.6, 168.3, 169.7, 170.1. HR EI(+): calc. for [19]'+($C_{17}H_{17}N_7O_3$): 367.1393, found: 367.1399; calc. for [19-$H_2O$]+($C_{17}H_{15}N_7O_2$): 349.1287, found: 349.1325; calc. for [19·H$^+$- CO($CH_2$)NHCO($CH_3$)]+ ($C_{13}H_{12}N_6O$): 268.1073, found: 268.1233; calc. for [19-$CH_2$NHCO($CH_2$)NHCO($CH_3$)$^+$ ($C_{12}H_5N_5O$): 238.0729, found: 238.0864; calc. for [19·H+—$COCH_2$ NHCO($CH_2$)NHCO($CH_3$)]*($C_{11}H_9N_5$): 211.0858, found: 211.0983. Mp: 281-282° C.

Procedures for platinum complex formation:

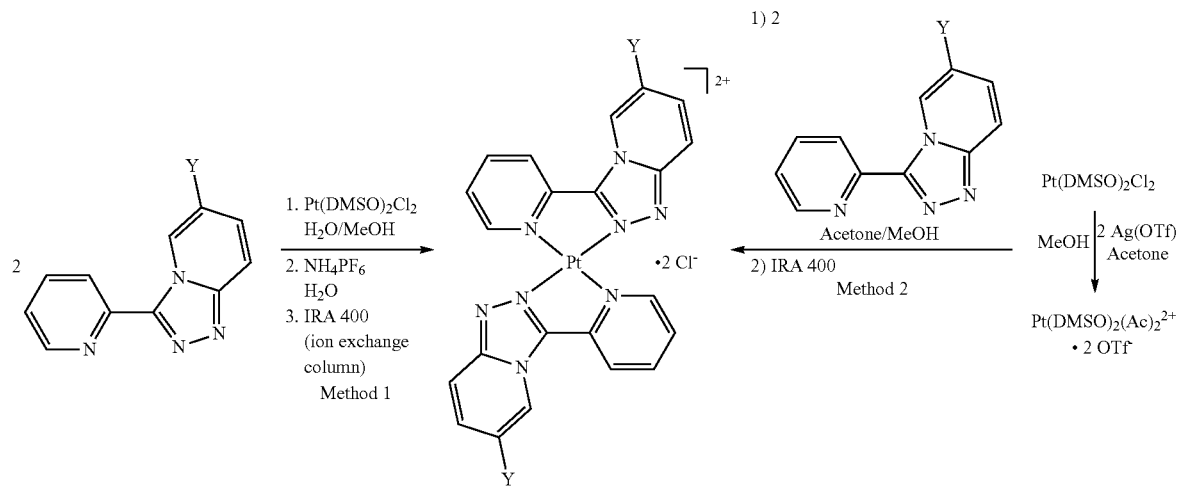

Method 1: Bis(dimethylsulfoxide)platinum(II) dichloride (1.0 equiv.) was added as a solid to a suspension of compound 15 or 16 (3.7-4.1 equiv.) in 1% water in methanol (2 mL/6 mg platinum(II) reagent). The mixture was placed under argon and stirred under reflux (70° C.) for 2.5 days. The suspension was centrifuged down and the pellet dissolved in MilliQ water. The $PF_6$ salt was precipitated out in water by addition of excess ammonium hexafluorophosphate, and the precipitate was then dissolved in a minimal volume of acetonitrile and loaded onto an anion exchange column. Elution with MilliQ water and lyophilization afforded the purified ligands as chloride salts.

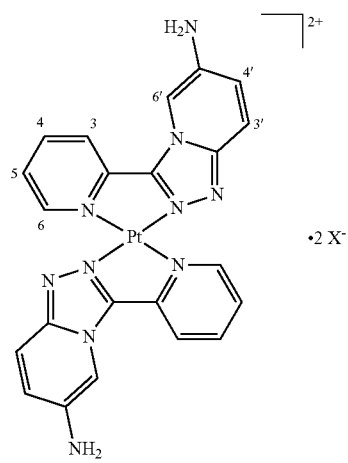

(X = $PF_6$ or Cl)

Pt(15)$_2$: $^1$H NMR of $PF_6$ salt (500 MHz, $CD_3CN$): 7.55 (d, $^3J$=9.5 Hz, 2 H, H4'), 7.91 (br m, 2 H, H5), 7.95 (d, $^3J$=9.5 Hz, 2 H, H3'), 8.13 (br s, 2H, H6'), 8.34 (d, $^3J$=7.0 Hz, 2 H, H3), 8.53 (t, $^3J$=7.0 Hz, 2 H, H4), 10.5 (br d, $^3J$=5.0 Hz, 2 H, H6). HR ESI (+) of Cl salt: calc. for [Pt(15)$_2$]$^{2+}$ ($PtC_{22}H_{18}N_{10}$): 308.5676, found: 308.5676; calc. for [Pt (15)$_2$ Cl] ($PtC_{22}H_{18}N_{10}Cl$): 652.1052, found: 653.1044; calc. for [15 H]($C_{11}H_{10}N_5$): 212.0936, found: 212.0927.

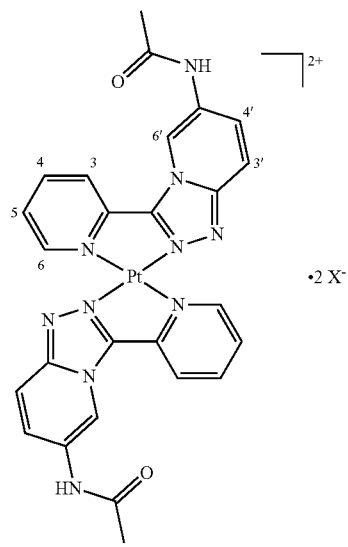

(X = $PF_6$ or Cl)

Pt(16)$_2$: $^1$H NMR of $PF_6$ Salt (500 MHz, $CD_3CN$): δ 7.75 (d, $^3J$=10.0 Hz, 2 H, H4'), 8.03 (t, $^3J$=6.3 Hz, 2 H, H5), 8.17 (d, $^3J$=10.0 Hz, 2 H, H3'), 8.36 (d, $^3J$=7.5 Hz, 2 H, H3), 8.64 (dt, $^4J$=1.3 Hz, $^3J$=8.0 Hz, 2 H, H4), 9.47 (s, 2H, NH), 9.93 (s, 2H, H6'), 10.64 (d, $^3J$=5.5 Hz, 2 H, H6). HR ESI (+) of Cl salt: calc. for [Pt(16)2]$^{2+}$ ($PtC_{26}H_{22}N_{10}O_2$): 350.5782, found: 350.5805 (100%); calc. for [16 H]+($C_{13}H_{12}N_5O$): 254.1042, found: 254.1053 (4%).

Method 2: Following the general protocol outlined herein, a solution of silver(I) triflate (2.1 equiv.) in acetone/methanol (1.1 mU 7 drops respectively per 2.9×10$^{-5}$ mol silver(I) triflate) was added to a solution of bis(dimethylsulfoxide) platinum(II) dichloride (1.0 equiv.) in acetone/methanol (0.8 mL/5 drops respectively per 1.0×10$^{-5}$ mol platinum reagent). The resulting cloudy white suspension was protected from light and stirred at room temperature (25 min.). Following this, the suspension was transferred to Eppendorf™ tubes and centrifuged down (5 min.), and the supernatant retained. The pellet (containing silver chloride) was resuspended twice in acetone, then centrifuged down, and each time the wash was added to the pooled supernatant. The supernatant solution (containing the platinum reagent) was then added to a solution of compound 17, 18, or 19 (2.9-3.3 equiv.) in acetone/methanol at either room temperature or while heating (solvent mixtures and temperatures depend on compound solubility as indicated in table below). The reaction mixture was placed under argon, protected from light, and stirred under reflux for 72 hours. A suspension was normally observed to form after 48 hours. The reaction flask was cooled to room temperature and the contents transferred to Eppendorf™ tubes or 15 mL tubes depending on reaction scale. The suspension was centrifuged down (min. 5 min.) and the pellet washed with acetonitrile (Pt(17)$_2$) or 2:1 acetonitrile:methanol (Pt(18)$_2$ and Pt(19)$_2$). The pooled supernatants were concentrated under reduced pressure to afford the product as a triflate salt. In cases where the complexes are prone to aggregation in solution as chloride salts, the triflate salt of the complex was used for NMR characterization. The triflate salt was then dissolved in a minimum amount of acetonitrile or acetonitrile/methanol and adsorbed onto anion exchange column beads (IRA 400 Cl$^-$) through slow evaporation of the organic solvent overnight. Elution with MilliQ water and lyophilization afforded the purified ligands as chloride salts.

| | 17 | 18 | 19 |
|---|---|---|---|
| Compound (mol, equiv.) | (1.02 × 10$^{-4}$, 3.0 equiv.) | (2.48 × 10$^{-5}$, 2.9 equiv.) | (8.17 × 10$^{-5}$, 3.0 equiv.) |
| Acetone/ methanol | 4 mL/4 mL Soluble at 25° C. | 2.5 mL/2.5 mL Heated to dissolve | 7 mL/7 mL Heated to dissolve |
| Yield of complex (OTf salt) | 11% (pale yellow solid) | 60% (white solid) | 26% (beige solid) |

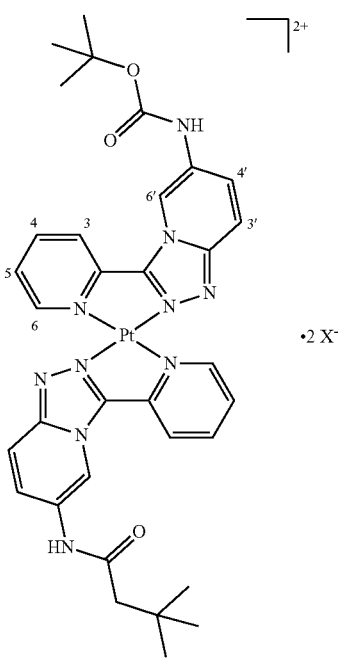

(X = OTf or Cl)

Pt(17)$_2$: $^1$H NMR of OTf salt (400 MHz, CD$_3$CN): 1.58 (s, 18H, CH$_3$), 7.77 (dd, $^4$J=1.6 Hz, $^3$J=10.0 Hz, 2 H, H4'), 8.03 (m, 2H, H5), 8.14 (d, $^3$J=10.0 Hz, 2 H, H3'), 8.32 (d, $^3$J=8.0 Hz, 2 H, H3), 8.64 (td, $^4$J=1.2 Hz, $^3$J=8.0 Hz, 2 H, H4), 9.44 (s, 2H, H6'), 10.63 (d, $^3$J=5.2 Hz, 2 H, H6). HR ESI (+) of Cl salt: calc. for [Pt(17)2]$^{2+}$(PtC$_{32}$H$_{34}$N$_{10}$O$_4$): 408.6201, found: 408.6237 (100%).

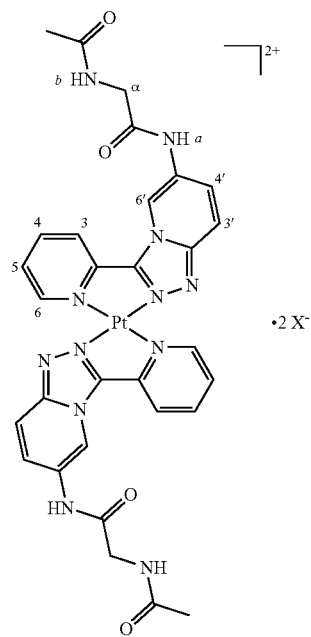

(X = PF$_6$ or Cl)

Pt(O 8)$_2$: $^1$H NMR of PF$_6$ salt (500 MHz, CD$_3$CN): 2.06 (s, 6H, CH$_3$), 4.07 (d, $^3$J=6.0 Hz, 4 H, Hα), 7.29 (br t, $^3$J=5.3 Hz, 2 H, NHb), 7.77 (dd, $^4$J=1.3 Hz, $^3$J=9.8 Hz, 2 H, H4'), 8.03 (t, $^3$J=6.8 Hz, 2 H, H5), 8.14 (d, $^3$J=9.5 Hz, 2 H, H3'), 8.29 (d, $^3$J=8.0 Hz, 2 H, H3), 8.76 (t, $^3$J=8.0 Hz, 2 H, H4), 9.76 (s, 2H, H6'), 10.44 (d, $^3$J=5.0 Hz, 2 H, H6). HR ESI (+) of Cl salt: ca/c. for [Pt(18)2]$^{2+}$(PtC$_{30}$H$_{28}$N$_{12}$O$_4$): 407.5997, found: 407.5997 (58%); ca/c. for [18 H](C$_{13}$H$_{13}$N$_4$): 311.1256, found: 311.1244 (3%).

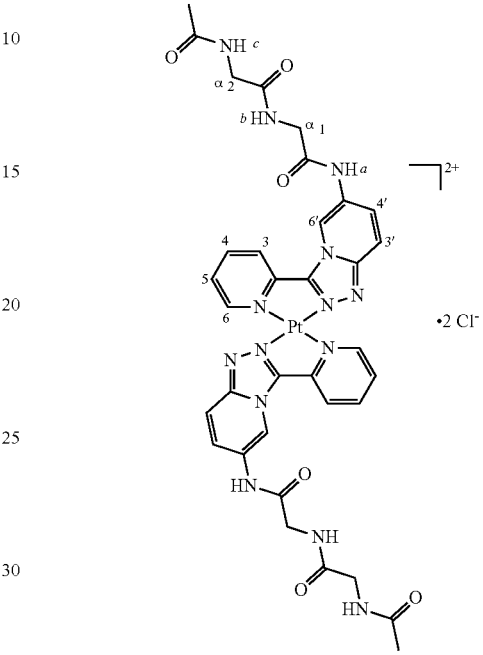

Pt(19)$_2$: $^1$H NMR of Cl salt (500 MHz, D$_2$O with t-BuOH as internal reference): 2.14 (s, 6H, CH3), 4.11 (s, 4H, Hα$_1$), 4.28 (s, 4H, Hα$_2$), 7.80 (d, $^3$J=9.5 Hz, 2 H, H4'), 7.90 (br t, $^3$J=6.0 Hz, 2 H, H5), 8.07 (d, $^3$J=9.5 Hz, 2 H, H3'), 8.35 (d, $^3$J=5.5 Hz, 2 H, H3), 8.65 (t, $^3$J=7.3 Hz, 2 H, H4), 9.49 (s, 2H, H6'), 10.02 (br s, 2H, H6). HR ESI (+) of Cl salt: calc. for [Pt(19)$_2$]$^{2+}$(PtC$_{34}$H$_{34}$N$_{14}$O$_6$): 464.6211, found: 464.6243 (100%); calc. for [19 H]+(C$_{17}$H$_{18}$N$_7$O$_3$): 368.1471, found: 368.1486 (2%).

Example 1D. Monofunctional Platinum Complex, Prepared with Mixed Ligands

Complex Pt(2)(4) was prepared in two steps: (i) isolation of a 1:1 Pt(4) complex (which likely exists as a dimer), then (ii) introduction of the ligand 2 to form a dissymmetric Pt(2)(4) complex. To a solution of ligand 4 (100 mg, 3.6×10$^4$ mol, 3.8 equiv.) in methanol (9 mL) was added platinum bisdimethylsulfoxide dichloride (41.3 mg, 9.8×10$^{-5}$ mol) as a solid, followed by distilled water (0.1 mL). The mixture was refluxed for 2.5 days. The resulting yellow solid was filtered to give 30 mg of intermediate used in the following step directly. The intermediate (10 mg) was suspended in methanol (5 mL) and heated at reflux. To the hot mixture was added a solution of silver triflate (9.6 mg, 3.8×10$^{-5}$ mol) in a mixture of acetone (1.5 mL) and methanol (3 drops). The mixture was heated at reflux for 4 h protected from light. The resulting grey solid was centrifuged, and yellow supernatant separated. The grey precipitate was washed with methanol (3×1 mL) and the washes were combined with the yellow supernatant. To this yellow solution was then added ligand 2 (3.82 mg, 1.95×10$^{-5}$ mol, 0.5 equiv. vs silver salt) in a mixture of acetone (1.5 mL) and methanol (2 mL). The resulting light yellow solution was refluxed for 28 h protected from light, concentrated under vacuo, taken up in dichloromethane and filtered to give 11 mg of an ocre powder. $^1$H NMR analysis (300 MHz, CD$_3$CN+4 drops of CD$_3$OD) reveals the formation of Pt(2)(4) (50%) together with Pt(4)2 (25%) and Pt(2)2 (25%).

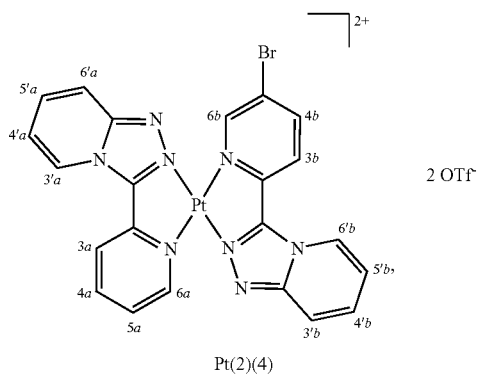

Pt(2)(4)

Pt(2)(4): $^1$H NMR of OTf salt (300 MHz, CD$_3$CN+4 drops of CD$_3$OD): 10.8 (br d, 1 H, H6b), 10.7 (d, $^3$J=7 Hz, 1H, H6a), 9.00 (d, $^3$J=7 Hz, 1H, H6' a or H6'b), 8.91 (d, $^3$J=7 Hz, 1H, H6'b or H6' a), 8.82 (d, $^3$J=8 Hz, 1 H, H4b), 8.55-8.65 (m, 2H, H4a+H3a), 8.48 (d, $^3$J=8 Hz, 1H, H3b), 8.29 (d, $^3$J=9 Hz, 1 H, H3' a or H3'b), 8.24 (d, $^3$J=9 Hz, 1H, H3'b or H3' a), 8.07 (br t, $^3$J=6 Hz, 1H, H5a), 7.8-7.9 (m, 2 H, H4' a+H4'b), 7.6-7.7 (m, 2 H, H5' a+H5'b). HR-ESI MS (+) of triflate salt: calc. for [PtC$_{22}$H$_1$5BrN$_8$]$^{2+}$: 332.5125, found: 332.5107 (100%).

Example 2. Fluorescence Resonance Energy Transfer (FRET) Melting Temperature Studies 96-Well plate FRET melting assays were adapted from literature protocols (A. De Rache, J.-L. Mergny, Biochimie (2015),115: 194-202) and conducted using a Strategene Mx3005P real-time PCR apparatus. G4 oligonucleotides labelled with 5'-FAM (6-carboxyfluorescein) and 3'-TAMRA (6-carboxytetramethylrhodamine) fluorophores were folded by rapid annealing in buffer (2 min. at 90° C. followed by cooling in ice). The FAM fluorescent tag was excited at 492 nm and its emission followed at 516 nm while the plates were incubated at 25° C. (5 min.) and then heated (1° C./min) to 95° C. Each condition was repeated in duplicate, and every experiment was repeated at least three times for reproducibility. Final oligonucleotide concentration (0.1 pM) and buffer conditions (10 mM lithium cacodylate, pH 7.2 with either 10 mM potassium chloride/90 mM lithium chloride or 100 mM sodium chloride for DNA, or with 1 mM potassium chloride and 99 mM lithium chloride for RNA) were kept constant. $T_{1/2}$ values were obtained as the temperature at which the normalized fluorescence emission is 0.5, with $\Delta T_{1/2} = T_{1/2}$ (G4+ binder) — $T_{1/2}$ (G4). For competition assays (see FIG. 2), the same method was followed in the absence or presence of a DNA duplex (ds26, 0-5 µM) which was not labelled with fluorophores. Results of these studies are shown in Table 2 and FIG. 2.

Example 3. Circular Dichroism (CD) Studies

500 µL Aliquots of 22AG and c-myc were folded at 3 µM by rapid annealing (2 min. at 90° C. followed by cooling in ice) in 10 mM lithium cacodylate (pH 7.2) and 100 mM potassium chloride. G4 binders were prepared in the same buffer at 37.5 or 75 µM, such that 0.5 equiv. binder was equivalent to 10 or 20 µL additions. Spectra at 0, 0.5, 1.0, 1.5, 2.0, 3.0, and 5.0 equivalents of binder added to G4 were acquired after 15 minutes of equilibration. Each spectrum was collected using a Jasco J-815 spectrometer with the following experimental parameters: wavelength range: 200-500 nm, data pitch: 1 nm, D.I.T.: 0.5 s, scan speed: 100 nm/min, accumulations: 3. Acquired data was then blank-corrected and baseline-corrected. Curves were smoothed by taking the average of the ellipticity data from the preceding 4 wavelengths as well as the current wavelength.

Example 4. FID Studies

FID assays were adapted from literature protocols (Monchaud et al., Biochimie (2008) 90: 1207-23). Each FID experiment was repeated three times for reproducibility using one or both method(s) listed below. In both cases the fluorophore used was thiazole orange (TO), a chromophore which does not fluoresce in the bulk solvent but becomes strongly fluorescent upon binding to quadruplex and duplex structures. In order to derive binding constants from FID data, fluorescence titrations monitoring the binding of TO to the quadruplex examined were first performed in triplicate. A TO-G4 binding constant was determined by data fitting using the HypSpec2014 software (see below).

a) Preparation of Oligonucleotides

Intramolecular G4 and duplexes (22AG, c-myc, ds26) were annealed at 50 µM by heating at 90° C. (5 min.) in 10 mM lithium cacodylate (pH 7.2) and 100 mM KOI and were stored on ice immediately.

b) Individual FID Titration Format

Experiments were performed in a 1.5 mL cell at 25° C. 0-15 equivalents of ligand was titrated into an initial solution of thiazole orange (0.50 µM) and pre-folded DNA (0.25 µM). Following a 3 minute equilibrium period after each addition, the fluorescence emission spectrum was recorded ($\lambda_{ex}$=501 nm, $\lambda_{em}$=510-750 nm, bandwidth 5 nm, step size 1 nm). Data was collected using Horiba FluoroMax-4.0 and PTI QuantaMaster Model 2 spectrofluorimeters.

c) High-Throughput FID Format

Samples with a final volume of 300 µL were prepared in a quartz 96-well plate by addition of (i) thiazole orange (40 µM), (ii) 22AG (20 µM), (iii) binder (18.8 µM), and (iv) buffer. Final concentrations were 1.0 µM, 0.5 µM, and 0-7.5 µM respectively. Data points were collected at 0, 0.125, 0.25, 0.38, 0.50, 0.63, 0.75, 1.0, 1.25, 1.50, 1.75, 2.0, 2.5, 3.0, 4.0, 5.0, 7.5, 10.0, 12.5, and 15.0 equivalents of binder. Volumes of addition for a single experiment were as listed in the diagram below. Control samples including (i) buffer, (ii) TO alone, (iii) TO with binder, and (iv) binder alone were also prepared.

| | 1 | 2 | 3 | 4 | 5 | 6 | 7 | 8 | 9 | 10 | 11 | 12 |
|---|---|---|---|---|---|---|---|---|---|---|---|---|
| A | 300 | 7.5 | 7.5 | 240 | 7.5 | | | | → | | | |
| | | 293 | 52.5 | 60 | 7.5 | | | | → | | | |
| | | | | | 285 | 2 | 4 | 6 | 8 | 10 | 12 | 16 |
| | | | | | | 283 | 281 | 279 | 277 | 275 | 273 | 269 |

-continued

| | 1 | 2 | 3 | 4 | 5 | 6 | 7 | 8 | 9 | 10 | 11 | 12 |
|---|---|---|---|---|---|---|---|---|---|---|---|---|
| B | 7.5 | | | | | → | | | | | | |
| | 7.5 | | | | | → | | | | | | |
| | 20 | 24 | 28 | 32 | 40 | 48 | 64 | 80 | 120 | 160 | 200 | 240 |
| | 265 | 261 | 257 | 253 | 245 | 237 | 221 | 205 | 165 | 125 | 85 | 45 |

Note
that indicated volumes for TO, DNA, binder, and buffer were in units of microlitres Note that indicated volumes for TO, DNA, binder, and buffer were in units of microlitres.

A blank sample containing only buffer was measured in a 1.5 mL fluorescence cuvette to serve as reference. Fluorescence emission spectra were collected at 25° C. using a Spectromax M2 platereader with experimental parameters as follows: $\lambda_{ex}$=501 nm, with cutoff at 515 nm; $\lambda_{em}$=510-700 nm; Step size: 1 nm, PMT: medium; Autocalibrate: on; Number of reads per data point: 6.

d) Data fitting

For binding constant determination, the original fluorescence data was blank corrected and imported as composite titration (individual format) or batch (high-throughput format) data files into HypSpec2014 (Gans et al., Talanta (1996) 43: 1739-53), along with the blank-corrected spectrum of free TO at a known concentration. During refinement, the previously determined binding constant for the TO-G4 complex was kept constant, and it was assumed that the TO-G4 complex and any intermediate TO-G4-binder complexes were luminescent. Data fitting was performed independently on the three experiments to avoid introducing systemic errors. Error was calculated as error=3 x σ x standard deviation, where a (a measure of goodness of fit) and standard deviation were values provided by the software after refinement. For a comparison of complexes in which the stoichiometry (number of binders relative to 22AG) was not the same, the association of each binder (0-5 μM with 22AG (2 μM) was modelled using HySS computational software (Alderighi et al., Coord. Chem. Rev. (1999) 184: 311-18). This provided a percentage of complex formed when the binder was present in the binder: 22AG molar ratio consistent with the experimentally determined complex stoichiometry (see Table 4).

Example 5. Cancer Cell Growth Inhibition Studies

Cancer cell growth inhibition studies were performed through the US National Cancer Institute (NCI) 60 human tumour cell line anticancer drug screening platform. $[Pt(2)_2](OTf)_2$, $[Pt(8)_2](PF_6)_2$, and $[Pt(11)_2](PF_6)_2$ were accepted for testing at the one-dose screen. For experimental details, see Holbeck et al., Mol Cancer. Ther. (2010) 9:1451-60, as well as https://dtp.cancer.gov/discovery_development/nci-60/methodology.htm.

All publications listed and cited herein are incorporated herein by reference in their entirety. It will be understood by those skilled in the art that this description is made with reference to certain embodiments and that it is possible to make other embodiments employing the principles which fall within its spirit and scope as defined by the claims.

TABLE 1

Structural Formulae of Binders including Reference Binder

| Name | Structural Formulae |
|---|---|
| $Pt(2)_2$ | |
| $Pt(4)_2$ | |
| $Pt(6)_2$ | |
| $Pt(7)_2$ | |

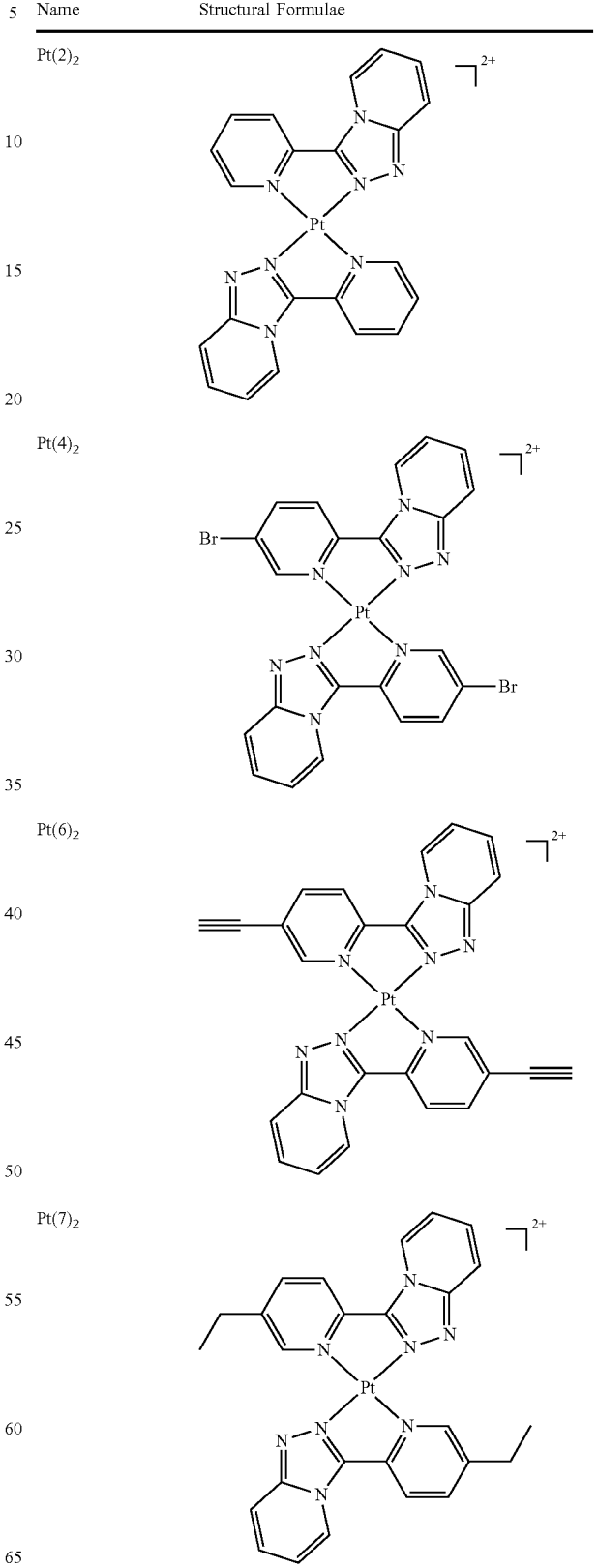

TABLE 1-continued
Structural Formulae of Binders including Reference Binder
| Name | Structural Formulae |
|---|---|
| Pt(8)$_2$ | 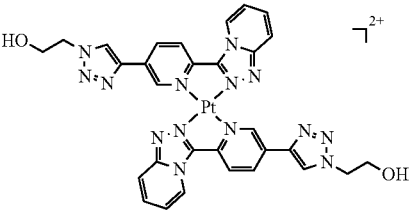 |
| Pt(10)$_2$ | 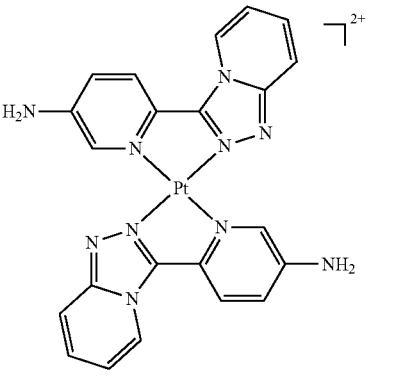 |
| Pt(11)$_2$ | 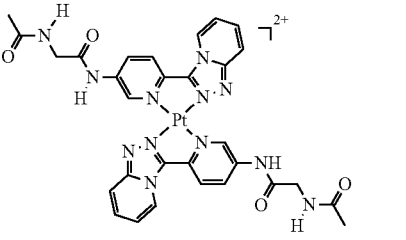 |
| Pt(15)$_2$ | 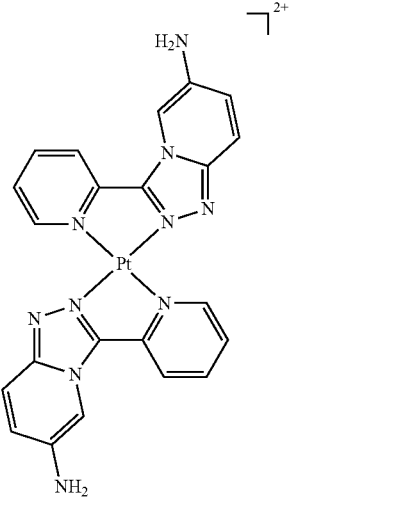 |
| Pt(16)$_2$ | 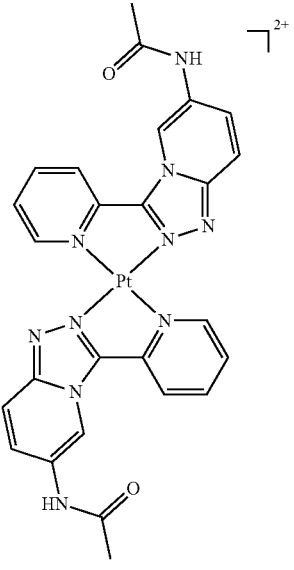 |
| Pt(17)$_2$ | 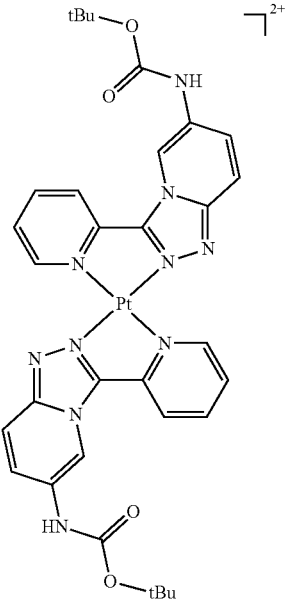 |

TABLE 1-continued
Structural Formulae of Binders including Reference Binder
| Name | Structural Formulae |
|---|---|
| Pt(18)$_2$ | 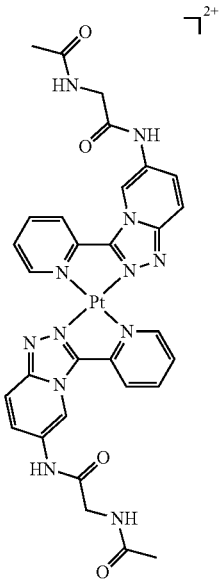 |
| Pt(19)$_2$ | 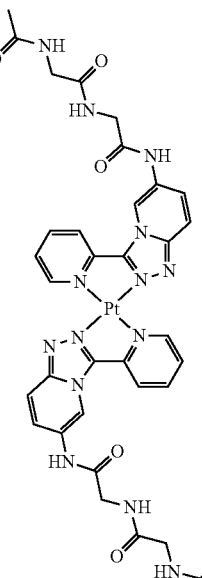 |
| Pt(21)$_2$ | 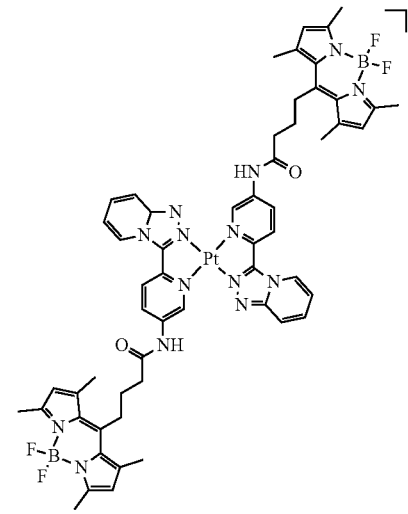 |
| Pt(22)$_2$ | 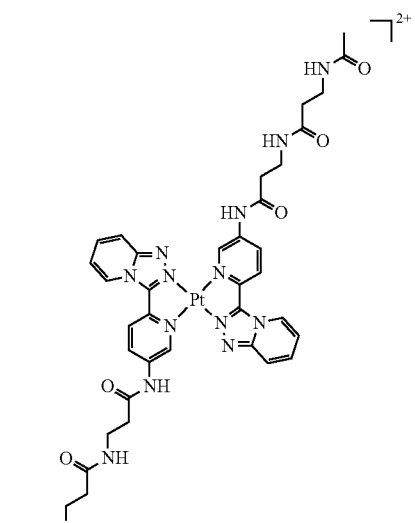 |
| Pt(2)(4) | 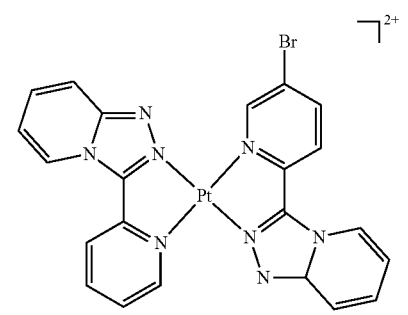 |

TABLE 1-continued

Structural Formulae of Binders including Reference Binder

| Name | Structural Formulae |
|---|---|
| Phen-DC3 Reference binder (not included in compounds of Formula (1)) | [Chemical structure: phenanthroline dicarboxamide with two quinolinium groups, •2 OTf⁻] |

TABLE 2

Oligonucleotide sequences used in FRET, CD, and FID studies of G4 binders[1]

| Name | Fluor labelled 5'-Sequence-3' | RNA or DNA | 5'-Sequence-3' and SEQ ID NO |
|---|---|---|---|
| F21RT | fam-GGG UUA GGG UUA GGG UUA GGG-tamra | RNA | GGG UUA GGG UUA GGG UUA GGG (SEQ ID NO: 1) |
| F21T | fam-GGG TTA GGG TTA GGG TTA GGG-tamra | DNA | GGG TTA GGG TTA GGG TTA GGG (SEQ ID NO: 2) |
| 22AG | A GGG TTA GGG TTA GGG TTA GGG | DNA | A GGG TTA GGG TTA GGG TTA GGG (SEQ ID NO: 3) |
| F21CTAT | fam-GGG CTA GGG CTA GGG CTA GGG-tamra | DNA | GGG CTA GGG CTA GGG CTA GGG (SEQ ID NO: 4) |
| F25cebT | fam-A GGG T GGG TGT AAG TGT GGG T GGG T-tamra | DNA | A GGG T GGG TGT AAG TGT GGG T GGG T (SEQ ID NO: 5) |
| FBom17T | fam-GG TTA GGT TAG GTT GG-tamra | DNA | GG TTA GGT TAG GTT GG (SEQ ID NO: 6) |
| Fc-mycT | fam-TTGA GGG T GGG TA GGG T GGG TAA-tamra | DNA | TTGA GGG T GGG TA GGG T GGG TAA (SEQ ID NO: 7) |
| c-myc | TGA GGG TGG GTA GGG TGG GTA A | DNA | TGA GGG TGG GTA GGG TGG GTA A (SEQ ID NO: 8) |
| FTBAT | fam-GGT TGG TGT GGT TGG-tamra | DNA | GGT TGG TGT GGT TGG (SEQ ID NO: 9) |
| FdxT | fam-TAT AGC TAT A-(OCH₂CH₂)₆-T ATA GCT ATA-tamra | DNA | TAT AGC TAT A (SEQ ID NO: 10) TATA GCT ATA (SEQ ID NO: 11) |
| ds26 | CAA TCG GAT CGA ATT CGA TCC GAT TG | DNA | CAA TCG GAT CGA ATT CGA TCC GAT TG (SEQ ID NO: 12) |

[1]Guanines involved in G4 tetrads indicated in bold. fam (6-carboxyflourescein) and tamra (6-carboxytetramethylrhodamine) are fluorophores used in FRET experiments.

TABLE 3

Stabilization of Quadruplex and Duplex Melting Temperatures by Binders as determined by FRET Melting Assays Average Binder-Induced Stabilization of Melting Temperature (±std. deviation, ° C.) for RNA/DNA Stuctures[1]

| Binder | Quadruplex | | | | | | | Duplex |
|---|---|---|---|---|---|---|---|---|
|  | F21RT | F21T | F21CTAT | FBom17T | FTBAT | Fc-mycT | F25cebT | FdxT |
| Phen-DC3 | 13.3 ± 0.5 | 16.4 ± 1.4 | 11.7 ± 0.3 | 3.2 ± 1.4 | 6.4 ± 0.7 | 11.3 ± 0.2 | >8.5 ± 0.3 | 0.6 ± 0.5 |
| Pt(2)₂ | 21.0 ± 1.5 | 22.9 ± 0.5 | 16.6 ± 1.5 | 7.9 ± 0.4 | 12.6 ± 2.6 | >10.9 ± 0.3 | >11.5 ± 0.4 | −0.7 ± 0.3 |
| Pt(4)₂ | >14.4 ± 0.5 | >19.0 ± 2.6 | >8.9 ± 0.8 | 3.5 ± 0.3 | 5.6 ± 1.2 | >4.5 ± 1.6 | >8.7 ± 0.2 | −0.9 ± 0.4 |
| Pt(6)₂ | 4.5 ± 0.6 | 0.9 ± 0.6 | 1.9 ± 0.4 | 0.7 ± 0.2 | 1.8 ± 0.6 | 0.2 ± 2.0 | 0.9 ± 0.3 | 0.4 ± 0.4 |
| Pt(7)₂ | >18.5 ± 0.6 | >25.3 ± 2.0 | >15.6 ± 1.0 | 4.4 ± 0.8 | 26.6 ± 0.6 | >10.0 ± 1.5 | >12.6 ± 0.4 | −0.9 ± 0.5 |
| Pt(8)₂ | 18.9 ± 0.4 | >23.3 ± 1.7 | >11.7 ± 1.5 | 3.0 ± 0.6 | 13.6 ± 2.5 | >8.1 ± 1.3 | >13.3 ± 0.7 | −1.0 ± 0.4 |
| Pt(10) | >20.7 ± 1.4 | >31.2 ± 1.0 | >24.1 ± 0.6 | 19.8 ± 0.7 | 8.3 ± 1.3 | >11.6 ± 1.8 | >16.7 ± 0.6 | 1.7 ± 1.1 |
| Pt(11)₂ | >19.7 ± 0.9 | >27.3 ± 0.3 | >16.5 ± 2.5 | 5.3 ± 0.7 | 7.9 ± 3.5 | >11.3 ± 1.4 | >15.1 ± 0.3 | −1.2 ± 0.3 |
| Pt(15)₂ | >19.0 ± 2.5 | >16.5 ± 2.8 | >14.7 ± 1.2 | 2.2 ± 3.6 | 4.9 ± 0.5 | >7.1 ± 1.6 | >9.3 ± 0.6 | 0.3 ± 0.5 |
| Pt(16)₂ | >16.6 ± 3.2 | >15.4 ± 2.0 | >10.9 ± 1.4 | 1.8 ± 0.8 | 7.8 ± 1.0 | >7.2 ± 0.8 | >15.5 ± 0.5 | 0 ± 0.4 |

[1]Experimentally determined average melting temperatures of oligonucleotide quadruplex or duplex in the absence of binder are as follows: F21RT 57.4 ± 0.7° C.; F21T 54.1 ± 1.0° C.; F21CTAT 58.6 ± 0.4° C.; FBom17T 50.1 ± 1.1° C.; Fc-mycT 67.5 ± 0.4° C.; F25cebT 69.3 ± 0.2° C.; FdxT 66.8 ± 0.5° C. Values are consistent with the literature (De Rache, A., Mergny, J.-L. Biochimie (2015) 115: 194-202).

TABLE 4

Quantification of binding to guanine quadruplex 22AG in K buffer through fitting of FID data

| G4 | Binder | Number (n) of Binders In Complex with G4 After Displacement of Fluorophore | Average Log(β)[1] | Complex Formed at a Binder:G4 Molar Ratio of n:1 (%)[2] |
|---|---|---|---|---|
| 22AG (0.5 μM) | Phen-DC3 | 2 | 16.0 ± 1.3 | 93.1 ± 5.3 |
| | Pt(2)$_2$ | 2 | 14.7 ± 0.2 | 85.7 ± 0.2 |
| | Pt(7)$_2$ | 1 | 8.6 ± 0.3 | 92.4 ± 2.7 |
| | Pt(8)$_2$ | 1 | 8.2 ± 0.2 | 89.6 ± 1.4 |
| | Pt(11)$_2$ | 2 | 15.4 ± 0.8 | 91.6 ± 4.6 |

[1] β is defined as the association constant of the specified complex in units of $M^{-1}$ (1:1 binder:G4 complex) or $M^{-2}$ (2:1 complex), with error determined as 3σ × standard deviation (σ is a goodness of fit value generated during data fitting in HypSpec2014).
[2] Species distribution curves were calculated using HySS at a G4 concentration of 0.5 μM, and the value expressed was determined as the average of the upper and lower limits of the log(β) value.
Error represents standard deviation.

TABLE 5

Cancer cell lines used in NCI-60 screening of novel binders

| Cancer | Cell Lines in NCI-60 Screening[1] | Cell Lines with Binder-Induced Inhibited Growth |
|---|---|---|
| Brain | SF-268, SF-295, SF-539, SNB-19, SNB-75, U251, (SNB78, XF 498) | |
| Breast | MCF7, MDA-MB-231/ATCC, MDA-MB-468, HS578T, BT-549, T-47D | |
| Colon | COLO 205, HCC-2998, HCT-116, HCT-15, HT29, KM12, SW-620, (DLD-1, KM20L2) | |
| Kidney | 786-0, A498, ACHN, CAKI-1, RXF 393, SN12C, TK-10, UO-31, (RXF-631, SN12K1) | A498 |
| Leukemia | CCRF-CEM, HL-60(TB), K-562, MOLT-4, RPMI-8226, SR, (P388, P388/ADR) | |
| Lung | A549/ATCC, EKVX, HOP-62, HOP-92, NCI-H226, NCI-H23, NCI-H322M, NCI-H460, NCI-H522, (LXFL-529, DMS114, SHP-77) | A549/ATCC NCI-H522 |
| Melanoma | LOX-IMVI, MALME-3M, M14, MDA-MB-435, SK-MEL-2, SK-MEL-28, SK-MEL-5, UACC-257, UACC-62, (RPMI-7951, M19-MEL) | UACC-257 |
| Ovarian | IGR-OV1, OVCAR-3 to 5, OVCAR-8, NCI/ADR-RES, SK-OV-3 | SK-OV-3 |
| Prostate | PC3, DU-45 | |

[1] Additional cancer cell lines currently in use for screening are listed in brackets

We claim:
1. A compound that has general formula (1):

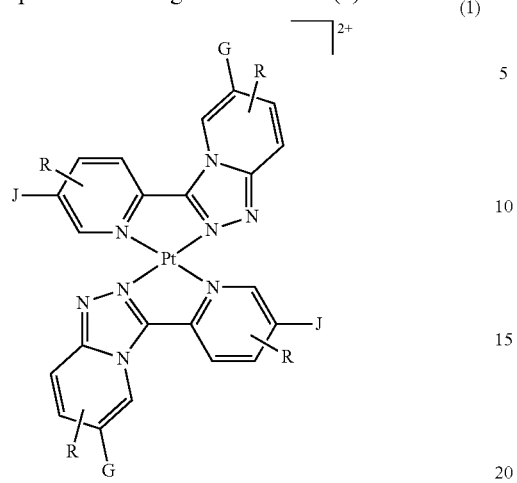

or a salt or prodrug thereof, wherein
G and J are independently a moiety selected from hydrogen, amino, alkyl, alkenyl, alkynyl, halo, amido, aryl, (heteroaryl, hydroxyl, ether, carboxyl, ester, boryl, or a combination thereof;

R is independently H, halo, aliphatic, amido, amino, hydroxyl, carboxyl, ester, ether, aryl, (heteroaryl, or a combination thereof.

2. The compound of claim 1, wherein the compound of Formula (1) comprises:

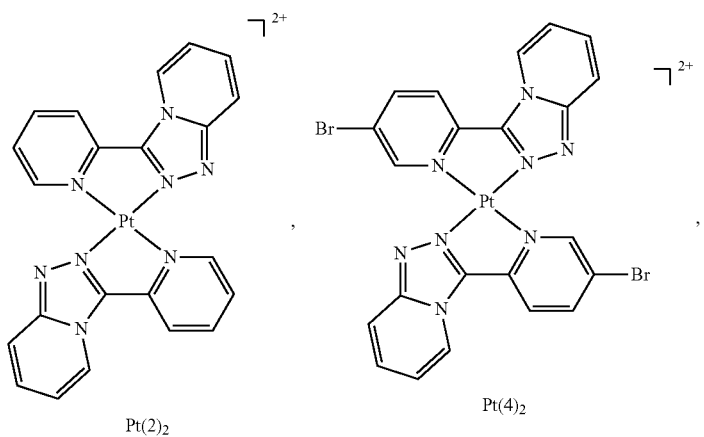

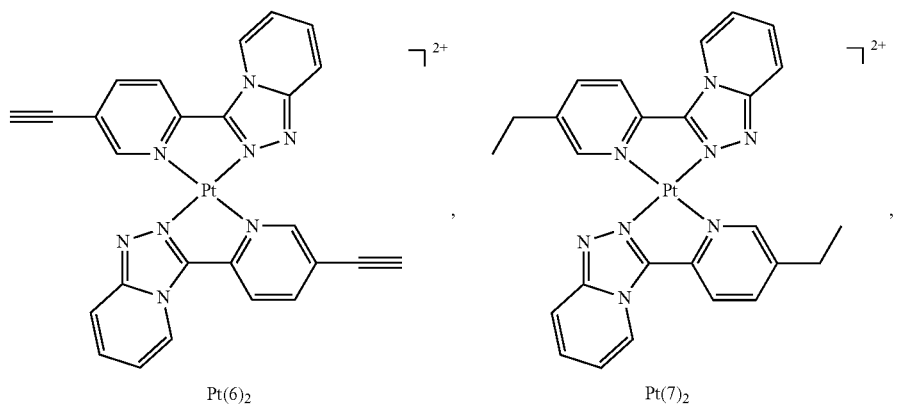

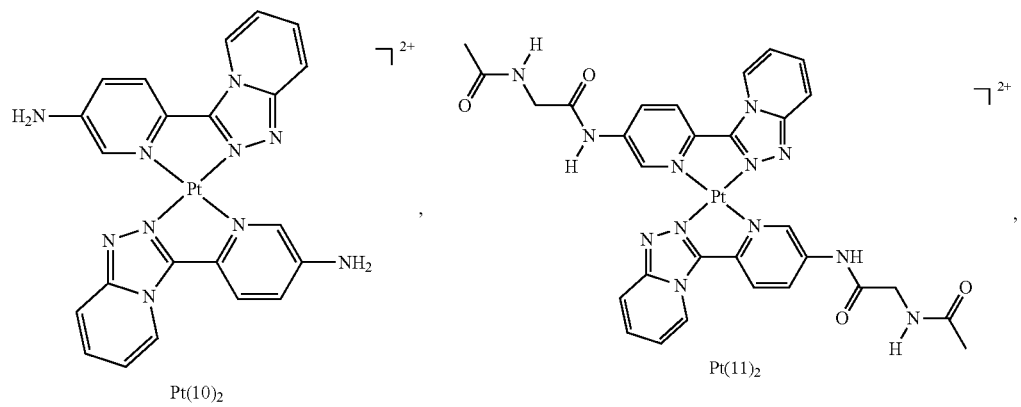
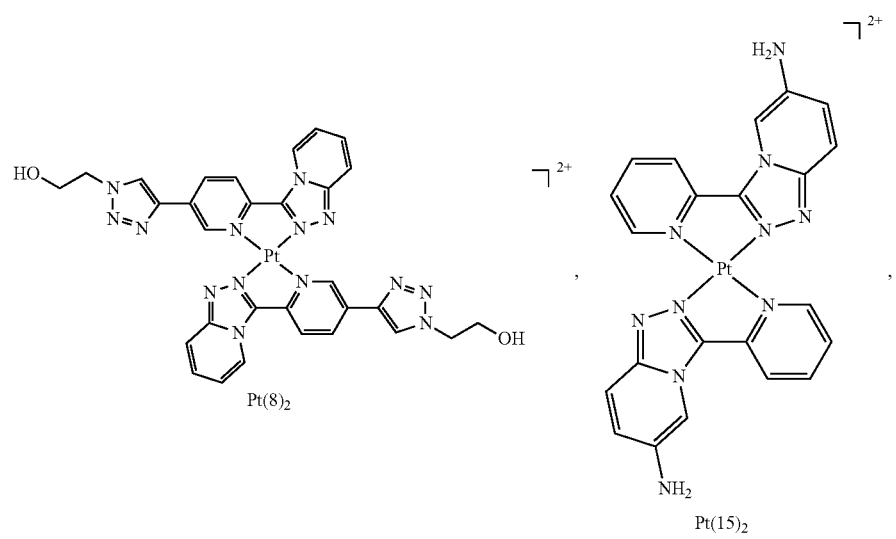

-continued
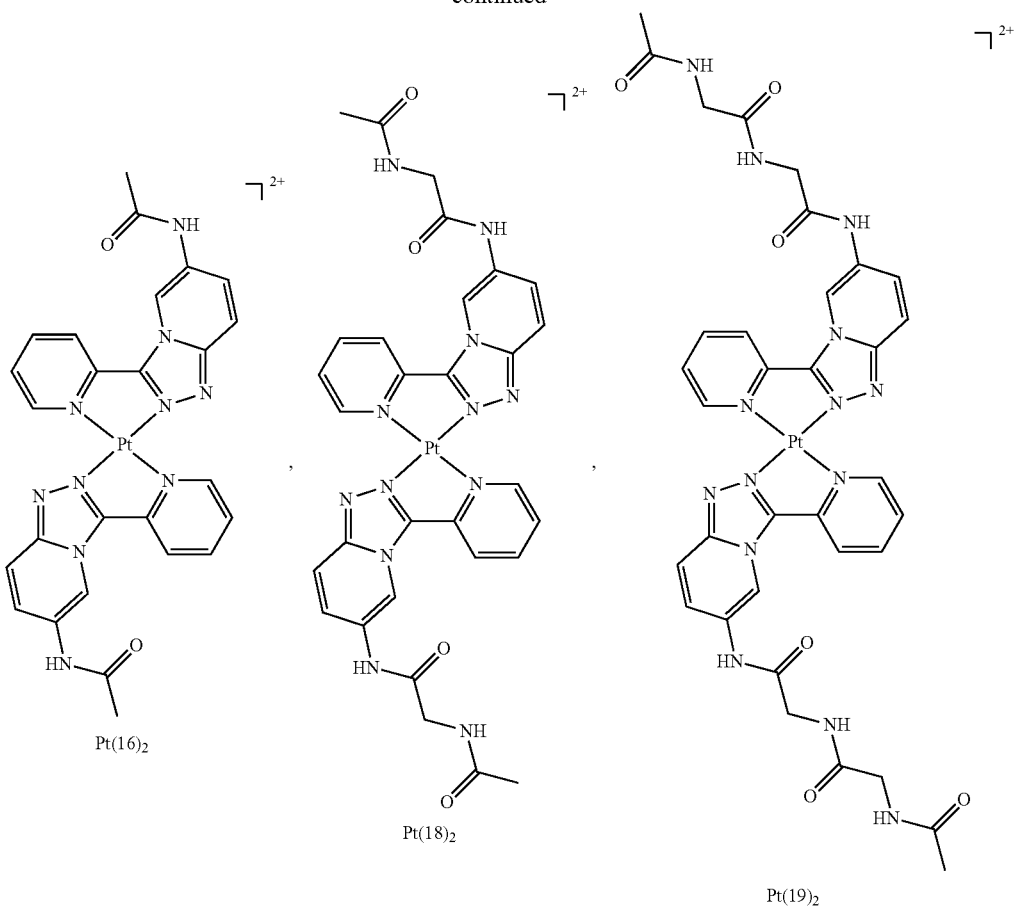
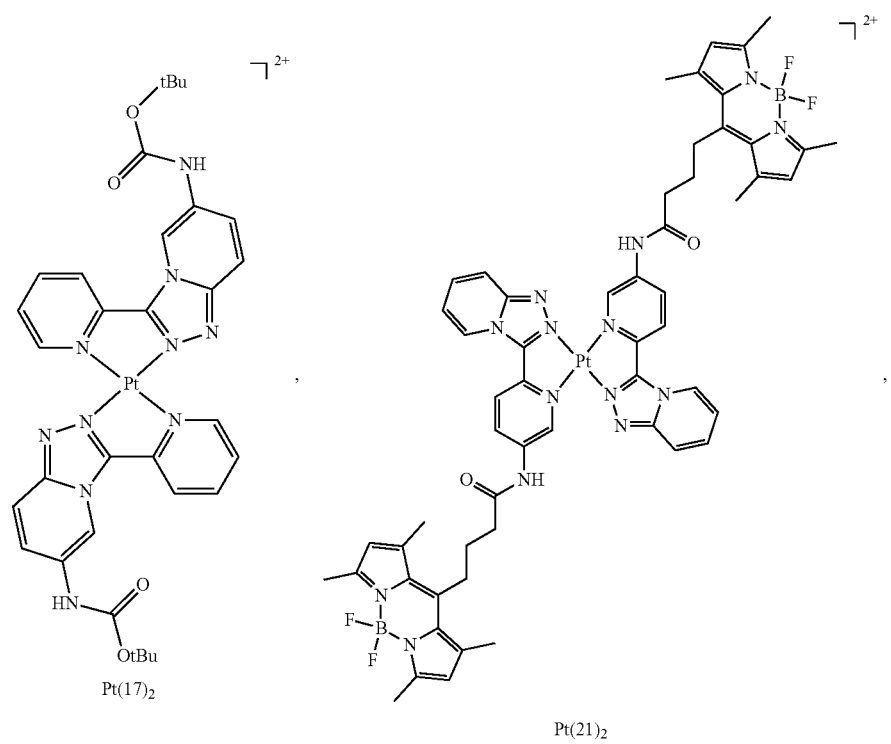

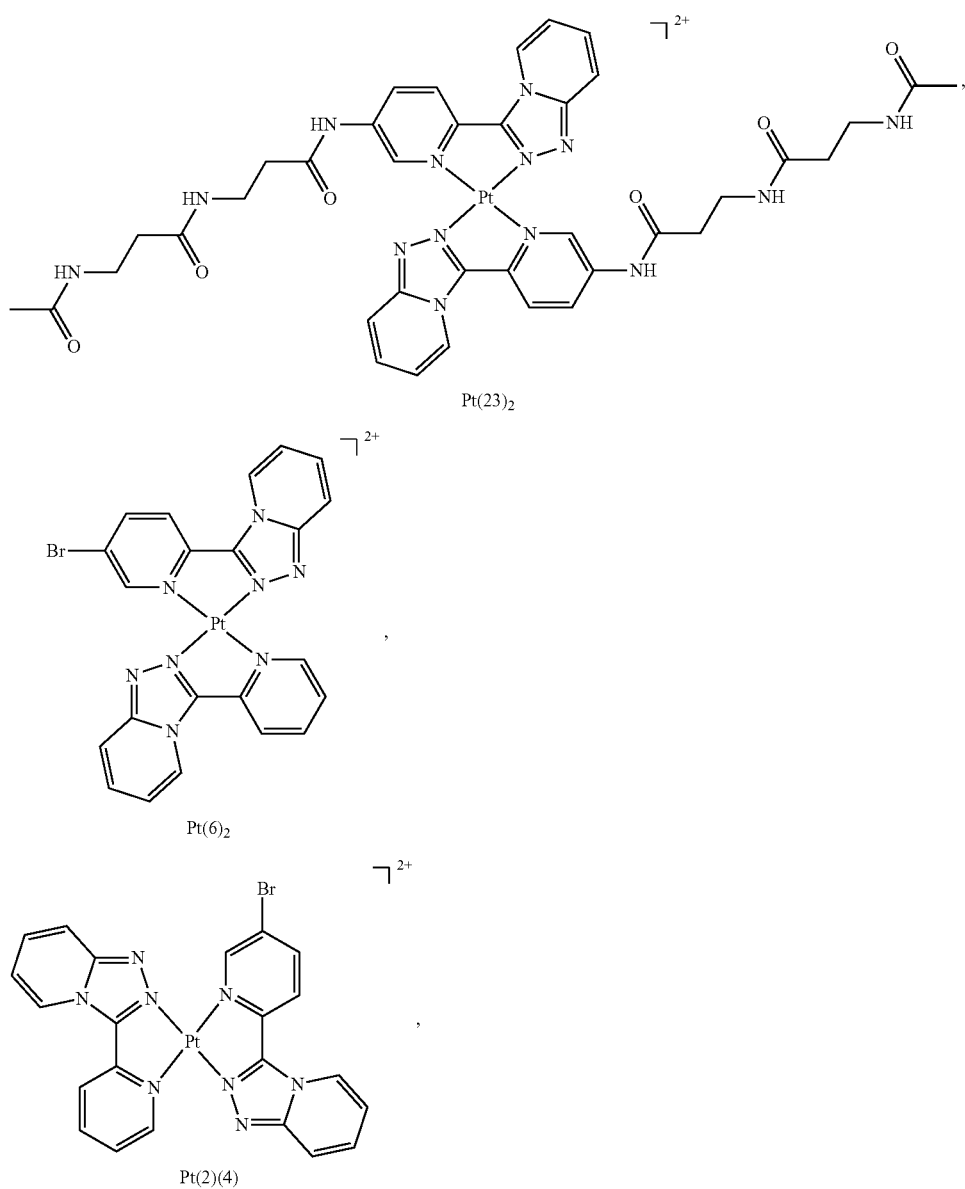

a combination thereof, or a salt or prodrug thereof.

3. A pharmaceutical composition comprising an effective amount of the compound of formula (1) of claim 1, or a pharmaceutically acceptable salt thereof, and a pharmaceutically acceptable excipient.

4. The pharmaceutical composition according to claim 3, wherein the compound has anticancer, anti-infective, or neuroprotective activity.

5. The pharmaceutical composition of claim 4, further comprising active ingredients of other medicaments.

6. The pharmaceutical composition as claimed in claim 3, wherein the pharmaceutical composition further comprises a protein or a glycosaminoglycan.

7. The pharmaceutical composition as claimed in claim 6, wherein the glycosaminoglycan is hyaluronic acid.

8. The pharmaceutical composition of claim 6, wherein the protein is an antibody, hemoglobin, alphafeto-protein, fibrinogen, or serum albumin.

9. A method of treating a disease, comprising administering to a mammal in need thereof an effective amount of the compound of formula (1) of claim 1, or a pharmaceutically acceptable salt or prodrug thereof, wherein the disease is cancer.

10. A method of detection, comprising adding an imaging agent and the compound of formula (1) of claim 1 to a sample, and determining the amount of signal from the imagining agent.

11. The method of claim 10, wherein the method detects presence or absence of a guanine quadruplex in the sample.

12. A method of detection, comprising adding the compound of formula (1) of claim 1 with intrinsic fluorescent properties to a sample, and determining the amount of fluorescence.

13. The method of claim 12, wherein the method detects presence or absence of a guanine quadruplex in the sample.

14. The method of claim 12, for use in affinity determination imaging, detection and/or diagnostics.

15. A method of binding a guanine quadruplex or fragment thereof, comprising adding the compound of formula (1) of claim 1 to a sample that comprises a guanine quadruplex.

16. The compound of claim 1, wherein the compound binds a guanine quadruplex of DNA, RNA, or a combination of DNA and RNA.

17. The compound of claim 16, wherein the guanine quadruplex is of SEQ ID NO: 1 to 12, or a portion thereof.

18. The compound of claim 1, wherein the compound interferes with telomeric function, or inhibits expression of an oncogene.

* * * * *

SEQUENCE LISTING

<160> NUMBER OF SEQ ID NOS: 12

<210> SEQ ID NO 1
<211> LENGTH: 21
<212> TYPE: RNA
<213> ORGANISM: Artificial Sequence
<220> FEATURE:
<223> OTHER INFORMATION: SYNTHETIC

<400> SEQUENCE: 1
ggguuagggu uagggguuagg g          21

<210> SEQ ID NO 2
<211> LENGTH: 21
<212> TYPE: DNA
<213> ORGANISM: Artificial Sequence
<220> FEATURE:
<223> OTHER INFORMATION: SYNTHETIC

<400> SEQUENCE: 2
gggttagggt tagggttagg g                                         21

<210> SEQ ID NO 3
<211> LENGTH: 22
<212> TYPE: DNA
<213> ORGANISM: Artificial Sequence
<220> FEATURE:
<223> OTHER INFORMATION: SYNTHETIC

<400> SEQUENCE: 3
agggttaggg ttagggttag gg                                        22

<210> SEQ ID NO 4
<211> LENGTH: 21
<212> TYPE: DNA
<213> ORGANISM: Artificial Sequence
<220> FEATURE:
<223> OTHER INFORMATION: SYNTHETIC

<400> SEQUENCE: 4
gggctagggc tagggctagg g                                         21

<210> SEQ ID NO 5
<211> LENGTH: 25
<212> TYPE: DNA
<213> ORGANISM: Artificial Sequence
<220> FEATURE:
<223> OTHER INFORMATION: SYNTHETIC

<400> SEQUENCE: 5
agggtgggtg taagtgtggg tgggt                                     25

<210> SEQ ID NO 6
<211> LENGTH: 16
<212> TYPE: DNA
<213> ORGANISM: Artificial Sequence
<220> FEATURE:
<223> OTHER INFORMATION: SYNTHETIC

<400> SEQUENCE: 6
ggttaggtta ggttgg                                               16

<210> SEQ ID NO 7
<211> LENGTH: 23
<212> TYPE: DNA
<213> ORGANISM: Artificial Sequence
<220> FEATURE:
<223> OTHER INFORMATION: SYNTHETIC

<400> SEQUENCE: 7
ttgagggtgg gtagggtggg taa                                       23

<210> SEQ ID NO 8
<211> LENGTH: 22
<212> TYPE: DNA

```
<213> ORGANISM: Artificial Sequence
<220> FEATURE:
<223> OTHER INFORMATION: SYNTHETIC

<400> SEQUENCE: 8
tgagggtggg tagggtgggt aa                                    22

<210> SEQ ID NO 9
<211> LENGTH: 15
<212> TYPE: DNA
<213> ORGANISM: Artificial Sequence
<220> FEATURE:
<223> OTHER INFORMATION: SYNTHETIC

<400> SEQUENCE: 9
ggttggtgtg gttgg                                            15

<210> SEQ ID NO 10
<211> LENGTH: 10
<212> TYPE: DNA
<213> ORGANISM: Artificial Sequence
<220> FEATURE:
<223> OTHER INFORMATION: SYNTHETIC

<400> SEQUENCE: 10
tatagctata                                                  10

<210> SEQ ID NO 11
<211> LENGTH: 10
<212> TYPE: DNA
<213> ORGANISM: Artificial Sequence
<220> FEATURE:
<223> OTHER INFORMATION: SYNTHETIC

<400> SEQUENCE: 11
tatagctata                                                  10

<210> SEQ ID NO 12
<211> LENGTH: 26
<212> TYPE: DNA
<213> ORGANISM: Artificial Sequence
<220> FEATURE:
<223> OTHER INFORMATION: SYNTHETIC

<400> SEQUENCE: 12
caatcggatc gaattcgatc cgattg                                26
```